US010294487B2

(12) United States Patent
Albert et al.

(10) Patent No.: US 10,294,487 B2
(45) Date of Patent: May 21, 2019

(54) METHODS AND COMPOSITIONS INVOLVING ALS VARIANTS WITH NATIVE SUBSTRATE PREFERENCE

(71) Applicants: E I DU PONT DE NEMOURS AND COMPANY, Wilmington, DE (US); PIONEER HI-BRED INTERNATIONAL INC, Johnston, IA (US)

(72) Inventors: Henrik Albert, Alameda, CA (US); John Lawrence Andreassi, II, Hockessin, DE (US); Sean Bertain, Oakland, CA (US); Linda A Castle, Mountain View, CA (US); Steven Gutteridge, Wilmington, DE (US); Daniel L Siehl, Menlo Park, CA (US); Kay Walter, Sunnyvale, CA (US)

(73) Assignees: E I DU PONT DE NEMOURS AND COMPANY, Wilmington, DE (US); PIONEER HI-BRED INTERNATIONAL, INC.IA (US)

( * ) Notice: Subject to any disclaimer, the term of this patent is extended or adjusted under 35 U.S.C. 154(b) by 144 days.

(21) Appl. No.: 13/915,638

(22) Filed: Jun. 12, 2013

(65) Prior Publication Data

US 2013/0340114 A1 Dec. 19, 2013

Related U.S. Application Data

(60) Provisional application No. 61/660,097, filed on Jun. 15, 2012.

(51) Int. Cl.
*C12N 15/82* (2006.01)
*C07K 14/415* (2006.01)

(52) U.S. Cl.
CPC ........ *C12N 15/8274* (2013.01); *C07K 14/415* (2013.01); *C12N 15/8278* (2013.01)

(58) Field of Classification Search
CPC ........ A01N 43/48; C12N 15/11; C12N 15/82; A01P 13/00
See application file for complete search history.

(56) References Cited

U.S. PATENT DOCUMENTS

| 5,141,870 | A | 8/1992 | Bedbrook et al. |
| 5,378,824 | A | 1/1995 | Bedbrook et al. |
| 5,605,011 | A | 2/1997 | Bedbrook et al. |
| 2003/0097692 | A1* | 5/2003 | Jander ............ C12N 9/88 800/300 |
| 2008/0234130 | A1* | 9/2008 | McCutchen ...... C12N 9/1092 504/128 |

FOREIGN PATENT DOCUMENTS

| EP | 0525384 B1 | 8/2000 |
| WO | 2006/076717 A2 | 7/2006 |
| WO | 2010/080430 A1 | 7/2010 |
| WO | 2012/009548 A2 | 1/2012 |

OTHER PUBLICATIONS

Zambiazi, Rui C., et al. "Fatty acid composition of vegetable oils and fats." B. CEPPA, Curitiba 25.1 (2007): 111-120.*
DP305423, supporting document to Australia and New Zealand Food Standards.*
Duggleby, Ronald G., et al. "Systematic characterization of mutations in yeast acetohydroxyacid synthase." European Journal of Biochemistry 270.13 (2003): 2895-2904.*
Haughn, George W., et al. "Transformation with a mutant *Arabidopsis* acetolactate synthase gene renders tobacco resistant to sulfonylurea herbicides." Molecular and General Genetics MGG 211.2 (1988): 266-271.*
McCourt, J. A., and R. G. Duggleby. "Acetohydroxyacid synthase and its role in the biosynthetic pathway for branched-chain amino acids." Amino acids 31.2 (2006): 173-210.*
Chong, Chom-Kyu, and Jung-Do Choi. "Amino acid residues conferring herbicide tolerance in tobacco acetolactate synthase." Biochemical and biophysical research communications 279.2 (2000): 462-467.*
Le, Dung Tien, et al. "Two consecutive aspartic acid residues conferring herbicide resistance in tobacco acetohydroxy acid synthase." Biochimica et Biophysica Acta (BBA)-Proteins and Proteomics 1749.1 (2005): 103-112.*
Haughn, George W., et al. 1988, Molecular and General Genetics 211 (2): 266-271.*
Haughn, G. W., Smith, J., Mazur, B., & Somerville, C. (1988). Transformation with a mutant *Arabidopsis* acetolactate synthase gene renders tobacco resistant to sulfonylurea herbicides. Molecular and General Genetics MGG, 211(2), 266-271.*
Duggleby, Ronald G., and Siew Siew Pang. "Acetohydroxyacid synthase." BMB Reports 33.1 (2000): 1-36.*
Haughn, G. W., Smith, J., Mazur, B., & Somerville, C. (1988). Transformation with a mutant *Arabidopsis* acetolactate synthase gene renders tobacco resistant to sulfonylurea herbicides. Molecular and General Genetics MGG, 211(2), 266-271. (Year: 1988).*
Duggleby, Ronald G., and Siew Siew Pang. "Acetohydroxyacid synthase." BMB Reports 33.1 (2000): 1-36 (Year: 2000).*

(Continued)

*Primary Examiner* — Weihua Fan

(57) ABSTRACT

Compositions and methods comprising polynucleotides and polypeptides having ALS activity and tolerance to at least one ALS inhibitor are provided. In specific embodiments, the sequence has an increased preference for 2-ketobutyrate, when compared to an appropriate control, such as for example, HRA, and/or a preference for 2-ketobutyrate similar to a native ALS. Further provided are nucleic acid constructs, plants, plant cells, explants, seeds and grain having the ALS inhibitor tolerant sequences. Various methods of employing the ALS inhibitor tolerant sequences are provided. Such methods include methods for producing an ALS inhibitor tolerant plant, plant cell, explant or seed and methods of controlling weeds in a field containing a crop employing the plants and/or seeds disclosed herein.

4 Claims, 1 Drawing Sheet

Specification includes a Sequence Listing.

(56) References Cited

OTHER PUBLICATIONS

Yu, Qin, et al. "AHAS herbicide resistance endowing mutations: effect on AHAS functionality and plant growth." Journal of Experimental Botany 61.14 (2010): 3925-3934. (Year: 2010).*

Jander, Georg, et al. "Ethylmethanesulfonate saturation mutagenesis in *Arabidopsis* to determine frequency of herbicide resistance." Plant Physiology 131.1 (2003): 139-146 (Year: 2003).*

Paul Bernasconi et al., A Naturally Occurring Point Mutation Confers Broad Range Tolerance to Herbicides That Target Acetolactate Synthase; The Journal of Biological Chemistry, Jul. 21, 1995, pp. 17381-17385, vol. 270, No. 21.

Alan K. Chang et al., Herbicide-resistant forms of *Arabidopsis thaliana* acetohydroxyacid synthase: characterization of the catalytic properties and sensitivity to inhibitors of four defined mutants; Biochem J, 1998, p. 765-777, vol. 333.

Chom-Kyu Chong et al., Amino Acid Residues Conferring Herbicide Tolerance in Tobacco Acetolactate Synthase; Biochemical and Biophysical Research Communications, 2000, pp. 462-467, vol. 279.

Ronald G. Duggleby et al., Systematic characterization of mutations in yeast acetohydroxyacid synthase, Eur. J. Biochem, 2003, pp. 2895-2904, vol. 270.

Ronald G. Duggleby et al., Structure and mechanism of inhibition of plant acetohydroxyacid synthase, Plant Physiology and Biochemistry, 2008, pp. 309-324, vol. 46.

Jiro Hattori et al., An acetohydroxy acid synthase mutant reveals a single site involved in multiple herbicide resistance, Mol. Gen. Genet, 1995, pp. 419-425, vol. 246.

George W. Haughn et al., Sulfonylurea-resistant mutants of *Arabidopsis thaliana*; Mol. Gen Genet, 1986, pp. 430-434, vol. 204.

Craig M. Hill et al., Mutagenesis of *Escherichia coli* acetohydroxyacid synthase isoenzyme II and characterization of three herbicide-insensitive forms, Biochem J., 1998, pp. 653-661, vol. 335.

Muhammad Ibdah et al., Homology Modeling of the Structure of Bacterial Acetohydroxy Acid Synthase and Examination of the Active Site by Site-Directed Mutagenesis; Biochemistry, 1996, pp. 16282-16291, vol. 35.

Sun-Mi Jung et al., Amino acid residues conferring herbicide resistance in tobacco acetohydroxy acid synthase; Biochem J., 2004, pp. 53-61, vol. 383.

Judith M. Kilkman et al., Acetohydroxyacid synthase mutations conferring resistance to imidazolinone or sulfonylurea herbicides in sunflower; Theor Appl Genet, 2004, pp. 1147-1159, vol. 109.

Dung Tien Le et al., Roles of conserved methionine residues in tobacco acetolactate synthase, Biochemical and Biophysical Research Communications, 2003, pp. 1075-1082, vol. 306.

Kathleen Y. Lee et al., The Molecular basis of sulfonylurea herbicide resistance in tobacco; The EMBO Journal, 1988, pp. 1241-1248, vol. 7, No. 5.

International Search Report—PCT/US2013/044969—dated Dec. 11, 2013.

* cited by examiner

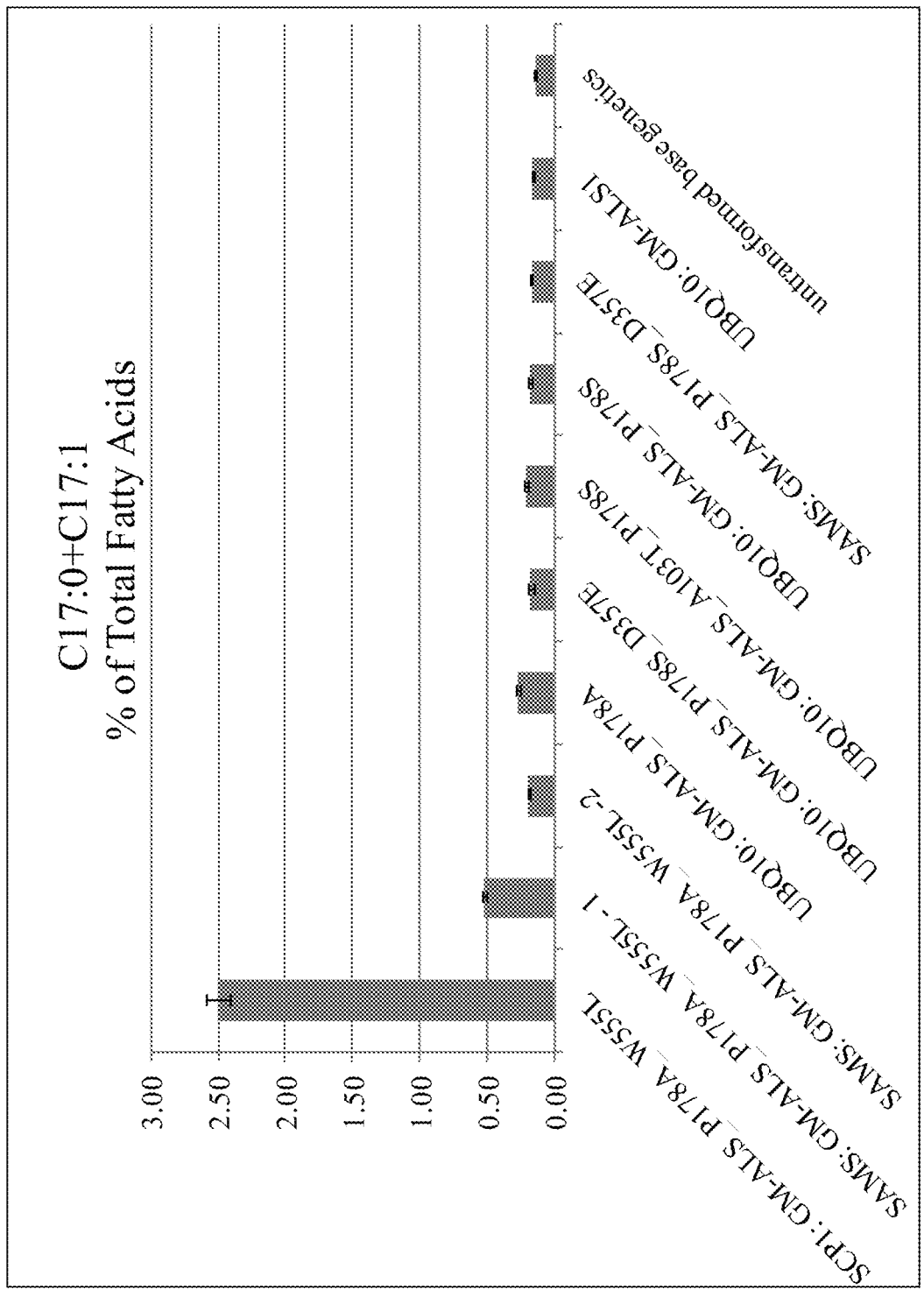

METHODS AND COMPOSITIONS INVOLVING ALS VARIANTS WITH NATIVE SUBSTRATE PREFERENCE

CROSS REFERENCE TO RELATED APPLICATIONS

This application claims the benefit of U.S. Provisional Application No. 61/660,097, filed Jun. 15, 2012, the entire content of which is herein incorporated by reference.

FIELD OF THE INVENTION

This invention is in the field of molecular biology. More specifically, this invention pertains to sequences that confer tolerance to ALS inhibiting herbicides.

BACKGROUND OF THE INVENTION

Acetolactate synthase (ALS), also known as acetohydroxyacid synthase (AHAS), catalyzes the biosynthesis of the branched chain amino acids valine, leucine and isoleucine (Singh (1999) "Biosynthesis of valine, leucine and isoleucine," in *Plant Amino Acids*, Singh, B. K., ed., Marcel Dekker Inc. New York, N.Y., pp. 227-247). A number of compounds such as, for example, sulfonylurea, imidazolinone, triazolopyrimidines, pyrimidinyoxy(thio)benzoates, and/or sulfonylamino-carbonyl-triazonline herbicide, inhibit ALS activity such as for example in plants, enabling the use of such compounds as herbicides. It is desirable to produce crop plants that are tolerant to ALS-inhibiting herbicides, thereby allowing tolerant crop plants to thrive and non-tolerant plants (e.g. weeds) to be killed or severely damaged upon treatment with one or more ALS-inhibiting herbicide.

Tolerance to ALS-inhibiting herbicides has been achieved in at least six crops (Shaner et al. (2007) "Imidazolinone Herbicides," in *Modern Crop Protection Compounds*. Volume 1., W. Kramer and U. Schirmer, eds., Wiley-VCH Verlag. Weinheim, Germany, pp. 82-92; Tan et al. (2005) Imidazolinone-tolerant crops: history, current status and future. *Pest Manag. Sci.* 61:246-257), largely by way of point mutations in ALS genes that render the encoded ALS enzymes insensitive to some or all ALS-inhibiting herbicides. Different mutations in ALS are known to confer tolerance to different ALS herbicides and groups (and/or subgroups) thereof; (see, e.g., Tranel and Wright (2002) *Weed Science* 50:700-712).

Few if any of the ALS mutations have been fully characterized with respect to the active ingredients to which they confer insensitivity or to the effects they have on the catalytic and cofactor binding properties of the enzyme. For example, some mutations in ALS may lead to altered substrate preference, which may have downstream effects on an organism that expresses the mutated ALS sequence. It is desirable to identify mutations in ALS that not only confer insensitivity to one or more ALS inhibitors but also allow the enzyme to behave kinetically similar to a wild type ALS, thereby minimizing any potentially detrimental effects on an organism expressing the mutated ALS sequence.

SUMMARY OF THE INVENTION

Compositions and methods comprising polynucleotides and polypeptides having acetolactate synthase (ALS) activity and tolerance to at least one ALS inhibitor are provided. In some embodiments, the ALS inhibitor-tolerant polypeptide has an increased preference for 2-ketobutyrate, when compared to an appropriate control, such as for example, HRA (SEQ ID NO:10), and/or a preference for 2-ketobutyrate similar to a native ALS (e.g. GM-ALS1; SEQ ID NO:1) while retaining insensitivity to at least one ALS-inhibitor. Further provided are nucleic acid constructs, plants, plant cells, explants, seeds and grain having the ALS inhibitor-tolerant sequences.

Various methods of employing the ALS inhibitor-tolerant sequences are provided. Such methods include methods for producing an ALS inhibitor-tolerant organism, plant, plant cell, explant or seed and methods of controlling weeds in a field containing a crop employing the plants and/or seeds.

BRIEF DESCRIPTION OF THE DRAWINGS AND SEQUENCE LISTING

The invention can be more fully understood from the following detailed description and the accompanying drawings and Sequence Listing which form a part of this application.

FIG. 1 shows C17 fatty acids as a percent of total fatty acids measured in transgene positive soy seed expressing variant ALS inhibitor-tolerant polypeptides under various promoters of differing strengths. All seeds were homozygous for the ALS inhibitor-tolerant gene insert, except for the untransformed seed. Error bars for data sets are shown. The sequence descriptions and Sequence Listing attached hereto comply with the rules governing nucleotide and/or amino acid sequence disclosures in patent applications as set forth in 37 C.F.R. § 1.821 1.825. The Sequence Listing contains the one letter code for nucleotide sequence characters and the three letter codes for amino acids as defined in conformity with the IUPAC IUBMB standards described in Nucleic Acids Res. 13:3021 3030 (1985) and in the Biochemical J. 219 (2):345 373 (1984) which are herein incorporated by reference. The symbols and format used for nucleotide and amino acid sequence data comply with the rules set forth in 37 C.F.R. § 1.822.

SEQ ID NO:1 is the amino acid sequence of the *Glycine Max* ALS1 protein.

SEQ ID NO:2 is the amino acid sequence of the *Glycine Max* ALS1 variant with a G→S mutation at position 102.

SEQ ID NO:3 is the amino acid sequence of the *Glycine Max* ALS1 protein with a G→S mutation at position 102 and a P→S mutation at position 178.

SEQ ID NO:4 is the amino acid sequence of the *Glycine Max* ALS1 protein with a G→S mutation at position 102 and a D→E mutation at position 357.

SEQ ID NO:5 is the amino acid sequence of the *Glycine Max* ALS1 protein with a G→S mutation at position 102 and a D→N mutation at position 357.

SEQ ID NO:6 is the amino acid sequence of the *Glycine Max* ALS1 variant with a A→T mutation at position 103.

SEQ ID NO:7 is the amino acid sequence of the *Glycine Max* ALS1 protein with a A→T mutation at position 103 and a P→S mutation at position 178.

SEQ ID NO:8 is the amino acid sequence of the *Glycine Max* ALS1 protein with a A→T mutation at position 103, a P→S mutation at position 178, and a D→E mutation at position 357.

SEQ ID NO:9 is the amino acid sequence of the *Glycine Max* ALS1 variant with a P→A mutation at position 178.

SEQ ID NO:10 is the amino acid sequence of the *Glycine Max* ALS1 variant with a P→A mutation at position 178 and a W→L mutation at position 555.

SEQ ID NO:11 is the amino acid sequence of the *Glycine Max* ALS1 variant with a P→A mutation at position 178 and a F→D mutation at position 559.

SEQ ID NO:12 is the amino acid sequence of the *Glycine Max* ALS1 variant with a P→L mutation at position 178.

SEQ ID NO:13 is the amino acid sequence of the *Glycine Max* ALS1 variant with a P→L mutation at position 178 and a W→L mutation at position 555.

SEQ ID NO:14 is the amino acid sequence of the *Glycine Max* ALS1 variant with a P→Q mutation at position 178.

SEQ ID NO:15 is the amino acid sequence of the *Glycine Max* ALS1 variant with a P→S mutation at position 178.

SEQ ID NO:16 is the amino acid sequence of the *Glycine Max* ALS1 variant with a P→S mutation at position 178 and a A→V mutation at position 186.

SEQ ID NO:17 is the amino acid sequence of the *Glycine Max* ALS1 variant with a P→S mutation at position 178 and a D→E mutation at position 357.

SEQ ID NO:18 is the amino acid sequence of the *Glycine Max* ALS1 variant with a P→S mutation at position 178 and a D→N mutation at position 357.

SEQ ID NO:19 is the amino acid sequence of the *Glycine Max* ALS1 variant with a P→S mutation at position 178 and a F→D mutation at position 559.

SEQ ID NO:20 is the amino acid sequence of the *Glycine Max* ALS1 variant with a A→D mutation at position 186.

SEQ ID NO:21 is the amino acid sequence of the *Glycine Max* ALS1 variant with a A→V mutation at position 186.

SEQ ID NO:22 is the amino acid sequence of the *Glycine Max* ALS1 variant with a K→F mutation at position 237.

SEQ ID NO:23 is the amino acid sequence of the *Glycine Max* ALS1 variant with a K→Q mutation at position 237.

SEQ ID NO:24 is the amino acid sequence of the *Glycine Max* ALS1 variant with a D→E mutation at position 357.

SEQ ID NO:25 is the amino acid sequence of the *Glycine Max* ALS1 variant with a D→N mutation at position 357.

SEQ ID NO:26 is the amino acid sequence of the *Glycine Max* ALS1 variant with a W→L mutation at position 555.

SEQ ID NO:27 is the amino acid sequence of the *Glycine Max* ALS1 variant with a F→D mutation at position 559.

SEQ ID NO:28 is the amino acid sequence of the *Glycine Max* ALS1 variant with a F→L mutation at position 559.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

I. Compositions

A. Acetolactate Synthase (ALS) Inhibitor Tolerant Polynucleotides and Polypeptides As used herein, an "acetolactate synthase" (ALS), otherwise referred to as an acetohydroxyacid synthase (AHAS), comprises a polypeptide which has acetolactate synthase activity ("ALS" activity), i.e., the ability to catalyze the biochemical synthesis of the branched chain amino acids valine, leucine and isoleucine (Singh (1999) "Biosynthesis of valine, leucine and isoleucine," in *Plant Amino Acids*, Singh, B. K., ed., Marcel Dekker Inc. New York, N.Y., pp. 227-247).

An "ALS inhibitor-tolerant polypeptide" comprises an ALS polypeptide which when expressed in a plant confers tolerance to at least one ALS inhibitor. An "ALS inhibitor-tolerant polynucleotide" comprises a sequence that encodes an ALS inhibitor-tolerant polypeptide. A variety of ALS inhibitors are known and include, for example, sulfonylurea, imidazolinone, triazolopyrimidines, pyrimidinyoxy(thio) benzoates, and/or sulfonylamino-carbonyl-triazolinone herbicides. It is known in the art that ALS mutations fall into different classes with regard to tolerance to sulfonylureas, imidazolinones, triazolopyrimidines, and pyrimidinylthiobenzoates, including mutations having the following characteristics: (1) broad tolerance to all four of these groups; (2) tolerance to imidazolinones and pyrimidinylthiobenzoates; (3) tolerance to sulfonylureas and triazolopyrimidines; and (4) tolerance to sulfonylureas and imidazolinones.

ALS inhibitor-tolerant polynucleotides may contain at least one nucleotide mutation resulting in one amino acid change in the ALS polypeptide, and the change may occur in one of seven substantially conserved regions of acetolactate synthase. See, for example, Hattori et al. (1995) *Molecular Genetic and Genomes* 246:419-425; Lee et al. (1998) *EMBO Journal* 7:1241-1248; Mazur et al. (1989) *Ann. Rev. Plant Phys.* 40:441-470; and U.S. Pat. No. 5,605,011, each of which is incorporated by reference in their entirety. The ALS inhibitor-tolerant polypeptide may comprise a number of mutations. Different mutations in ALS are known to confer tolerance to different herbicides and groups (and/or subgroups) of herbicides (see e.g., Duggleby et al. (2008) *Plant Physiol and Biochem* 46:309-324; Tranel and Wright (2002) *Weed Science* 50:700-712); and U.S. Pat. Nos. 6,605,011; 5,378,824; 5,141,870; and 5,013,659, each of which is herein incorporated by reference in their entirety).

Native ALS polypeptides carry out two parallel reactions leading to specific branched chain amino acids. Reaction with one 2-ketobutyrate molecule and one pyruvate molecule leads to synthesis of 2-aceto-2-hydroxybutyrate (AHB) and eventually isoleucine, whereas reaction with two pyruvate molecules leads to formation of 2-acetolactate (AL) and eventually valine and leucine. Plant ALS polypeptides have a preference for 2-ketobutyrate over pyruvate, but the cellular concentration of pyruvate is higher resulting in a balance of the 2 pathways. Mutations in ALS can alter the preference of ALS for one or the other substrate leading to downstream effects. For example, loss of substrate preference for 2-ketobutyrate in some ALS variant enzymes (e.g. GM-ALS_W555L) may lead to an increase in the pool size for this metabolite, which in turn may result in increased biosynthesis of C17 fatty acids (FAs) via propionyl-CoA replacing acetyl-CoA. Heptadecanoic acid (C17:0) and heptadecenoic acid (C17:1) are widely distributed in nature and have been identified as components of foods and feed routinely consumed in the diets of humans and other mammals. Both fatty acids are readily metabolized in humans and other mammals. No safety or nutritional concerns are expected as a result of this slight increase in exposure.

The "substrate specificity ratio", or "Rf", characterizes the specificity of the ALS enzyme for AHB formation relative to AL formation (Gollop et al. (1989) *Biochemistry* 28:6310-6317). Rf is the ratio of [pyruvate] to [2-ketobutyrate] that results in equal rates of formation of acetolactate and acetohydroxybutyrate. Rf is a constant at all substrate concentrations. The substrate specificity ratio is ~114 for the wild type *Glycine max* ALS1 enzyme (SEQ ID NO:1) compared to ~3 for the highly resistant allele (HRA) double mutant variant (SEQ ID NO: 10) of the *Glycine max* ALS1. The soybean HRA sequence is disclosed, for example, in WO2007/024782, herein incorporated by reference.

In some embodiments, the ALS inhibitor-tolerant polypeptides have an increased preference for 2-ketobutyrate, as compared to a control, e.g. the highly resistant allele (HRA) double mutant variant (SEQ ID NO: 10), or have a preference for 2-ketobutyrate similar to the wild type *Glycine max* ALS1 enzyme (SEQ ID NO:1) while retaining insensitivity to at least one ALS-inhibitor. In some embodiments, the ALS inhibitor-tolerant polypeptide has an Rf greater than 3, 5, 10, 15, 20, 25, 30, 35, 40, 45, 50, 55, 60, 65, 70, or 73, and more preferably, an Rf greater than 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, or more. This may include the ALS variants containing the following mutations: P178S (SEQ ID NO:15); P178S/D357E (SEQ ID NO:17); A103T/P178S (SEQ ID NO:7); and A103T/P178S/D357E (SEQ ID NO:8); which have Rf values of 104.0, 100.0, 75.0, and 114.0, respectively (as compared to wild-type GM-ALS1 that has an Rf of 114.0).

As used herein, an "isolated" or "purified" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. When the polypeptide of the invention or biologically active portion thereof is recombinantly produced, optimally culture medium represents less than about 30%, 20%, 10%, 5%, or 1% (by dry weight) of chemical precursors or non-protein-of-interest chemicals.

As used herein, polynucleotide or polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A polypeptide expressed in vitro or in vivo from a recombinant polynucleotide is an example of a recombinant polypeptide. Likewise, a polynucleotide sequence that does not appear in nature, for example, a variant of a naturally occurring gene is recombinant.

A "mutated" polynucleotide or polypeptide or a "mutagenized" polynucleotide or polypeptide, refers to a polynucleotide or polypeptide having one or more nucleotide or amino acid substitutions, deletions, or transversions compared to the nucleotide or amino acid at an equivalent position in a non-mutated, or wild-type, polynucleotide or polypeptide. The terms refer to a polynucleotide or polypeptide that is modified from its native or wild type form as the result of deliberate human manipulation, and does not include natural sequences.

In general, methods to mutate, modify or alter the host endogenous DNA are available. This includes mutating the host native ALS-coding sequence or a pre-existing transgenic sequence including regulatory elements, coding and non-coding sequences. These methods are also useful in targeting nucleic acids to pre-engineered target recognition sequences in the genome. Such methods include chemical mutagenesis methods, as well as site-directed mutagenesis. Examples of chemical mutagenesis include the use of chemical mutagens such as ethyl methanesulfonate (EMS), base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. As an example of site-directed mutagenesis, the mutagenized polynucleotide, polypeptode, host cell or plant described herein, is generated using "custom" meganucleases produced to modify plant genomes (see e.g., WO 2009/114321; Gao et al. (2010) *Plant Journal* 1:176-187). Another site-directed engineering is through the use of zinc finger domain recognition coupled with the restriction properties of restriction enzyme. See e.g., Urnov, et al., (2010) *Nat Rev Genet.* 11(9):636-46; Shukla, et al., (2009) *Nature* 459 (7245):437-41. A transcription activator-like (TAL) effector-DNA modifying enzyme (TALE or TALEN) is also used to engineer changes in plant genome. See e.g., US20110145940, Cermak et al., (2011) *Nucleic Acids Res.* 39(12) and Boch et al., (2009), *Science* 326(5959): 1509-12. Another example of site-directed mutagenesis is the use of gene repair oligonucleotides (GRON) to introduce a desired mutation to the ALS sequence. See e.g., US20120060243. Mutagenesis is also obtained through the use of radiation, such as X-rays, Gamma rays (e.g., cobalt 60 or cesium 137), neutrons, (e.g., product of nuclear fission by uranium 235 in an atomic reactor), Beta radiation (e.g., emitted from radioisotopes such as phosphorus 32 or carbon 14), and ultraviolet radiation (preferably from 250 to 290 nm).

A "control" or "control plant" or "control plant cell" provides a reference point for measuring changes in phenotype of the subject plant or plant cell, and may be any suitable plant or plant cell. A control plant or plant cell may comprise, for example: (a) a wild-type or native plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell which is genetically identical to the subject plant or plant cell but which is not exposed to the same treatment (e.g., herbicide treatment) as the subject plant or plant cell; or (e) the subject plant or plant cell itself, under conditions in which the gene of interest is not expressed.

B. Active Fragments and Variants of ALS Inhibitor-Tolerant Sequences

Methods and compositions are provided which employ ALS inhibitor-tolerant polynucleotides and polypeptides. Furthermore, any given variant or fragment of an ALS-inhibitor tolerant sequence may have an increased preference for 2-ketobutyrate, when compared to an appropriate control, such as for example, HRA (SEQ ID NO:10), and/or a preference for 2-ketobutyrate similar to a native ALS (e.g. GM-ALS1; SEQ ID NO:1); while retaining tolerance to at least one ALS-inhibitor.

i. Polynucleotide and Polypeptide Fragments

Fragments and variants of ALS inhibitor-tolerant polynucleotides and polypeptides are also encompassed by the present invention. By "fragment" is intended a portion of the polynucleotide or a portion of the amino acid sequence and hence protein encoded thereby. Fragments of a polynucleotide may encode protein fragments that retain ALS activity and tolerance to at least one ALS inhibitor, and in other embodiments, have an increased preference for 2-ketobutyrate, when compared to an appropriate control, such as for example, HRA (SEQ ID NO:10), and/or a preference for 2-ketobutyrate similar to a native ALS (e.g. GM-ALS1; SEQ ID NO:1). Alternatively, fragments of a polynucleotide that are useful as hybridization probes or PCR primers generally do not encode fragment proteins retaining biological activity. Thus, fragments of a nucleotide sequence may range from at least about 20 nucleotides, about 50 nucleotides, about 100 nucleotides, and up to the full-length polynucleotide encoding the ALS inhibitor-tolerant polypeptides. A fragment of an ALS inhibitor-tolerant polynucleotide that encodes a biologically active portion of an ALS inhibitor-tolerant protein of the invention will encode at least 50, 75, 100, 150, 175, 200, 225, 250, 275, 300, 325, 350, 375, 400, 425, 450, 475, 500, 525, 550, 575, 600, 625, 630, 635, 640, 645, or 650 contiguous amino acids, or up to the total number of amino acids present in a full-length ALS polypeptide.

Thus, a fragment of an ALS inhibitor-tolerant polynucleotide may encode a biologically active portion of an ALS polypeptide, or it may be a fragment that can be used as a hybridization probe or PCR primer using methods disclosed below. A biologically active portion of an ALS polypeptide can be prepared by isolating a portion of one of the ALS polynucleotides, expressing the encoded portion of the ALS inhibitor-tolerant polypeptides (e.g., by recombinant expression in vitro), and assessing the activity. Polynucleotides that are fragments of an ALS inhibitor-tolerant nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, 1,400, 1,500, 1,600, 1,700, 1,800, or 1,900 contiguous nucleotides, or up to the number of nucleotides present in a full-length ALS inhibitor-tolerant polynucleotide disclosed herein.

Fragments of a polypeptide may encode protein fragments that retain ALS activity and tolerance to at least one ALS inhibitor, and in some embodiments, an increased preference for 2-ketobutyrate, when compared to an appropriate control, such as for example, HRA (SEQ ID NO:10), and/or a preference for 2-ketobutyrate similar to a native ALS (e.g. GM-ALS1; SEQ ID NO:1). A fragment of an ALS inhibitor-tolerant polypeptide disclosed herein will encode at least 50, 75, 100, 150, 175, 200, 225, 250, 275, 300, 325, 350, 375, 400, 425, 450, 475, 500, 525, 550, 575, 600, 625, 630, 635, 640, 645, or 650 contiguous amino acids, or up to the total number of amino acids present in a full-length ALS inhibitor-tolerant polypeptide.

ii. Polynucleotide and Polypeptide Variants

"Variant" protein is intended to mean a protein derived from the protein by deletion (i.e., truncation at the 5' and/or 3' end) and/or a deletion or addition of one or more amino acids at one or more internal sites in the native protein and/or substitution of one or more amino acids at one or more sites in the native protein. Variant proteins encompassed are biologically active, that is they continue to possess the desired biological activity, i.e. ALS activity, and they are tolerant to at least one ALS inhibitor. Moreover, any given variant or fragment may also have an increased preference for 2-ketobutyrate, when compared to an appropriate control, such as for example, HRA (SEQ ID NO:10), and/or a preference for 2-ketobutyrate similar to a native ALS (e.g. GM-ALS1; SEQ ID NO:1). Such variants may result from, for example, genetic polymorphism or from human manipulation (such as, for example, by site-specific recombination).

"Variants" is intended to mean substantially similar sequences. For polynucleotides, a variant comprises a polynucleotide having a deletion (i.e., truncations) at the 5' and/or 3' end and/or a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the ALS inhibitor-tolerant polypeptides of the invention. Naturally occurring variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis or gene synthesis but which still encode an ALS polypeptide.

Biologically active variants of an ALS inhibitor-tolerant polypeptide (and the polynucleotide encoding the same) will have at least about 90%, 91%, 92%, 93%, 93.5%, 94%, 94.5%, 95%, 95.5%, 96%, 96.5%, 97%, 97.5%, 98%, 98.5%, 99%, 99.5%, or more sequence identity to the polypeptide of any one of SEQ ID NOs:1-28 as determined by sequence alignment programs and parameters described elsewhere herein.

The ALS inhibitor-tolerant polypeptide and the active variants and fragments thereof may be altered in various ways including amino acid substitutions, deletions, truncations, and insertions. Methods for such manipulations are generally known in the art. For example, amino acid sequence variants and fragments of the ALS proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Obviously, the mutations that will be made in the DNA encoding the variant must not place the sequence out of reading frame and optimally will not create complementary regions that could produce secondary mRNA structure. See, EP Patent Application Publication No. 75,444.

Variant polynucleotides and proteins also encompass sequences and proteins derived from a mutagenic and recombinogenic procedure such as DNA shuffling. With such a procedure, one or more different ALS coding sequences can be manipulated to create a new ALS possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the ALS sequences disclosed herein and other known ALS genes to obtain a new gene coding for a protein with an improved property of interest, such as an increased preference for 2-ketobutyrate, when compared to an appropriate control, such as for example, HRA (SEQ ID NO:10) and/or a preference for 2-ketobutyrate similar to a native ALS (e.g. GM-ALS1; SEQ ID NO:1). Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Although ALS proteins of various species differ in length by a few amino acids, the relative positions of residues subject to modification in accordance with the present invention are conserved. Accordingly, the mutations described herein are expressed in terms of positions corresponding to the amino acid residue numbers of the *Glycine max ALS*1 polypeptide (SEQ ID NO:1) unless noted otherwise. One of ordinary skill in the art could identify corresponding positions in ALS sequences not specifically disclosed herein.

C. Sequence Comparisons

The following terms are used to describe the sequence relationships between two or more polynucleotides or polypeptides: "reference sequence", "comparison window", "sequence identity", and, "percent sequence identity."

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence or protein sequence.

As used herein, "comparison window" makes reference to a contiguous and specified segment of a polypeptide sequence, wherein the polypeptide sequence in the comparison window may comprise additions or deletions (i.e., gaps) compared to the reference sequence (which does not comprise additions or deletions) for optimal alignment of the two polypeptides. Generally, the comparison window is at least 5, 10, 15, or 20 contiguous amino acid in length, or it can be 30, 40, 50, 100, or longer. Those of skill in the art understand that to avoid a high similarity to a reference sequence due to inclusion of gaps in the polypeptide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci.* USA 872264, modified as in Karlin and Altschul (1993) *Proc. Natl. Acad. Sci.* USA 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. BLASTP protein searches can be performed using default parameters. See, blast.ncbi.nlm.nih.gov/Blast.cgi. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTP for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci.* USA 89:10915).

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity). When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percent sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percent sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percent sequence identity.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acids substitution matrices and their use in quantifying the similarity between two sequences are well-known in the art and described, e.g., in Dayhoff et al. (1978) "A model of evolutionary change in proteins." In *"Atlas of Protein Sequence and Structure,"* Vol. 5, Suppl. 3 (ed. M. O. Dayhoff), pp. 345-352. Natl. Biomed. Res. Found., Washington, D.C. and Henikoff et al. (1992) *Proc. Natl. Acad. Sci.* USA 89:10915-10919. The BLOSUM62 matrix (FIG. 10) is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al, (1997) *Nucleic Acids Res.* 25:3389-3402, and made available to the public at the National Center for Biotechnology Information Website (http://www.ncbi.nlm.nih.gov). Optimal alignments, including multiple alignments, can be prepared using, e.g., PSI-BLAST, available through http://www.ncbi.nlm.nih.gov and described by Altschul et al, (1997) *Nucleic Acids Res.* 25:3389-3402.

D. Plants and Other Host Cells of Interest

Further provided are engineered host cells that are transduced (transformed or transfected) with one or more ALS inhibitor tolerant sequences or active variants or fragments thereof. The ALS inhibitor tolerant polypeptides or variants and fragments thereof can be expressed in any organism, including in non-animal cells such as plants, yeast, fungi, bacteria and the like. Details regarding non-animal cell culture can be found in Payne et al. (1992) *Plant Cell and Tissue Culture in Liquid Systems*, John Wiley & Sons, Inc. New York, N.Y.; Gamborg and Phillips (eds.) (1995) *Plant Cell, Tissue and Organ Culture; Fundamental Methods* Springer Lab Manual, Springer-Verlag (Berlin, Heidelberg, New York); and Atlas and Parks (eds.) *The Handbook of Microbiological Media* (1993) CRC Press, Boca Raton, Fla.

Plants, plant cells, plant parts and seeds, and grain having the ALS sequences disclosed herein are also provided. In some embodiments, the plants and/or plant parts have stably incorporated at least one ALS polypeptide disclosed herein or an active variant or fragment thereof. Thus, plants, plant cells, plant parts and seed are provided which comprise at least one ALS sequence of any one or more of SEQ ID NOs:2-28 or a biologically active fragment and/or variant thereof. In some embodiments, the ALS sequence or active variants and fragments thereof have ALS activity and tolerance to at least one ALS inhibitor. In further embodiments, the sequence has an increased preference for 2-ketobutyrate, when compared to an appropriate control, such as for example, HRA (SEQ ID NO:10), and/or a preference for 2-ketobutyrate similar to a native ALS (e.g. GM-ALS1; SEQ ID NO:1).

In addition, the plants or organism of interest can comprise multiple ALS polynucleotides (i.e., at least 1, 2, 3, 4, 5, 6 or more). It is recognized that if multiple ALS polynucleotides are employed, the ALS polynucleotides may encode ALS polypeptides having (1) different kinetic parameters, i.e., an ALS variant having a lower Rf can be combined with one having a higher Rf or (2) different specificity for 2-ketobutyrate when compared to an appropriate control. In some embodiments, the polynucleotide in the plant or plant part is operably linked to a constitutive, tissue-preferred, or other promoter for expression in plants.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The ALS sequences and active variant and fragments thereof disclosed herein may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow cedar (*Chamaecyparis nootkatensis*), and Poplar and Eucalyptus. In some embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

A "subject plant or plant cell" is one in which genetic alteration, such as transformation, has been affected as to a gene of interest, or is a plant or plant cell which is descended from a plant or cell so altered and which comprises the alteration.

A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

Additional host cells of interest can be a eukaryotic cell, an animal cell, a protoplast, a tissue culture cell, prokaryotic cell, a bacterial cell, such as *E. coli, B. subtilis, Streptomyces, Salmonella typhimurium*, a gram positive bacteria, a purple bacteria, a green sulfur bacteria, a green non-sulfur bacteria, a cyanobacteria, a spirochetes, a thermatogale, a flavobacteria, *bacteroides*; a fungal cell, such as *Saccharomyces cerevisiae, Pichia pastoris*, and *Neurospora crassa*; an insect cell such as *Drosophila* and *Spodoptera frugiperda*; a mammalian cell such as CHO, COS, BHK, HEK 293 or Bowes melanoma, archaebacteria (i.e., *Korarchaeota, Thermoproteus, Pyrodictium, Thermococcales, Methanogens, Archaeoglobus*, and extreme Halophiles) and others.

E. Polynucleotide Constructs

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The ALS inhibitor-tolerant polynucleotides disclosed herein can be provided in expression cassettes for expression in the plant of interest or any organism of interest. The cassette can include 5' and 3' regulatory sequences operably linked to an ALS inhibitor-tolerant polynucleotide or active variant or fragment thereof. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the ALS inhibitor-tolerant polynucleotide or active variant or fragment thereof to be under the transcriptional regulation of the regulatory regions. The expression cassette may additionally contain selectable marker genes.

The expression cassette can include in the 5'-3' direction of transcription, a transcriptional and translational initiation region (i.e., a promoter), an ALS polynucleotide or active variant or fragment thereof, and a transcriptional and translational termination region (i.e., termination region) functional in plants. The regulatory regions (i.e., promoters, transcriptional regulatory regions, and translational termination regions) and/or the ALS polynucleotide or active variant or fragment thereof may be native/analogous to the host cell or to each other (e.g. a native promoter, chloroplast transit peptide, and/or terminator may be used). Alternatively, the regulatory regions and/or the ALS polynucleotide of or active variant or fragment thereof may be heterologous to the host cell or to each other.

As used herein, "heterologous" in reference to a sequence is a sequence that originates from a foreign species, or, if from the same species, is substantially modified from its native form in composition and/or genomic locus by deliberate human intervention. For example, a promoter may be heterologous to the polynucleotide, meaning that is from a species different from the species from which the polynucleotide was derived, or, if from the same/analogous species, one or both of the promoter and polynucleotide are substantially modified from their original form and/or genomic locus, or the promoter is not the native promoter for the operably linked polynucleotide.

The termination region may be native with the transcriptional initiation region or active variant or fragment thereof, may be native with the plant host, or may be derived from another source (i.e., foreign or heterologous) to the promoter, the ALS polynucleotide or active fragment or variant thereof, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences, which may or may not also contain introns. Such leader sequences can act to enhance translation. Translation leaders are known in the art and include: picornavirus leaders, for example, EMCV leader (Encephalomyocarditis 5' noncoding region) (Elroy Stein et al. (1989) *Proc. Natl. Acad. Sci.* USA 86:6126 6130); potyvirus leaders, for example, TEV leader (Tobacco Etch Virus) (Gallie et al. (1995) *Gene* 165(2):233-238), MDMV leader (Maize Dwarf Mosaic Virus) (Virology 154:9 20), and human immunoglobulin heavy chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622 625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382 385. See also, Della Cioppa et al. (1987) *Plant Physiol.* 84:965 968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used to express the various ALS sequences disclosed herein, including the native promoter of the polynucleotide sequence of interest. The promoters can be selected based on the desired outcome. Such promoters include, for example, constitutive, inducible, tissue-preferred, or other promoters for expression in plants or in any organism of interest.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor.*

Appl. Genet. 81:581-588); MAS (Velten et al. (1984) EMBO J. 3:2723-2730); ALS3 promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced ALS expression within a particular plant tissue. Tissue-preferred promoters include those described in Yamamoto et al. (1997) Plant J. 12(2):255-265; Kawamata et al. (1997) Plant Cell Physiol. 38(7):792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol Biol. 23(6):1129-1138; Matsuoka et al. (1993) Proc Natl. Acad. Sci. USA 90(20):9586-9590; and Guevara-Garcia et al. (1993) Plant J. 4(3):495-505. Such promoters can be modified, if necessary, for weak expression. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat et al. Plant Sci. 47, 95-102 (1986); Reina et al. Nucleic Acids Res. 18 (21), 6426 (1990); and Kloesgen et al., Mol. Gen. Genet. 203, 237-244 (1986). Promoters that express in the embryo, pericarp, and endosperm are disclosed in U.S. Pat. No. 6,225,529; U.S. Pat. No. 6,528,704; and U.S. Pat. No. 6,903,205. The disclosures each of these are incorporated herein by reference in their entirety.

Leaf-preferred promoters are known in the art. See, for example, Yamamoto et al. (1997) Plant J. 12(2):255-265; Kwon et al. (1994) Plant Physiol. 105:357-67; Yamamoto et al. (1994) Plant Cell Physiol. 35(5):773-778; Gotor et al. (1993) Plant J. 3:509-18; Orozco et al. (1993) Plant Mol. Biol. 23(6):1129-1138; and Matsuoka et al. (1993) Proc. Natl. Acad. Sci. USA 90(20):9586-9590.

Synthetic promoters can be used to express ALS sequences or biologically active variants and fragments thereof.

Alternatively, a plant promoter may be under environmental control. Such promoters are referred to here as "inducible" promoters. Examples of environmental conditions that may affect transcription by inducible promoters include pathogen attack, anaerobic conditions, or the presence of light. In particular, examples of inducible promoters are the Adh1 promoter which is inducible by hypoxia or cold stress, the Hsp70 promoter which is inducible by heat stress, and the PPDK promoter which is inducible by light. Also useful are promoters which are chemically inducible. Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners; the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters. See, for example, the glucocorticoid-inducible promoter in Schena et al. (1991) Proc. Natl. Acad. Sci. USA 88:10421-10425 and McNellis et al. (1998) Plant J. 14(2):247-257 and the tetracycline-inducible and tetracycline-repressible promoters for example, Gatz et al. (1991) Mol. Gen. Genet. 227:229-237, and U.S. Pat. Nos. 5,814,618 and 5,789,156, herein incorporated by reference.

In some embodiments, the nucleic acids of interest are targeted to the chloroplast for expression. In this manner, where the nucleic acid of interest is not directly inserted into the chloroplast, the expression cassette will additionally contain a chloroplast-targeting sequence. A "chloroplast transit peptide" is an amino acid sequence which is translated in conjunction with a protein and directs the protein to the chloroplast or other plastid types present in the cell in which the protein is made (Lee et al. (2008) Plant Cell 20:1603-1622). The terms "chloroplast transit peptide" and "plastid transit peptide" are used interchangeably herein. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) Ann. Rev. Plant Phys. Plant Mol. Biol. 42:21 53). Chloroplast targeting sequences and methods for transformation of chloroplasts are known in the art.

For expression in plants, the ALS inhibitor tolerant polypeptides described herein include a native chloroplast transit peptide. However, any chloroplast transit peptide known in the art can be fused to the amino acid sequence of a mature ALS inhibitor tolerant polypeptide of the invention by operably linking a chloroplast-targeting sequence to the 5' end of a nucleotide sequence encoding a mature ALS inhibitor tolerant polypeptide.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, sulfonylureas, dicamba, and 2,4-dichlorophenoxyacetate (2,4-D). Additional selectable markers include phenotypic markers such as β-galactosidase and fluorescent proteins such as green fluorescent protein (GFP) (Su et al. (2004) Biotechnol Bioeng 85:610-9 and Fetter et al. (2004) Plant Cell 16:215-28), cyan florescent protein (CYP) (Bolte et al. (2004) J. Cell Science 117:943-54 and Kato et al. (2002) Plant Physiol 129:913-42), and yellow florescent protein (PhiYFP from Evrogen, see, Bolte et al. (2004) J. Cell Science 117:943-54). For additional selectable markers, see generally, Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschle et al. (1989) Proc. Natl. Acad. Sci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl. Acad. Sci. USA 89:3952-3956; Baim et al. (1991) Proc. Natl. Acad. Sci. USA 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) *Ph.D. Thesis*, University of Heidelberg; Gossen et al. (1992) Proc. Natl. Acad. Sci. USA 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) Nature 334:721-724. Such disclosures are herein incorporated by reference. The above list of selectable marker genes is not meant to be limiting. Any selectable marker gene can be used in the present invention, including for example, DsRed.

In another aspect, the ALS inhibitor-tolerant sequence disclosed herein or active variants or fragments thereof can also be used as a selectable marker gene. In this embodiment, the presence of the ALS polynucleotide in a cell or organism confers upon the cell or organism the detectable phenotypic trait of ALS inhibitor tolerance, thereby allowing one to select for cells or organisms that have been transformed with a gene of interest linked to the ALS polynucleotide. Thus, for example, the ALS polynucleotide can be introduced into a nucleic acid construct, e.g., a vector, thereby allowing for the identification of a host (e.g., a cell or transgenic plant) containing the nucleic acid construct by growing the host in the presence of an ALS inhibitor (e.g. chlorsulfuron) and selecting for the ability to survive and/or grow at a rate that is discernibly greater than a host lacking the nucleic acid construct would survive or grow. An ALS polynucleotide can be used as a selectable marker in a wide variety of hosts that are sensitive to ALS inhibitors, including plants, most bacteria (including *E. coli*), actinomycetes, yeasts, algae and fungi. One benefit of using herbicide resistance as a marker in plants, as opposed to conventional antibiotic resistance, is that it obviates the concern of some members of the public that antibiotic resistance might escape into the environment.

In bacterial systems, a number of expression vectors may be selected depending upon the use intended for the ALS polypeptide. For example, when large quantities of ALS polypeptides or fragments thereof are needed for commercial production or for induction of antibodies, vectors which direct high level expression of fusion proteins that are readily purified can be desirable. Such vectors include, but are not limited to, multifunctional *E. coli* cloning and expression vectors such as BLUESCRIPT (Stratagene), in which the ALS polypeptide coding sequence may be ligated into the vector in-frame with sequences for the amino-terminal Met and the subsequent 7 residues of beta-galactosidase so that a hybrid protein is produced; pIN vectors (Van Heeke & Schuster (1989) *J Biol Chem* 264:5503-5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the ALS polypeptides of the invention. For reviews, see Ausubel (supra) and Grant et al. (1987) *Methods in Enzymology* 153:516-544. In mammalian host cells, a variety of expression systems, including viral-based systems, may be utilized. In cases where an adenovirus is used as an expression vector, a coding sequence, e.g., of an ALS polypeptide, is optionally ligated into an adenovirus transcription/translation complex consisting of the late promoter and tripartite leader sequence. Insertion of an ALS polypeptide coding region into a nonessential E1 or E3 region of the viral genome will result in a viable virus capable of expressing an ALS in infected host cells (Logan and Shenk (1984) *Proc Natl Acad Sci* USA 81:3655-3659). In addition, transcription enhancers, such as the rous sarcoma virus (RSV) enhancer, may be used to increase expression in mammalian host cells.

F. Stacking Other Traits of Interest

In some embodiments, the ALS polynucleotides or active variants and fragments thereof disclosed herein are engineered into a molecular stack. Thus, the various host cells, plants, plant cells and seeds disclosed herein can further comprise one or more traits of interest, and in more some embodiments, the host cell, plant, plant part or plant cell is stacked with any combination of polynucleotide sequences of interest in order to create plants with a desired combination of traits. As used herein, the term "stacked" includes having the multiple traits present in the same plant or organism of interest. In one non-limiting example, "stacked traits" comprise a molecular stack where the sequences are physically adjacent to each other. A trait, as used herein, refers to the phenotype derived from a particular sequence or groups of sequences. In one embodiment, the molecular stack comprises at least one additional polynucleotide that also confers tolerance to at least one sequence that confers tolerance to one or more ALS inhibitors by the same and/or different mechanism and/or at least one additional polynucleotide that confers tolerance to a second herbicide.

Thus, in one embodiment, the host cell, plant, plant cell or plant part having the ALS inhibitor-tolerant polynucleotides or active variants or fragments thereof is stacked with at least one other ALS sequence that confers tolerance to at least one other ALS inhibitor. A variety of ALS inhibitors are known and include, for example, sulfonylurea, imidazolinone, triazolopyrimidines, pryimidinyoxy(thio)benzoates, and/or sulfonylaminocarbonyltriazolinone herbicides. Additional ALS inhibitors are known and are disclosed elsewhere herein. It is known in the art that ALS mutations fall into different classes with regard to tolerance to sulfonylureas, imidazolinones, triazolopyrimidines, and pyrimidinyl(thio) benzoates, including mutations having the following characteristics: (1) broad tolerance to all four of these groups; (2) tolerance to imidazolinones and pyrimidinyl(thio)benzoates; (3) tolerance to sulfonylureas and triazolopyrimidines; and (4) tolerance to sulfonylureas and imidazolinones.

In some embodiments, the host cells, plants or plant cells having the ALS inhibitor-tolerant polynucleotides or active variants or fragments thereof may be stacked with other herbicide-tolerance traits to create a transgenic plant of the invention with further properties.

For example, the plant or plant cell or plant part having an ALS inhibitor-tolerant sequence or an active variant or fragment thereof may be stacked with, for example, a sequence which confers tolerance to glyphosate. Tolerance to glyphosate can occur via the expression of glyphosate acetyltransferase (GLYAT) (for example, as described in U.S. Pat. Nos. 7,462,481; 7,531,339; 7,714,188; 7,709,702; 7,666,643; 7,527,955; 8,008,547; 8,088,972; 7,998,703; 7,999,152; 8,021,857; 8,044,261; 7,405,074; 7,666,644; and 7,863,503) or a sequence that encodes a glyphosate oxidoreductase enzyme as described more fully in U.S. Pat. Nos. 5,776,760 and 5,463,175, each of which is incorporated by reference. Other traits include polynucleotides that confer on the plant the capacity to produce a higher level or glyphosate insensitive 5-enolpyruvylshikimate-3-phosphate synthase (EPSPS), for example, as more fully described in U.S. Pat. Nos. 6,248,876 B1; 5,627,061; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769, 061; 5,633,448; 5,510,471; Re. 36,449; RE 37,287 E; and 5,491,288; and international publications WO 97/04103; WO 00/66746; WO 01/66704; and WO 00/66747.

In other embodiments, plants, plant cells, explants and expression cassettes comprising the ALS inhibitor-tolerant sequences or active variants or fragments thereof are stacked with a sequence that confers tolerance to an HPPD inhibitor. For example, a P450 sequence could be employed which provides tolerance to HPPD-inhibitors by metabolism of the herbicide. Such sequences include, but are not limited to, the NSF1 gene. See, US 2007/0214515 and US 2008/0052797, both of which are herein incorporated by reference in their entirety.

In other embodiments, the plants, plant cells, explants and expression cassettes can comprise an ALS inhibitor-tolerant sequence or an active variant or fragment thereof stacked with an HPPD sequence or variants and fragments thereof which confer tolerance to an HPPD inhibitor. See, for example, US Publication Nos. US20120042413; US20090055976; and US20110023180; U.S. Pat. Nos. 6,245,968 B1; 6,268,549; 6,069,115; 6,245,968; 6,268,549; and 7,935,869; and international publication WO 99/23886; each of which is herein incorporated by reference.

In still other embodiments, the plant or plant cell or plant part having the ALS inhibitor-tolerant sequences or active variants or fragments thereof may be stacked with, for example, aryloxyalkanoate dioxygenase polynucleotides (which confer tolerance to 2,4-D and other phenoxy auxin herbicides as well as to aryloxyphenoxypropionate herbicides as described, for example, in WO2005/107437); dicamba-tolerance polynucleotides (as described, for example, in Herman et al. (2005) *J. Biol. Chem.* 280: 24759-24767); auxin polypeptides and an acetyl coenzyme A carboxylase (ACCase) polypeptides (as described for example in US Patent Publication US20120042412); dicamba monooxygenases (as described for example in U.S. Pat. No. 7,022,896 and WO2007146706A2); polynucleotide molecules encoding AAD-12 (as described for example in U.S. Pat. No. 8,283,522 or WO2007053482A2); polynucleotides encoding AAD-1 (as described for example in US Patent Application Publication Number 2011/0124503A1 or U.S. Pat. No. 7,838,733); and/or polynucleotides that inhibit expression of auxin receptors such as e.g. AFB5, AFB4, and SGT1b (see U.S. Pat. No. 8,088,979).

In still other embodiments, the plant or plant cell or plant part having the ALS inhibitor-tolerant sequences or active variants or fragments thereof may be stacked with polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616; and 5,879,903. Glutamine synthetase (GS) appears to be an essential enzyme necessary for the development and life of most plant cells. Inhibitors of GS are toxic to plant cells. Glufosinate herbicides have been developed based on the toxic effect due to the inhibition of GS in plants. These herbicides are non-selective. They inhibit growth of all the different species of plants present, causing their total destruction. However, plants containing an exogenous phosphinothricin acetyltransferase can exhibit improved tolerance to glufosinate herbicides, which inhibit the enzyme glutamine synthase. The development of plants containing an exogenous phosphinothricin acetyl transferase is described in U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference in their entireties for all purposes.

Other examples of herbicide-tolerance traits that could be combined with the plants or plant cell or plant part having the ALS inhibitor-tolerant sequence or an active variant or fragment thereof include those conferred by polynucleotides conferring altered protoporphyrinogen oxidase (protox) activity, as described in U.S. Pat. Nos. 6,288,306 B1; 6,282,837 B1; and 5,767,373; and international publication WO 01/12825. Plants containing such polynucleotides can exhibit improved tolerance to any of a variety of herbicides which target the protox enzyme (also referred to as "protox inhibitors").

Other examples of herbicide-tolerance traits that could be combined with the plants or plant cell or plant part having the ALS inhibitor-tolerant sequence or an active variant or fragment thereof include those conferring tolerance to at least one herbicide in a plant such as, for example, a maize plant or horseweed. Herbicide-tolerant weeds are known in the art, as are plants that vary in their tolerance to particular herbicides. See, e.g., Green and Williams (2004) "*Correlation of Corn (Zea mays) Inbred Response to Nicosulfuron and Mesotrione,*" poster presented at the WSSA Annual Meeting in Kansas City, Mo., Feb. 9-12, 2004; Green (1998) *Weed Technology* 12: 474-477; Green and Ulrich (1993) *Weed Science* 41: 508-516. The trait(s) responsible for these tolerances can be combined by breeding or via other methods with the plants or plant cell or plant part having the ALS inhibitor-tolerant sequence or an active variant or fragment thereof to provide a plant of the invention as well as methods of use thereof.

In still further embodiments, the ALS inhibitor-tolerant sequences can be stacked with at least one polynucleotide encoding a homogentisate solanesyltransferase (HST). See, for example, WO2010023911 herein incorporated by reference in its entirety. In such embodiments, classes of herbicidal compounds—which act wholly or in part by inhibiting HST can be applied over the plants having the HTS polypeptide.

The plant or plant cell or plant part having the ALS inhibitor-tolerant sequence or an active variant or fragment thereof can also be combined with at least one other trait to produce plants that further comprise a variety of desired trait combinations including, but not limited to, traits desirable for animal feed such as high oil content (e.g., U.S. Pat. No. 6,232,529); balanced amino acid content (e.g., hordothionins (U.S. Pat. Nos. 5,990,389; 5,885,801; 5,885,802; and 5,703,409; U.S. Pat. No. 5,850,016); barley high lysine (Williamson et al. (1987) *Eur. J. Biochem.* 165: 99-106; and WO 98/20122) and high methionine proteins (Pedersen et al. (1986) *J. Biol. Chem.* 261: 6279; Kirihara et al. (1988) *Gene* 71: 359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005, 429, filed Dec. 3, 2001)); the disclosures of which are herein incorporated by reference. Desired trait combinations also include LLNC (low linolenic acid content; see, e.g., Dyer et al. (2002) *Appl. Microbiol. Biotechnol.* 59: 224-230) and OLCH (high oleic acid content; see, e.g., Fernandez-Moya et al. (2005) *J. Agric. Food Chem.* 53: 5326-5330).

The plant or plant cell or plant part having the ALS inhibitor-tolerant sequence or an active variant or fragment thereof can also be combined with other desirable traits such as, for example, fumonisin detoxification genes (U.S. Pat. No. 5,792,931), avirulence and disease resistance genes (Jones et al. (1994) *Science* 266: 789; Martin et al. (1993) *Science* 262: 1432; Mindrinos et al. (1994) *Cell* 78: 1089), and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine herbicide-tolerant polynucleotides with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

In other embodiments, the plant or plant cell or plant part having the ALS inhibitor-tolerant sequence or an active variant or fragment thereof may be stacked with any other polynucleotides encoding polypeptides having pesticidal and/or insecticidal activity, such as *Bacillus thuringiensis* toxic proteins (described in U.S. Pat. Nos. 5,366,892; 5,747, 450; 5,737,514; 5,723,756; 5,593,881; Geiser et al. (1986) *Gene* 48: 109; Lee et al. (2003) *Appl. Environ. Microbiol.* 69: 4648-4657 (Vip3A); Galitzky et al. (2001) *Acta Crystallogr. D. Biol. Crystallogr.* 57: 1101-1109 (Cry3Bb1); and Herman et al. (2004) *J. Agric. Food Chem.* 52: 2726-2734 (Cry1 F)), lectins (Van Damme et al. (1994) *Plant Mol. Biol.* 24: 825, pentin (described in U.S. Pat. No. 5,981,722), and the like. The combinations generated can also include multiple copies of any one of the polynucleotides of interest.

In another embodiment, the plant or plant cell or plant part having the ALS inhibitor-tolerant sequence or an active variant or fragment thereof can also be combined with the Rcg1 sequence or biologically active variant or fragment thereof. The Rcg1 sequence is an anthracnose stalk rot resistance gene in corn. See, for example, U.S. patent application Ser. Nos. 11/397,153, 11/397,275, and 11/397, 247, each of which is herein incorporated by reference.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Any plant having an ALS inhibitor-tolerant sequence disclosed herein or an active variant or fragment thereof can be used to make a food or a feed product. Such methods comprise obtaining a plant, explant, seed, plant cell, or cell comprising the ALS inhibitor-tolerant sequence or active variant or fragment thereof and processing the plant, explant, seed, plant cell, or cell to produce a food or feed product.

G. Method of Introducing

Various methods can be used to introduce a sequence of interest into a host cell, plant or plant part. "Introducing" is intended to mean presenting to the host cell, plant, plant cell or plant part the polynucleotide or polypeptide in such a manner that the sequence gains access to the interior of a cell of the plant or organism. The methods of the invention do not depend on a particular method for introducing a sequence into an organism or a plant or plant part, only that the polynucleotide or polypeptides gains access to the interior of at least one cell of the organism or the plant. Methods for introducing polynucleotide or polypeptides into various organisms, including plants, are known in the art including, but not limited to, stable transformation methods, transient transformation methods, and virus-mediated methods.

"Stable transformation" is intended to mean that the nucleotide construct introduced into a plant integrates into the genome of the plant or organism of interest and is capable of being inherited by the progeny thereof. "Transient transformation" is intended to mean that a polynucleotide is introduced into the plant or organism of interest and does not integrate into the genome of the plant or organism or a polypeptide is introduced into a plant or organism.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320 334), electroporation (Riggs et al. (1986) *Proc. Natl. Acad. Sci. USA* 83:5602 5606, *Agrobacterium*-mediated transformation (U.S. Pat. No. 5,563, 055 and U.S. Pat. No. 5,981,840), direct gene transfer (Paszkowski et al. (1984) *EMBO J.* 3:2717 2722), and ballistic particle acceleration (see, for example, U.S. Pat. No. 4,945,050; U.S. Pat. No. 5,879,918; U.S. Pat. Nos. 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923 926); and Led transformation (WO 00/28058). Also see Weissinger et al. (1988) *Ann. Rev. Genet.* 22:421 477; Sanford et al. (1987) *Particulate Science and Technology* 5:27 37 (onion); Christou et al. (1988) *Plant Physiol.* 87:671 674 (soybean); McCabe et al. (1988) *Bio/Technology* 6:923 926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736 740 (rice); Klein et al. (1988) *Proc. Natl. Acad. Sci. USA* 85:4305 4309 (maize); Klein et al. (1988) *Biotechnology* 6:559 563 (maize); U.S. Pat. Nos. 5,240,855; 5,322,783; and, 5,324, 646; Klein et al. (1988) *Plant Physiol.* 91:440 444 (maize); Fromm et al. (1990) *Biotechnology* 8:833 839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); Cardoza and Steward (2006) *Methods Mol. Biol.* 343:257-66 (canola via *Agrobacterium tumefaciens*); Shrawat and Lorz (2006) *Plant Biotechnol J.* 4:575-603 (Agrobacterium-mediated transformation in cereals); Datta and Datta (2006) *Methods Mol Biol* 343:201-12 (rice); Bhalla (2006) *Trends Biotechnol.* 24:305-11 (wheat); all of which are herein incorporated by reference.

In some embodiments, the ALS inhibitor-tolerant sequences or active variants or fragments thereof can be provided to a plant using a variety of transient transformation methods. Such transient transformation methods include, but are not limited to, the introduction of the ALS inhibitor-tolerant protein or active variants and fragments thereof directly into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference.

In other embodiments, the ALS inhibitor-tolerant polynucleotide disclosed herein or active variants and fragments thereof may be introduced into plants by contacting plants with a virus or viral nucleic acids. Generally, such methods involve incorporating a nucleotide construct of the invention within a DNA or RNA molecule. It is recognized that the ALS inhibitor-tolerant sequence may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome. Other methods to target polynucleotides are set forth in WO 2009/114321 (herein incorporated by reference), which describes "custom" meganucleases produced to modify plant genomes, in particular the genome of maize. See, also, Gao et al. (2010) *Plant Journal* 1:176-187. Another site-directed engineering is through the use of zinc finger domain recognition coupled with the restriction properties of restriction enzyme. See e.g., Urnov, et al., (2010) *Nat Rev Genet.* 11(9):636-46; Shukla, et al., (2009) *Nature* 459 (7245):437-41. The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

Transformed plant cells which are derived by plant transformation techniques, including those discussed above, can be cultured to regenerate a whole plant which possesses the transformed genotype (i.e., an ALS inhibitor-tolerant polynucleotide), and thus the desired phenotype, such as acquired resistance (i.e., tolerance) to at least one ALS inhibitor. For transformation and regeneration of maize see, Gordon-Kamm et al., *The Plant Cell*, 2:603-618 (1990). Plant regeneration from cultured protoplasts is described in Evans et al. (1983) *Protoplasts Isolation and Culture*, Handbook of Plant Cell Culture, pp 124-176, Macmillan Publishing Company, New York; and Binding (1985) *Regeneration of Plants, Plant Protoplasts* pp 21-73, CRC Press, Boca Raton. Regeneration can also be obtained from plant callus, explants, organs, or parts thereof. Such regeneration techniques are described generally in Klee et al. (1987) *Ann Rev of Plant Phys* 38:467. See also, e.g., Payne and Gamborg.

One of skill will recognize that after the expression cassette containing the ALS inhibitor-tolerant gene is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the ALS inhibitor-tolerant nucleic acid. Progeny and variants, and mutants of the regenerated plants are also included within the scope of the invention, provided that these parts comprise the introduced nucleic acid sequences.

In one embodiment, a homozygous transgenic plant can be obtained by sexually mating (selfing) a heterozygous transgenic plant that contains a single added nucleic acid, germinating some of the seed produced and analyzing the resulting plants produced for altered cell division relative to a control plant (i.e., native, non-transgenic). Back-crossing to a parental plant and out-crossing with a non-transgenic plant are also contemplated.

Animal and lower eukaryotic (e.g., yeast) host cells are competent or rendered competent for transfection by various means. There are several well-known methods of introducing DNA into animal cells. These methods include: calcium phosphate precipitation; fusion of the recipient cells with bacterial protoplasts containing the DNA; treatment of the recipient cells with liposomes containing the DNA; DEAE dextran; electroporation; biolistics; and micro-injection of the DNA directly into the cells. The transfected cells are cultured by means well known in the art. See, Kuchler, R. J., *Biochemical Methods in Cell Culture and Virology*, Dowden, Hutchinson and Ross, Inc. (1977).

II. Methods of Use

A. Methods for Producing ALS Inhibitor-Tolerant Plants that Produce Seeds with Wild-Type Levels of C17 Fatty Acids Methods for producing ALS inhibitor-tolerant plants that produce seeds with wild type levels of C17 fatty acids are provided. In these methods, the ALS-inhibitor tolerant polypeptide or the ALS inhibitor-tolerant polynucleotide or active variant or fragment thereof is introduced into the plant, plant cell, explant or plant part. The method may further include regenerating a transgenic plant from a plant cell transformed with the ALS-inhibitor tolerant polypeptide or the ALS inhibitor-tolerant polynucleotide or active variant or fragment thereof, and the polynucleotide may be stably integrated into the genome of the plant cell. Also of interest are transgenic plants produced by these methods and seeds produced by the transgenic plants. The seeds may have less than 0.5%, 0.45%, 0.40%, 0.35%, 0.30%, 0.25%, 0.20%, 0.15%, 0.10%, or less C17 fatty acids relative to total fatty acids.

B. Methods of Producing Crops and Controlling Weeds

Methods for controlling weeds in an area of cultivation, preventing the development or the appearance of herbicide resistant weeds in an area of cultivation, producing a crop, and increasing crop safety are provided. The term "controlling," and derivations thereof, for example, as in "controlling weeds" refers to one or more of inhibiting the growth, germination, reproduction, and/or proliferation of; and/or killing, removing, destroying, or otherwise diminishing the occurrence and/or activity of a weed.

As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

As used herein, by "selectively controlled" it is intended that the majority of weeds in an area of cultivation are significantly damaged or killed, while if crop plants are also present in the field, the majority of the crop plants are not significantly damaged. Thus, a method is considered to selectively control weeds when at least 55%, 60%, 65%, 70%, 75%, 80%, 85%, 90%, 95%, or more of the weeds are significantly damaged or killed, while if crop plants are also present in the field, less than 45%, 40%, 35%, 30%, 25%, 20%, 15%, 10%, 5%, or 1% of the crop plants are significantly damaged or killed.

Methods provided comprise planting the area of cultivation with a plant having an ALS inhibitor-tolerant sequence or active variant or fragment thereof disclosed herein or transgenic seed derived therefrom, and in some embodiments, applying to the plant, seed, weed or area of cultivation thereof an effective amount of an ALS inhibitor. It is recognized that the ALS inhibitor can be applied before or after the plants are planted in the area of cultivation.

An "ALS inhibitor" may include, but is not limited to, sulfonylurea, imidazolinone, triazolopyrimidines, pyrimidinyloxy(thio)benzoates, and/or sulfonylamino-carbonyl-triazonline herbicide.

Generally, the effective amount of herbicide applied to the field is sufficient to selectively control the weeds without significantly affecting the crop. It is important to note that it is not necessary for the crop to be totally insensitive to the herbicide, so long as the benefit derived from the inhibition of weeds outweighs any negative impact of the ALS inhibitor on the crop or crop plant.

"Weed" as used herein refers to a plant which is not desirable in a particular area. Conversely, a "crop plant" as used herein refers to a plant which is desired in a particular area, such as, for example, a maize or soy plant. Thus, in some embodiments, a weed is a non-crop plant or a non-crop species, while in some embodiments, a weed is a crop species which is sought to be eliminated from a particular area, such as, for example, an inferior and/or non-transgenic soy plant in a field planted with a plant having the ALS inhibitor-tolerant sequence disclosed herein or an active variant or fragment thereof.

Accordingly, the invention provides methods for selectively controlling weeds in a field containing a crop that involve planting the field with crop seeds or plants which are tolerant to at least one ALS inhibitor as a result of being transformed with a gene encoding an ALS inhibitor-tolerant polypeptide disclosed herein or an active variant or fragment thereof, and applying to the crop and weeds in the field a sufficient amount of an ALS inhibitor to control the weeds without significantly affecting the crop.

Further provided are methods for controlling weeds in a field and preventing the emergence of ALS inhibitor resistant weeds in a field containing a crop which involve planting the field with crop seeds or plants that are tolerant to an ALS inhibitor as a result of being transformed with a gene encoding an ALS inhibitor-tolerant polypeptide and applying to the crop and the weeds in the field a sufficient amount of an ALS inhibitor to control the weeds without significantly affecting the crop. Various plants that can be used in this method are discussed in detail elsewhere herein.

In further embodiments, the invention provides methods for controlling weeds in a field and preventing the emergence of herbicide resistant weeds in a field containing a crop which involve planting the field with crop seeds or plants that are tolerant to an ALS inhibitor as a result of being transformed with a gene encoding an ALS inhibitor-tolerant polypeptide and that have a gene encoding a polypeptide imparting tolerance to an additional herbicide, such as, a gene encoding a polypeptide imparting glyphosate tolerance e.g. a glyphosate acetyltransferase, a glyphosate-tolerant 5-enolpyruvylshikimate-3-phosphate synthase and/or a glyphosate-tolerant glyphosate oxido-reductase; a mutated hydroxyphenylpyruvatedioxygenase; a phosphinothricin acetyl transferase and a mutated protoporphyrinogen oxidase and applying to the crop and the weeds in the field a sufficient amount of an ALS inhibitor and an additional herbicide, such as, glyphosate, a hydroxyphenylpyruvatedioxygenase inhibitor, bialaphos, phosphinothricin, azafenidin, butafenacil, sulfosate, glufosinate, and a protox inhibitor to control the weeds without significantly affecting the crop. Various plants and seeds that can be used in this method are discussed in detail elsewhere herein.

Further provided are methods for controlling weeds in a field and preventing the emergence of herbicide resistant weeds in a field containing a crop which involve planting the field with crop seeds or plants that are tolerant to an ALS inhibitor as a result of being transformed with a gene encoding an ALS inhibitor tolerant polypeptide and a gene encoding a polypeptide imparting tolerance to an additional herbicide, such as, glyphosate, a mutated hydroxyphenylpyruvatedioxygenase, a phosphinothricin acetyl transferase and a mutated protoporphyrinogen oxidase and applying to the crop and the weeds in the field a sufficient amount of an ALS inhibitor and an additional herbicide, such as, glyphosate, a hydroxyphenylpyruvatedioxygenase inhibitor, bialaphos, phosphinothricin, azafenidin, butafenacil, sulfosate, glufosinate, and a protox inhibitor to control the weeds without significantly affecting the crop. Various plants and seeds that can be used in this method are discussed in detail elsewhere herein.

Further provided is a method for producing a crop by growing a crop plant that is tolerant to an ALS inhibitor as a result of being transformed with an ALS inhibitor tolerant polynucleotide or active variant or fragment thereof disclosed herein, under conditions such that the crop plant produces a crop, and harvesting the crop. Preferably, the ALS inhibitor is applied to the plant, or in the vicinity of the plant, at a concentration effective to control weeds without preventing the transgenic crop plant from growing and producing the crop. The application of the ALS inhibitor can be before planting, or at any time after planting up to and including the time of harvest. The ALS inhibitor can be applied once or multiple times. The timing of application, amount applied, mode of application, and other parameters will vary based upon the specific nature of the crop plant and the growing environment, and can be readily determined by one of skill in the art. The invention further provides the crop produced by this method.

Further provided are methods for the propagation of a plant containing an ALS inhibitor tolerant polypeptide or active variant or fragment thereof. The plant can be, for example, a monocot or a dicot. In one aspect, propagation entails crossing a plant containing an ALS inhibitor tolerant polynucleotide transgene with a second plant, such that at least some progeny of the cross display tolerance to at least one ALS inhibitor.

The methods of the invention further allow for the development of herbicide applications to be used with the plants having an ALS inhibitor tolerant sequence or active variants or fragments thereof. In such methods, the environmental conditions in an area of cultivation are evaluated. Environmental conditions that can be evaluated include, but are not limited to, ground and surface water pollution concerns, intended use of the crop, crop tolerance, soil residuals, weeds present in area of cultivation, soil texture, pH of soil, amount of organic matter in soil, application equipment, and tillage practices. Upon the evaluation of the environmental conditions, an effective amount of a combination of herbicides can be applied to the crop, crop part, and seed of the crop or area of cultivation.

Any herbicide or combination of herbicides can be applied to the plant having an ALS inhibitor tolerant sequence or active variant or fragment thereof disclosed herein or transgenic seed derived there from, crop part, or the area of cultivation containing the crop plant. By "treated with a combination of" or "applying a combination of herbicides to a crop, area of cultivation or field" it is intended that a particular field, crop or weed is treated with each of the herbicides and/or chemicals indicated to be part of the combination so that a desired effect is achieved, i.e., so that weeds are selectively controlled while the crop is not significantly damaged. The application of each herbicide and/or chemical may be simultaneous or the applications may be at different times (sequential), so long as the desired effect is achieved. Furthermore, the application can occur prior to the planting of the crop.

Classifications of herbicides (i.e., the grouping of herbicides into classes and subclasses) are well-known in the art and include classifications by HRAC (Herbicide Resistance Action Committee) and WSSA (the Weed Science Society of America) (see also, Retzinger and Mallory-Smith (1997) *Weed Technology* 11: 384-393). An abbreviated version of the HRAC classification (with notes regarding the corresponding WSSA group) is set forth below in Table 1.

Herbicides can be classified by their mode of action and/or site of action and can also be classified by the time at which they are applied (e.g., preemergent or postemergent), by the method of application (e.g., foliar application or soil application), or by how they are taken up by or affect the plant or by their structure. "Mode of action" generally refers to the metabolic or physiological process within the plant that the herbicide inhibits or otherwise impairs, whereas "site of action" generally refers to the physical location or biochemical site within the plant where the herbicide acts or directly interacts. Herbicides can be classified in various ways, including by mode of action and/or site of action (see, e.g., Table 1).

Often, a herbicide-tolerance gene that confers tolerance to a particular herbicide or other chemical on a plant expressing it will also confer tolerance to other herbicides or chemicals in the same class or subclass, for example, a class or subclass set forth in Table 1. Thus, in some embodiments, a transgenic plant is tolerant to more than one herbicide or chemical in the same class or subclass, such as, for example, an HPPD inhibitor, glyphosate, an ALS chemistry, an inhibitor of PPO, a sulfonylurea, and/or a synthetic auxin.

Typically, the plants of the present invention can tolerate treatment with different types of herbicides (i.e., herbicides having different modes of action and/or different sites of action) thereby permitting improved weed management strategies that are recommended in order to reduce the incidence and prevalence of herbicide-tolerant weeds.

TABLE 1

Abbreviated version of HRAC Herbicide Classification

I. ALS Inhibitors (WSSA Group 2)
   A. Sulfonylureas
      1. Azimsulfuron
      2. Chlorimuron-ethyl
      3. Metsulfuron-methyl
      4. Nicosulfuron
      5. Rimsulfuron
      6. Sulfometuron-methyl
      7. Thifensulfuron-methyl
      8. Tribenuron-methyl
      9. Amidosulfuron
     10. Bensulfuron-methyl
     11. Chlorsulfuron
     12. Cinosulfuron
     13. Cyclosulfamuron
     14. Ethametsulfuron-methyl
     15. Ethoxysulfuron
     16. Flazasulfuron
     17. Flupyrsulfuron-methyl
     18. Foramsulfuron
     19. Imazosulfuron
     20. Iodosulfuron-methyl
     21. Mesosulfuron-methyl
     22. Oxasulfuron
     23. Primisulfuron-methyl
     24. Prosulfuron
     25. Pyrazosulfuron-ethyl
     26. Sulfosulfuron TABLE 1-continued Abbreviated version of HRAC Herbicide Classification 27. Triasulfuron
28. Trifloxysulfuron
29. Triflusulfuron-methyl
30. Tritosulfuron
31. Halosulfuron-methyl
32. Flucetosulfuron
B. Sulfonylaminocarbonyltriazolinones
 1. Flucarbazone
 2. Procarbazone
C. Triazolopyrimidines
 1. Cloransulam-methyl
 2. Flumetsulam
 3. Diclosulam
 4. Florasulam
 5. Metosulam
 6. Penoxsulam
 7. Pyroxsulam
D. Pyrimidinyloxy(thio)benzoates
 1. Bispyribac
 2. Pyriftalid
 3. Pyribenzoxim
 4. Pyrithiobac
 5. Pyriminobac-methyl
E. Imidazolinones
 1. Imazapyr
 2. Imazethapyr
 3. Imazaquin
 4. Imazapic
 5. Imazamethabenz-methyl
 6. Imazamox
II. Other Herbicides - Active Ingredients/Additional Modes of Action
 A. Inhibitors of Acetyl CoA carboxylase (ACCase) (WSSA Group 1)
  1. Aryloxyphenoxypropionates ('FOPs')
   a. Quizalofop-P-ethyl
   b. Diclofop-methyl
   c. Clodinafop-propargyl
   d. Fenoxaprop-P-ethyl
   e. Fluazifop-P-butyl
   f. Propaquizafop
   g. Haloxyfop-P-methyl
   h. Cyhalofop-butyl
   i. Quizalofop-P-ethyl
  2. Cyclohexanediones ('DIMs')
   a. Alloxydim
   b. Butroxydim
   c. Clethodim
   d. Cycloxydim
   e. Sethoxydim
   f. Tepraloxydim
   g. Tralkoxydim
 B. Inhibitors of Photosystem II - HRAC Group C1/WSSA Group 5
  1. Triazines
   a. Ametryne
   b. Atrazine
   c. Cyanazine
   d. Desmetryne
   e. Dimethametryne
   f. Prometon
   g. Prometryne
   h. Propazine
   i. Simazine
   j. Simetryne
   k. Terbumeton
   l. Terbuthylazine
   m. Terbutryne
   n. Trietazine
  2. Triazinones
   a. Hexazinone
   b. Metribuzin
   c. Metamitron TABLE 1-continued Abbreviated version of HRAC Herbicide Classification 3. Triazolinone
   a. Amicarbazone
  4. Uracils
   a. Bromacil
   b. Lenacil
   c. Terbacil
  5. Pyridazinones
   a. Pyrazon
  6. Phenyl carbamates
   a. Desmedipham
   b. Phenmedipham
 C. Inhibitors of Photosystem II - HRAC Group C2/WSSA Group 7
  1. Ureas
   a. Fluometuron
   b. Linuron
   c. Chlorobromuron
   d. Chlorotoluron
   e. Chloroxuron
   f. Dimefuron
   g. Diuron
   h. Ethidimuron
   i. Fenuron
   j. Isoproturon
   k. Isouron
   l. Methabenzthiazuron
   m. Metobromuron
   n. Metoxuron
   o. Monolinuron
   p. Neburon
   q. Siduron
   r. Tebuthiuron
  2. Amides
   a. Propanil
   b. Pentanochlor
 D. Inhibitors of Photosystem II - HRAC Group C3/WSSA Group 6
  1. Nitriles
   a. Bromofenoxim
   b. Bromoxynil
   c. Ioxynil
  2. Benzothiadiazinone (Bentazon)
   a. Bentazon
  3. Phenylpyridazines
   a. Pyridate
   b. Pyridafol
 E. Photosystem-I-electron diversion (Bipyridyliums) (WSSA Group 22)
  1. Diquat
  2. Paraquat In still further methods, an ALS inhibitor can be applied alone or in combination with another herbicide of interest and can be applied to the plants having an ALS inhibitor tolerant sequence as disclosed herein or the area of cultivation.

Additional herbicide treatment that can be applied over the plant or seeds having an ALS inhibitor tolerant polypeptides or active variants and fragments thereof include, but are not limited to: acetochlor, acifluorfen and its sodium salt, aclonifen, acrolein (2 propenal), alachlor, alloxydim, ametryn, amicarbazone, amidosulfuron, aminopyralid, amitrole, ammonium sulfamate, anilofos, asulam, atrazine, azimsulfuron, beflubutamid, benazolin, benazolin ethyl, bencarbazone, benfluralin, benfuresate, bensulfuron methyl, bensulide, bentazone, benzobicyclon, benzofenap, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone ethyl, catechin, chlomethoxyfen, chloramben, chlorbromuron, chlorflurenol-methyl, chloridazon, chlorimuron ethyl, chlorotoluron, chlorpropham, chlorsulfuron, chlorthal dimethyl, chlorthiamid, cinidon-ethyl, cinmethylin, cinosulfuron, clethodim, clodinafop-propargyl, clomazone, clomeprop, clopyralid, clopyralid olamine, cloransulam-methyl, CUH-35 (2 methoxyethyl 2-[[[4-chloro-2-fluoro-5 [(1-methyl-2-propynyl)¬ oxy]¬ phenyl](3-fluoro¬ benzoyl)¬ amino]carbonyl]-1-cyclohexene-1 carboxylate), cumyluron, cyanazine, cycloate, cyclosulfamuron, cycloxydim, cyhalofop-butyl, 2,4 D and its butotyl, butyl, isoctyl and isopropyl esters and its dimethylammonium, diolamine and trolamine salts, daimuron, dalapon, dalapon sodium, dazomet, 2,4 DB and its dimethylammonium, potassium and sodium salts, desmedipham, desmetryn, dicamba and its diglycolammonium, dimethylammonium, potassium and sodium salts, dichlobenil, dichlorprop, diclofop methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron methyl, ethofumesate, ethoxyfen, ethoxysulfuron, etobenzanid, fenoxaprop ethyl, fenoxaprop P-ethyl, fentrazamide, fenuron, fenuron TCA, flamprop methyl, flamprop M isopropyl, flamprop M methyl, flazasulfuron, florasulam, fluazifop butyl, fluazifop P butyl, flucarbazone, flucetosulfuron, fluchloralin, flufenacet, flufenpyr, flufenpyr-ethyl, flumetsulam, flumiclorac pentyl, flumioxazin, fluometuron, fluoroglycofen ethyl, flupyrsulfuron methyl and its sodium salt, flurenol, flurenol-butyl, fluridone, fluorochloridone, fluoroxypyr, flurtamone, fluthiacet methyl, fomesafen, foramsulfuron, fosamine ammonium, glufosinate, glufosinate ammonium, glyphosate and its salts such as ammonium, isopropylammonium, potassium, sodium (including sesquisodium) and trimesium (alternatively named sulfosate) (See, WO2007/024782, herein incorporated by reference), halosulfuron methyl, haloxyfop etotyl, haloxyfop-methyl, hexazinone, HOK-201 (N (2,4-difluorophenyl)-1,5-dihydro-N (1 methylethyl)-5-oxo-1-[(tetrahydro-2H-pyran-2 yl)-methyl]-4H-1,2,4-triazole-4 carboxamide), imazamethabenz methyl, imazamox, imazapic, imazapyr, imazaquin, imazaquin ammonium, imazethapyr, imazethapyr ammonium, imazosulfuron, indanofan, iodosulfuron-methyl, ioxynil, ioxynil octanoate, ioxynil sodium, isoproturon, isouron, isoxaben, isoxaflutole, pyrasulfotole, lactofen, lenacil, linuron, maleic hydrazide, MCPA and its salts (e.g., MCPA-dimethylammonium, MCPA-potassium and MCPA-sodium, esters (e.g., MCPA-2 ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop P, mefenacet, mefluidide, mesosulfuron-methyl, mesotrione, metam sodium, metamifop, metamitron, metazachlor, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron methyl, molinate, monolinuron, naproanilide, napropamide, naptalam, neburon, nicosulfuron, norflurazon, orbencarb, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxyamid, phenmedipham, picloram, picloram potassium, picolinafen, pinoxaden, piperofos, pretilachlor, primisulfuron methyl, prodiamine, profoxydim, prometon, prometryn, propachlor, propanil, propaquizafop, propazine, propham, propisochlor, propoxycarbazone, propyzamide, prosulfocarb, prosulfuron, pyraclonil, pyraflufen-ethyl, pyrasulfotole, pyrazogyl, pyrazolynate, pyrazoxyfen, pyrazosulfuron ethyl, pyribenzoxim, pyributicarb, pyridate, pyriftalid, pyriminobac methyl, pyrimisulfan, pyrithiobac, pyrithiobac sodium, pyroxsulam, quinclorac, quinmerac, quinoclamine, quizalofop ethyl, quizalofop P ethyl, quizalofop P tefuryl, rimsulfuron, sethoxydim, siduron, simazine, simetryn, sulcotrione, sulfentrazone, sulfometuron methyl, sulfosulfuron, 2,3,6-TBA, TCA, TCA sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron methyl, thiobencarb, tiocarbazil, topramezone, tralkoxydim, tri allate, triasulfuron, triaziflam, tribenuron methyl, triclopyr, triclopyr butotyl, triclopyr triethylammonium, tridiphane, trietazine, trifloxysulfuron, trifluralin, triflusulfuron methyl, tritosulfuron and vernolate.

Additional herbicides include those that are applied over plants having homogentisate solanesyltransferase (HST) polypeptide such as those described in WO2010029311 (A2), herein incorporate by reference it its entirety.

Other herbicides that can be used when an HPPD inhibitor tolerant sequence is present in the plant include, but are not limited to, triketones (such as, mesotrione, sulcotrione, topremezone, and tembotrione) including agriculturally suitable salts (e.g., sodium salts) thereof; isoxazoles (such as, pyrasulfotole and isoxaflutole) including agriculturally suitable salts (e.g., sodium salts) thereof; pyrazoles (such as, benzofenap, pyrazoxyfen, and pyrazolynate) including agriculturally suitable salts (e.g., sodium salts) thereof; and benzobicyclon, including agriculturally suitable salts (e.g., sodium salts) thereof. See, WO2005/053407. In some embodiments, a combination of two or more HPPD inhibitors is applied.

Other suitable herbicides and agricultural chemicals are known in the art, such as, for example, those described in WO 2005/041654. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butyl. and *Puccinia thlaspeos* Schub. Combinations of various herbicides can result in a greater-than-additive (i.e., synergistic) effect on weeds and/or a less-than-additive effect (i.e. safening) on crops or other desirable plants. In certain instances, combinations of one or more ALS inhibitors with other herbicides having a similar spectrum of control but a different mode of action will be particularly advantageous for preventing the development of resistant weeds.

The time at which a herbicide is applied to an area of interest (and any plants therein) may be important in optimizing weed control. The time at which a herbicide is applied may be determined with reference to the size of plants and/or the stage of growth and/or development of plants in the area of interest, e.g., crop plants or weeds growing in the area.

Ranges of the effective amounts of herbicides can be found, for example, in various publications from University Extension services. See, for example, Bernards et al. (2006) Guide for Weed Management in Nebraska (www.ianrpubs.url.edu/sendlt/ec130); Regher et al. (2005) *Chemical Weed Control for Fields Crops, Pastures, Rangeland, and Non-cropland*, Kansas State University Agricultural Extension Station and Corporate Extension Service; Zollinger et al. (2006) *North Dakota Weed Control Guide*, North Dakota Extension Service, and the Iowa State University Extension at www.weeds.iastate.edu, each of which is herein incorporated by reference.

Many plant species can be controlled (i.e., killed or damaged) by the herbicides described herein. Accordingly, the methods of the invention are useful in controlling these plant species where they are undesirable (i.e., where they are weeds). These plant species include crop plants as well as species commonly considered weeds, including but not limited to species such as: blackgrass (*Alopecurus myosuroides*), giant foxtail (*Setaria faberi*), large crabgrass (*Digitaria sanguinalis*), Surinam grass (*Brachiaria decumbens*), wild oat (*Avena fatua*), common cocklebur (*Xanthium pensylvanicum*), common lambsquarters (*Chenopodium album*), morning glory (*Ipomoea coccinea*), pigweed (*Amaranthus* spp.), velvetleaf (*Abutilion theophrasti*), common barnyardgrass (*Echinochloa crus-galli*), bermudagrass (*Cynodon dactylon*), downy brome (*Bromus tectorum*), goosegrass (*Eleusine indica*), green foxtail (*Setaria viridis*), Italian ryegrass (*Lolium multiflorum*), Johnsongrass (*Sorghum halepense*), lesser canarygrass (*Phalaris minor*), windgrass (*Apera spica-venti*), wooly cupgrass (*Erichloa villosa*), yellow nutsedge (*Cyperus esculentus*), common chickweed (*Stellaria media*), common ragweed (*Ambrosia artemisiifolia*), *Kochia scoparia*, horseweed (*Conyza canadensis*), rigid ryegrass (*Lolium rigidum*), goosegrass (*Eleucine indica*), hairy fleabane (*Conyza bonariensis*), buckhorn plantain (*Plantago lanceolata*), tropical spiderwort (*Commelina benghalensis*), field bindweed (*Convolvulus arvensis*), purple nutsedge (*Cyperus rotundus*), redvine (*Brunnichia ovata*), hemp sesbania (*Sesbania exaltata*), sicklepod (*Senna obtusifolia*), Texas blueweed (*Helianthus ciliaris*), and Devil's claws (*Proboscidea louisianica*). In other embodiments, the weed comprises a herbicide-resistant ryegrass.

In some embodiments, a plant having the ALS inhibitor tolerant sequence disclosed herein or active variants and fragments thereof is not significantly damaged by treatment with an ALS inhibitor applied to that plant, whereas an appropriate control plant is significantly damaged by the same treatment.

Generally, the ALS inhibitor is applied to a particular field (and any plants growing in it) no more than 1, 2, 3, 4, 5, 6, 7, or 8 times a year, or no more than 1, 2, 3, 4, or 5 times per growing season.

Thus, methods of the invention encompass applications of herbicide which are "preemergent," "postemergent," "preplant incorporation" and/or which involve seed treatment prior to planting.

In one embodiment, methods are provided for coating seeds. The methods comprise coating a seed with an effective amount of a herbicide or a combination of herbicides (as disclosed elsewhere herein). The seeds can then be planted in an area of cultivation. Further provided are seeds having a coating comprising an effective amount of a herbicide or a combination of herbicides (as disclosed elsewhere herein). In other embodiments, the seeds can be coated with at least one fungicide and/or at least one insecticide and/or at least one herbicide or any combination thereof.

"Preemergent" refers to a herbicide which is applied to an area of interest (e.g., a field or area of cultivation) before a plant emerges visibly from the soil. "Postemergent" refers to a herbicide which is applied to an area after a plant emerges visibly from the soil. In some instances, the terms "preemergent" and "postemergent" are used with reference to a weed in an area of interest, and in some instances these terms are used with reference to a crop plant in an area of interest. When used with reference to a weed, these terms may apply to only a particular type of weed or species of weed that is present or believed to be present in the area of interest. While any herbicide may be applied in a preemergent and/or postemergent treatment, some herbicides are known to be more effective in controlling a weed or weeds when applied either preemergence or postemergence. For example, rimsulfuron has both preemergence and postemergence activity, while other herbicides have predominately preemergence (metolachlor) or postemergence (glyphosate) activity. These properties of particular herbicides are known in the art and are readily determined by one of skill in the art. Further, one of skill in the art would readily be able to select appropriate herbicides and application times for use with the transgenic plants of the invention and/or on areas in which transgenic plants of the invention are to be planted. "Preplant incorporation" involves the incorporation of compounds into the soil prior to planting.

Thus, improved methods of growing a crop and/or controlling weeds such as, for example, "pre-planting burn down," are provided wherein an area is treated with herbicides prior to planting the crop of interest in order to better control weeds. The invention also provides methods of growing a crop and/or controlling weeds which are "no-till" or "low-till" (also referred to as "reduced tillage"). In such methods, the soil is not cultivated or is cultivated less frequently during the growing cycle in comparison to traditional methods; these methods can save costs that would otherwise be incurred due to additional cultivation, including labor and fuel costs.

The term "safener" refers to a substance that when added to a herbicide formulation eliminates or reduces the phytotoxic effects of the herbicide to certain crops. One of ordinary skill in the art would appreciate that the choice of safener depends, in part, on the crop plant of interest and the particular herbicide or combination of herbicides. Exemplary safeners suitable for use with the presently disclosed herbicide compositions include, but are not limited to, those disclosed in U.S. Pat. Nos. 4,808,208; 5,502,025; 6,124,240 and U.S. Patent Application Publication Nos. 2006/0148647; 2006/0030485; 2005/0233904; 2005/0049145; 2004/0224849; 2004/0224848; 2004/0224844; 2004/0157737; 2004/0018940; 2003/0171220; 2003/0130120; 2003/0078167, the disclosures of which are incorporated herein by reference in their entirety. The methods of the invention can involve the use of herbicides in combination with herbicide safeners such as benoxacor, BCS (1-bromo-4-[(chloromethyl)sulfonyl]benzene), cloquintocet-mexyl, cyometrinil, dichlormid, 2-(dichloromethyl)-2-methyl-1,3-dioxolane (MG 191), fenchlorazole-ethyl, fenclorim, flurazole, fluxofenim, furilazole, isoxadifen-ethyl, mefenpyr-diethyl, methoxyphenone ((4-methoxy-3-methylphenyl)(3-methylphenyl)-methanone), naphthalic anhydride (1,8-naphthalic anhydride) and oxabetrinil to increase crop safety. Antidotally effective amounts of the herbicide safeners can be applied at the same time as the compounds of this invention, or applied as seed treatments. Therefore an aspect of the present invention relates to the use of a mixture comprising an ALS inhibitor, at least one other herbicide, and an antidotally effective amount of a herbicide safener.

Seed treatment is useful for selective weed control, because it physically restricts antidoting to the crop plants. Therefore in one embodiment, a method for selectively controlling the growth of weeds in a field comprising treating the seed from which the crop is grown with an antidotally effective amount of safener and treating the field with an effective amount of herbicide to control weeds.

An antidotally effective amount of a safener is present where a desired plant is treated with the safener so that the effect of a herbicide on the plant is decreased in comparison to the effect of the herbicide on a plant that was not treated with the safener; generally, an antidotally effective amount of safener prevents damage or severe damage to the plant treated with the safener. One of skill in the art is capable of determining whether the use of a safener is appropriate and determining the dose at which a safener should be administered to a crop.

As used herein, an "adjuvant" is any material added to a spray solution or formulation to modify the action of an agricultural chemical or the physical properties of the spray solution. See, for example, Green and Foy (2003) "Adjuvants: Tools for Enhancing Herbicide Performance," in *Weed Biology and Management*, ed. Inderjit (Kluwer Academic Publishers, The Netherlands). Adjuvants can be categorized or subclassified as activators, acidifiers, buffers, additives, adherents, antiflocculants, antifoamers, defoamers, antifreezes, attractants, basic blends, chelating agents, cleaners, colorants or dyes, compatibility agents, cosolvents, couplers, crop oil concentrates, deposition agents, detergents, dispersants, drift control agents, emulsifiers, evaporation reducers, extenders, fertilizers, foam markers, formulants, inerts, humectants, methylated seed oils, high load COCs, polymers, modified vegetable oils, penetrators, repellants, petroleum oil concentrates, preservatives, rainfast agents, retention aids, solubilizers, surfactants, spreaders, stickers, spreader stickers, synergists, thickeners, translocation aids, uv protectants, vegetable oils, water conditioners, and wetting agents.

In addition, methods of the invention can comprise the use of a herbicide or a mixture of herbicides, as well as, one or more other insecticides, fungicides, nematocides, bactericides, acaricides, growth regulators, chemosterilants, semiochemicals, repellents, attractants, pheromones, feeding stimulants or other biologically active compounds or entomopathogenic bacteria, virus, or fungi to form a multi-component mixture giving an even broader spectrum of agricultural protection. Examples of such agricultural protectants which can be used in methods of the invention include: insecticides such as abamectin, acephate, acetamiprid, amidoflumet (S 1955), avermectin, azadirachtin, azinphos methyl, bifenthrin, bifenazate, buprofezin, carbofuran, cartap, chlorfenapyr, chlorfluazuron, chlorpyrifos, chlorpyrifos-methyl, chromafenozide, clothianidin, cyflumetofen, cyfluthrin, beta cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion methyl, permethrin, phorate, phosalone, phosmet, phosphamidon, pirimicarb, profenofos, profluthrin, pymetrozine, pyrafluprole, pyrethrin, pyridalyl, pyriprole, pyriproxyfen, rotenone, ryanodine, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyroInitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai*, *Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

The methods of controlling weeds can further include the application of a biologically effective amount of a herbicide of interest or a mixture of herbicides, and an effective amount of at least one additional biologically active compound or agent and can further comprise at least one of a surfactant, a solid diluent or a liquid diluent. Examples of such biologically active compounds or agents are: insecticides such as abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenvalerate, fipronil, flonicamid, flucythrinate, tau fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenyl-amino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), flumorf/flumorlin (SYP-L190), fluoxastrobin (HEC 5725), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), metrafenone (AC375839), myclobutanil, neo-asozin (ferric methane-arsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai*, *Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV. Methods of the invention may also comprise the use of plants genetically transformed to express proteins (such as *Bacillus thuringiensis* delta-endotoxins) toxic to invertebrate pests. In such embodiments, the effect of exogenously applied invertebrate pest control compounds may be synergistic with the expressed toxin proteins. General references for these agricultural protectants include *The Pesticide Manual*, 13th Edition, C. D. S. Tomlin, Ed., British Crop Protection Council, Farnham, Surrey, U.K., 2003 and *The BioPesticide Manual*, 2nd Edition, L. G. Copping, Ed., British Crop Protection Council, Farnham, Surrey, U.K., 2001.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of this invention can also provide a broader spectrum of plant protection and be advantageous for resistance management.

Thus, methods of controlling weeds can employ a herbicide or herbicide combination and may further comprise the use of insecticides and/or fungicides, and/or other agricultural chemicals such as fertilizers. The use of such combined treatments of the invention can broaden the spectrum of activity against additional weed species and suppress the proliferation of any resistant biotypes.

Methods can further comprise the use of plant growth regulators such as aviglycine, N-(phenylmethyl)-1H-purin-6-amine, ethephon, epocholeone, gibberellic acid, gibberellin A4 and A7, harpin protein, mepiquat chloride, prohexadione calcium, prohydrojasmon, sodium nitrophenolate and trinexapac-methyl, and plant growth modifying organisms such as *Bacillus cereus* strain BP01.

C. Methods Using ALS Inhibitor-Tolerant Sequences as Selectable Markers for Transformation In some embodiments, a construct comprising an ALS inhibitor-tolerant polypeptide functions as a selectable marker, e.g., in a plant, bacteria, actinomycete, yeast, algae or other fungi. For example, an organism that has been transformed with a vector comprising an ALS inhibitor tolerant polynucleotide can be selected based on its ability to grow in the presence of an ALS inhibitor as demonstrated in Example 6.

Other embodiments include methods comprising selecting a plant cell which is resistant or tolerant to at least one ALS inhibitor by growing plant cells in a sufficient concentration of the at least one ALS inhibitor, such that the herbicide kills the plant cells which do not comprise the ALS inhibitor-tolerant polypeptide of interest. The plant cell can be from any of the plants described previously.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Example 1

ALS Mutagenesis and *E. coli* Expression Vector Cloning

A survey of known ALS (AcetoLactate Synthase) gene variants (Table 2) was performed, and a number of ALS variants were selected for kinetic evaluation based on breadth and strength of insensitivity to ALS-inhibitor herbicides as well as kinetic activity parameters including the ratio of substrate preferences. The selected ALS gene variants (Table 3) were generated by PCR mediated site-directed mutagenesis. Finnzymes PHUSION® DNA polymerase (Cat. No. F-530S) was used for the PCR reactions, following the instructions for recommended temperatures and cycles in the PHUSION® protocol. Some mutagenesis reactions were assisted by the use of IN-FUSION® enzyme (Clontech Cat. No. 639620) to circularize a linear plasmid with the mutation located within the 15 nucleotide overlapping ends, via recombination following the manufacturer's protocol for primer design and reaction conditions. The ALS genes, beginning with encoded amino acids SISK, (S48 to K51 in the *G. max* ALS1 protein (SEQ ID NO:1) corresponding to the mature protein N-terminus of the chloroplast localized enzyme), were cloned into the PMAL® *E. coli* expression vector (New England Biolabs) to express ALS as a fusion protein with a Maltose-Binding Protein (MBP) at the N-terminus with a thrombin site for cleavage and a His-6 tag for affinity purification. All in vitro protein characterization described in the examples was carried out with the isolated proteins after cleavage from the His-MBP fusion partner.

TABLE 2

Survey of ALS substitutions known to confer herbicide resistance in plants or to desensitize the enzyme to inhibition.

| Position: *A. thal.*; *G. max* | Substitution | Source of desensitized ALS | Resistance pattern, I50 fold increase | Kinetic parameters, % wt | References |
|---|---|---|---|---|---|
| G121; 102 | G116S | Site-directed mutation in *Saccharomyces cerevisiae* ALS | SUs, 1000-10000<br>IMs 15-300 | kcat, 75<br>Km, 20 | Duggleby RG et al., Eur J Biochem 270, 2895-2904 (2003) |
| A122, 103 | A121T | Site-directed mutation in *Nicotiana tobacum* ALS | SU, >200<br>IM, >200 | kcat, 20<br>Km, 90<br>Kc FAD and TPP, 300 | Chong C-K and Choi, J-D, Biochem Biophys Res Comm 279, 462-467 (2000) |
| | A122T | Resistant isolate of *Amaranthus hybridus* | SU, TP, Pyrithiobac, 1<br>IM, 1000 | | Trucco F et al., J Plant Phys 163, 475-479 (2006) |
| | A122V | Site-directed mutation in *A. thaliana* ALS | SUs, 4<br>IMs, 1000-2000 | kcat, 25<br>Km, 160<br>Kc for TPP, 2000<br>Kc for FAD, 400 | Chang AK and Duggleby RG, Biochem J 333, 765-777 (1998) |
| V196, 177 | V99M | Chemical mutagenesis of *Escherichia coli* ALS II gene | SUs, 100-250<br>IM, 3-5 | kcat, 66<br>Km, 51<br>Kc for FAD, 400<br>Kc for TPP, 2800 | Hill CM and Duggleby RG, Biochem J 335, 653-661 (1998) |
| P197, 178 | P197S | Chemical mutagenesis of *A. thaliana* plants | CS, 1000<br>IP, 2 | | Haugh GW and Somerville C, Mol Gen Genet 204, 430-434 (1986) |
| | P192S | Site-directed mutations in *S. cerevisiae* ALS | SUs, 400-2000<br>IEt, 10 | kcat, 25<br>Km, 75 | Duggleby RG et al., Eur J Biochem 270, 2895-2904 (2003) |
| | P197L | Resistant isolate of *Amaranthus retroflexus* | 10 to 100 on a broad spectrum of active ingredients | kcat, 70 | Sibony M et al., Weed Res 41, 509-522 (2001) |
| R199, 180 | R199E | Site-directed mutation in *A. thalianan* ALS | SM, 2<br>IEt, 50 | | Ott K-H et al., J Mol Biol 263, 359-368 (1996) |
| A205, 186 | A200V | Site-directed mutations in *S. cerevisiae* ALS | SUs, 300-700<br>IMs, 10-100 | kcat, 20; Km, 100 | Duggleby RG et al., Eur J Biochem 270, 2895-2904 (2003) |
| | A108V | Chemical mutagenesis of *E. coli* ALS II gene | SUs, 100-400<br>IMs, 3-4 | kcat, 87<br>Km, 67<br>Kc for TPP, 350 | Hill CM and Duggleby RG, Biochem J 335, 653-661 (1998) |
| | A205V | Resistant isolate of *Helianthus annuus* | IM resistant plants | No enzyme data | Kolkman JM et al., Theor Appl Genet 109, 1147-1159 (2004) |
| K256, 237 | K251T | Site-directed mutations in *S. cerevisiae* ALS | SU, 10-100<br>IMs, 10-150 | kcat, 1; Km, 65 | Duggleby RG et al., Eur J Biochem 270, 2895-2904 (2003) |
| | K255F, Q | Site-directed mutation in *N. tobacum* ALS | SU, >240<br>IM, >820<br>TP, >10000 | kcat, 54-116<br>Km, 640-670<br>Normal co-factor binding | Yoon T-Y et al., Biochem Biophys Res Comm 293, 433-439 (2002) |
| M351, 332 | M350C | Site-directed mutation in *N. tobacum* ALS | SU, 34 | kcat, 7<br>Km, 1700<br>Kc for FAD, 5000 | Le DT et al., Biochem Biophys Res Comm 306, 1075-1082 (2003) |
| | M354V | Site-directed mutations in *S. cerevisiae* ALS | SUs, 5-85<br>IP, 10; IEt, 90 | kcat, 50<br>Km, 60 | Duggleby RG et al., Eur J Biochem 270, 2895-2904 (2003) |

TABLE 2-continued Survey of ALS substitutions known to confer herbicide resistance in plants or to desensitize the enzyme to inhibition.

| Position: A. thal.; G. max | Substitution | Source of desensitized ALS | Resistance pattern, I50 fold increase | Kinetic parameters, % wt | References |
|---|---|---|---|---|---|
| D375, 356 | D374A | Site-directed mutation in N. tobacum ALS | SU, 60<br>IM, 44 | kcat, 58<br>Km, 49<br>Kc FAD, normal<br>Kc TPP, 10x reduced | Le DT et al., Biochim Biophys Acta 1749, 103-112 (2005) |
| D376, 357 | D375A | Site-directed mutation in N. tobacum ALS | SU, >77<br>IM, 0.2 | kcat, 42<br>Km, 931<br>Kc TPP, 500 | Le DT et al., Biochim Biophys Acta 1749, 103-112 (2005) |
| | D375E | Site-directed mutation in N. tobacum ALS | BenSU, >77<br>IPic, 9.5<br>TP, 34 | kcat, 100<br>Km, 31<br>Kc FAD, reduced<br>Kc TPP, normal | Le DT et al., Biochim Biophys Acta 1749, 103-112 (2005) |
| | D379N | Site-directed mutations in S. cerevisiae ALS | SUs, 200-900<br>IMs, hypersensitivity | kcat, 140<br>Km, 133 | Duggleby RG et al., Eur J Biochem 270, 2895-2904 (2003) |
| | D375E | Resistant isolate of A. hybridus | In plants: SUs, high<br>IM, TP moderate | None | Whaley CM et al., Weed Sci 55, 83-90 (2007) |
| M570, 551 | M460N | Site-directed mutatiion in E. coli ALS | SM, >20 | kcat, no data<br>Km, 120<br>Kc for TPP, FAD, 5000 | Ibdah M et al., Biochem 35, 16282-16291 (1996) |
| | M569C | Site-directed mutation in N. tobacum ALS | SU, TP, high<br>IM, 50 | kcat, 4<br>Km, 100<br>Kc FAD, 2000 | Le DT et al., Biochem Biophys Res Comm 306, 1075-1082 (2003) |
| V571, 552 | V570Q | Site-directed mutation in N. tobacum ALS | SU, high resistance<br>IM, moderate | kcat, 24<br>Km, 1800<br>Kc for FAD, 600<br>Kc for TPP, 1300 | Jung S-M et al., Biochem J 383, 53-61 (2004) |
| W574, 555 | W586L | Site-directed mutations in S. cerevisiae ALS | SUs, 1000-10000<br>IMs, 8-70 | kcat, 450<br>Km, 80 | Duggleby RG et al., Eur J Biochem 270, 2895-2904 (2003) |
| | W552L | Resistant isolate of Xanthium strumarium | SU, TP, >6000<br>IMt, >7.2<br>POB, 2200 | | Bernasconi P et al., J Biol Chem 270, 17381-17385 (1995) |
| | W542L | Pioneer3180IR, XA17 gene | SU, TP, 2000<br>IM, 1000<br>POB, 1100 | | Bernasconi P et al., J Biol Chem 270, 17381-17385 (1995) |
| | W574S, L | Site-directed mutation in A. thalianan ALS | SU, IM; high | kcat, 40-170<br>Km, 185-533 | Chang AK and Duggleby RG, Biochem J 333, 765-777 (1998) |
| F578, 559 | F590L | Site-directed mutations in S. cerevisiae ALS | SUs, 30-300<br>IM, 60 | kcat, 200<br>Km, 30 | Duggleby RG et al., Eur J Biochem 270, 2895-2904 (2003) |
| | F577D, E | Site-directed mutation in N. tobacum ALS | SU, >4000<br>IM, >64 | kcat, 51-73<br>Km, 280-342<br>Kc for TPP, 300-600 | Jung S-M et al., Biochem J 383, 53-61 (2004) |
| S653, 634 | S653N, T | Plant mutagenesis, Site-directed mutation in A. thaliana ALS | SUs, 0.5-3<br>IP, 400-1000 | kcat, 80-170<br>Km, 50-80<br>Normal cofactor binding | Haughn GW and Somerville C, Plant Physiol 92, 1081-1085 (1990)<br>Chang AK and Duggleby RG, Biochem J 333, 765-777 (1998) |
| | S621N | Zea mays | IM tolerant maize | | EP 0 525384 A3 |

All kcat and Km values are for pyruvate reactions.
Abbreviations:
IM, imadazolinone;
IZ, imazapyr;
IEt, imazethapyr;
IPic, imazapic;
SU, sulfonylurea, BenSU, bensulfuron;
SM, sulfometuron methyl;
CS, chlorsulfuron;
POB, pyrimidyloxybenzoate;
TP, triazolopyrimidine;
Kc, cofactor activation constant;
FAD, flavin adeninie dinucleotide;
TPP, thiamin pyrophosphate;
*A. thal*, Arabidopsis thaliana;
*G. max*, Glycine max

TABLE 3

Substitutions constructed in the *G. max* ALS1 protein.

| SEQ ID NO | Description |
|---|---|
| 1 | GM-ALS1 (WILD-TYPE) |
| 2 | GM-ALS_G102S |
| 3 | GM-ALS_G102S_P178S |
| 4 | GM-ALS_G102S_D357E |
| 5 | GM-ALS_G102S_D357N |
| 6 | GM-ALS_A103T |
| 7 | GM-ALS_A103T_P178S |
| 8 | GM-ALS_A103T_P178S_D357E |
| 9 | GM-ALS_P178A |
| 10 | GM-ALS_P178A_W555L |
| 11 | GM-ALS_P178A_F559D |
| 12 | GM-ALS_P178L |
| 13 | GM-ALS_P178L_W555L |
| 14 | GM-ALS_P178Q |
| 15 | GM-ALS_P178S |
| 16 | GM-ALS_P178S_A186V |
| 17 | GM-ALS_P178S_D357E |
| 18 | GM-ALS_P178S_D357N |
| 19 | GM-ALS_P178S_F559D |
| 20 | GM-ALS_A186D |
| 21 | GM-ALS_A186V |
| 22 | GM-ALS_K237F |
| 23 | GM-ALS_K237Q |
| 24 | GM-ALS_D357E |
| 25 | GM-ALS_D357N |
| 26 | GM-ALS_W555L |
| 27 | GM-ALS_F559D |
| 28 | GM-ALS_F559L |

Example 2

Recombinant ALS Expression and Purification

ONE SHOT® BL21 (DE3) cells transformed with a plasmid encoding ALS with an N-terminal His-MBP fused tag as described in Example 1 were grown in LB broth at 37° C. When the culture reached an O.D. of 0.7, expression was induced with 0.25 mM IPTG and cultures were incubated at 16° C. for approximately 16 hours. Cells were collected by centrifugation and resuspended in 50 ml of Buffer A (25 mM HEPES (pH 7.5), 300 mM NaCl and 10% glycerol) plus 5 mM mercaptoethanol and complete, EDTA free, protease inhibitors (Roche) (Buffer B). Cells were disrupted by sonication and the final solution was made 1% in TritonX-100. Cell debris was removed by centrifugation at 30,000×g for 15 minutes. Concentrated imidazole was added to the 30,000×g supernatant to a concentration of 10 mM and then incubated with Ni-NTA resin, equilibrated in Buffer C (Buffer A+1% TritonX-100 and 5 mM b-mercaptoethanol), at 4° C. for 1 hour. The resin was collected by centrifugation, washed twice in Buffer D (Buffer A+0.5 mM thiamine pyrophosphate, 2 uM FAD, 1 mM pyruvate and 0.5 mM MgCl$_2$) containing 10 mM imidazole and his-tagged protein was eluted with buffer D containing 250 mM imidazole.

Amylose resin was used to further purify the fusion protein and remove imidazole from the Ni-NTA step. Amylose resin was equilibrated in Buffer E (25 mM HEPES (pH 7.5), 5 mM mercaptoethanol, 200 mM NaCl, 2 uM FAD, 1 mM pyruvate, 0.5 mM TPP, 5% glycerol, and 0.1% BRIJ-35 (EMD Chemicals). Ni-NTA eluted protein was passed through the column under gravity flow. The column was then washed with several volumes of Buffer E and fusion protein was then eluted with Buffer F (Buffer E+10 mM maltose). The His-MBP tag was removed by incubation with 2 units of thrombin per mg of ALS fusion protein at 25° C. for two hours. A Ni-agarose column was used to separate the His-MBP tag from ALS.

Example 3

Kinetic and Inhibition Assays

Km and Kcat determinations for recombinant ALS variants (with respect to pyruvate as the substrate) were performed using a colorimetric assay. ALS assays were carried out in 96-well microplates with 150 ul reaction containing 25 mM potassium phosphate, 0.2 mg/ml BSA, 15 mM MgCl$_2$, 0.7 mM TPP, 28 uM FAD and 0-100 mM sodium pyruvate. Reactions were initiated by the addition of ALS enzyme to a final amount of 0.8 ug/well. Parameters for Km and Vmax were determined by fitting the velocity versus substrate concentration data to a rectangular hyperbola using GraphPad Prism software. Kcat values were determined from Vmax based on protein concentration in the reactions. The kinetic parameters for each of the variants are shown in Table 4.

TABLE 4

Kinetic values of ALS variants for pyruvate substrate.

| | | Pyruvate | | |
|---|---|---|---|---|
| SEQ ID NO | ALS Variant | kcat (min$^{-1}$) | Km (mM) | kcat/Km (min$^{-1}$ mM$^{-1}$) |
| 1 | GM-ALS1 | 56 | 3 | 18.5 |
| 2 | GM-ALS_G102S | 80 | 3.5 | 22.7 |
| 3 | GM-ALS_G102S_P178S | 88 | 5 | 17.6 |
| 4 | GM-ALS_G102S_D357E | 105 | 8 | 13.1 |
| 5 | GM-ALS_G102S_D357N | 68 | 11 | 6.1 |
| 6 | GM-ALS_A103T | 109 | 3 | 36.3 |
| 7 | GM-ALS_A103T_P178S | 125 | 10 | 12.5 |
| 8 | GM-ALS_A103T_P178S_D357E | 63 | 21 | 3.0 |
| 9 | GM-ALS_P178A | 65 | 5 | 13.1 |
| 10 | GM-ALS_P178A_W555L | 90 | 15 | 6.0 |
| 11 | GM-ALS_P178A_F559D | 36 | 40 | 0.9 |
| 12 | GM-ALS_P178L | 251 | 14.8 | 17.0 |
| 13 | GM-ALS_P178L_W555L | 21 | 36 | 0.6 |
| 14 | GM-ALS_P178Q | 163 | 3 | 54.5 |
| 15 | GM-ALS_P178S | 69 | 1.6 | 42.9 |
| 16 | GM-ALS_P178S_A186V | 27 | 21 | 1.3 |
| 17 | GM-ALS_P178S_D357E | 190 | 6 | 31.6 |
| 18 | GM-ALS_P178S_D357N | 109 | 4 | 27.2 |
| 19 | GM-ALS_P178S_F559D | 50 | 40 | 1.3 |
| 20 | GM-ALS_A186D | 9 | 35 | 0.2 |
| 21 | GM-ALS_A186V | 28 | 14 | 2.0 |
| 22 | GM-ALS_K237F | 130 | 27 | 4.8 |
| 23 | GM-ALS_K237Q | 81 | 20 | 4.0 |
| 24 | GM-ALS_D357E | 168 | 3 | 55.9 |
| 25 | GM-ALS_D357N | 150 | 6 | 25.1 |
| 26 | GM-ALS_W555L | 65 | 1.8 | 36.3 |
| 27 | GM-ALS_F559D | 25 | 20 | 1.3 |
| 28 | GM-ALS_F559L | 107 | 6 | 17.8 |

For sulfonylurea (SU) and imidazolinone (IMI) IC50 determinations, stock inhibitor concentrations were made 15 mM in DMSO. Various concentrations of inhibitor were pre-incubated with enzyme in reaction buffer (without sodium pyruvate) at room temperature for 15 minutes and sodium pyruvate was then added to each well to start the reaction. The microplates were incubated at 37° C. for 1 hour and then 100 ul of each reaction was transferred to a 96 well fiber-glass B filter plate. To each well was then added 10 ul of 6N H$_2$SO$_4$ and plates were incubated at 60° C. for 15 minutes. 100 ul of 0.5% creatine and 50 ul of α-naphthol were then added to each well and plates were incubated at 60° C. for an additional 15 minutes. The solutions in each well were filtered on a vacuum manifold into a collection plate and the amount of acetolactate formed in the reaction was determined by UV detection at 530 nm. IC50 values for inhibition are shown in Table 5 and were determined by fitting percent inhibition versus the Log (inhibitor concentration) to a sigmoidal dose-response curve in GraphPad prism software. Values greater than wild type GM-ALS1 (SEQ ID NO:1) indicate tolerance to ALS inhibitor herbicides.

of the reduced products was then plotted versus the concentration of 2-ketobutyrate. As the 2-ketobutyrate amount increased there was a consequent increase in reduced acetohydroxybutyrate (AHB) and decrease in reduced acetolactate (AL). The point of intersection of the two products was used to determine the substrate specificity ratio, Rf, which is the ratio of [pyruvate] to [2-ketobutyrate] that resulted in equal rates of formation of acetolactate and acetohydroxybutyrate. The substrate specificity ratio was ~114 for the wild type enzyme compared to 3 for the highly resistant allele (HRA) double mutant ALS variant (SEQ ID NO: 10).

TABLE 5

Herbicide inhibition IC50 values for ALS variants.

| SEQ ID NO | ALS Variant | SU IC50 (nM) | | | | | | IMI IC50 (nM) | |
|---|---|---|---|---|---|---|---|---|---|
| | | Rim | Thifen-me | Triben-me | CS | Chlor-et | Met-me | IM-quin | IM-pyr |
| 1 | GM-ALS1 | 11 | 90 | 270 | 24 | 9.7 | 20 | 6000 | 9800 |
| 2 | GM-ALS_G102S | 328 | 434 | 25000 | 280 | 2800 | | >100000 | >100000 |
| 3 | GM-ALS_G102S_P178S | >100000 | >100000 | >100000 | >100000 | >100000 | | >100000 | >100000 |
| 4 | GM-ALS_G102S_D357E | >100000 | >100000 | >100000 | 23000 | >100000 | | >100000 | >100000 |
| 5 | GM-ALS_G102S_D357N | ~100000 | 19000 | 44000 | 4000 | 15000 | | ~100000 | >100000 |
| 6 | GM-ALS_A103T | 7800 | 490 | 2200 | 575 | 228 | 85 | >100000 | >100000 |
| 7 | GM-ALS_A103T_P178S | >100000 | ~100000 | >100000 | >100000 | 43000 | 42000 | >100000 | >100000 |
| 8 | GM-ALS_A103T_P178S_D357E | >100000 | >100000 | >100000 | >100000 | >100000 | | >100000 | >100000 |
| 9 | GM-ALS_P178A | 2100 | 23000 | >100000 | 40000 | 4400 | 2850 | 25000 | 76000 |
| 10 | GM-ALS_P178A_W555L | >100000 | >100000 | >100000 | >100000 | >100000 | >100000 | >100000 | >100000 |
| 11 | GM-ALS_P178A_F559D | ~100000 | >100000 | >100000 | >100000 | 27000 | | >100000 | >100000 |
| 12 | GM-ALS_P178L | 500 | 27000 | >100000 | 2260 | 2670 | 1300 | 40000 | >100000 |
| 13 | GM-ALS_P178L_W555L | >100000 | >100000 | >100000 | >100000 | >100000 | | >100000 | >100000 |
| 14 | GM-ALS_P178Q | 5000 | 63000 | >100000 | 75000 | 5800 | 6300 | 86000 | >100000 |
| 15 | GM-ALS_P178S | 13000 | >100000 | >100000 | >100000 | >100000 | 6750 | 80000 | >100000 |
| 16 | GM-ALS_P178S_A186V | 52000 | >100000 | >100000 | >100000 | >100000 | | >100000 | >100000 |
| 17 | GM-ALS_P178S_D357E | >100000 | >100000 | >100000 | >100000 | >100000 | >100000 | >100000 | >100000 |
| 18 | GM-ALS_P178S_D357N | >100000 | >100000 | >100000 | >100000 | >100000 | | 6700 | 25000 |
| 19 | GM-ALS_P178S_F559D | >100000 | >100000 | >100000 | >100000 | >100000 | >100000 | >100000 | >100000 |
| 20 | GM-ALS_A186D | 5152 | >100000 | >100000 | ~100000 | >100000 | | >100000 | >100000 |
| 21 | GM-ALS_A186V | 182 | 2900 | 68000 | 2200 | 1700 | | >100000 | >100000 |
| 22 | GM-ALS_K237F | 3588 | 7200 | 16000 | 338 | 1367 | | >100000 | >100000 |
| 23 | GM-ALS_K237Q | 270 | 609 | 4700 | 1000 | 396 | | >100000 | >100000 |
| 24 | GM-ALS_D357E | 3738 | 93310 | >100000 | 32000 | 79000 | | 60000 | 66000 |
| 25 | GM-ALS_D357N | 123 | 1580 | 7300 | 487 | 478 | | 975 | 1100 |
| 26 | GM-ALS_W555L | >100000 | >100000 | >100000 | >100000 | >100000 | >100000 | >100000 | >100000 |
| 27 | GM-ALS_F559D | 100 | 1915 | 11000 | 440 | 488 | | 74000 | >100000 |
| 28 | GM-ALS_F559L | 65 | 994 | 4400 | 411 | 180 | 6100 | ~100000 | ~100000 |

Abbreviations: Rim, rimsulfuron; Thifen-me, thifensulfuron-methyl; Triben-me, tribenuron-methyl; CS, chlorsulfuron; Chlor-et, chlorimuron-ethyl; Met-me, metsulfuron-methyl; IM-quin, imazaquin; IM-pyr, imazapyr.

Example 4

Determination of Substrate Specificity

Substrate preference was determined using the assay described in Example 3; however, the assay was conducted using a constant concentration of pyruvate (25 mM) and varying concentrations of the second substrate, 2-ketobutyrate. Each reaction involving a specific ratio of pyruvate to 2-ketobutyrate, after a set period of time, was quenched by addition of sodium borohydride (7-fold excess) to form the reduced adducts of the products of the two substrates namely; reduced acetolactate for the reaction with pyruvate and reduced aceto hydroxybutyrate for the 2-ketobutyrate reaction. The relative amounts of the two reduced products was determined by first, chromatographic separation using a 4.6×250 mm dC18 column (Atlantis) equilibrated with a 0.1% formic acid solution and subsequent elution using a methanol gradient at 0.7 ml/min, followed by detection using a Thermo FINNIGAN® LTQ® Mass Spectrometer (MS). The products of the two reactions were quantified by integration of the MS signals. The % of the amount of each Table 6 shows the specificity ratios for all of the ALS variants studied.

TABLE 6

Substrate specificity ratios (Rf) of ALS variants

| SEQ ID NO | ALS Variant | Substrate specificity ratio |
|---|---|---|
| 1 | GM-ALS1 | 114.0 |
| 2 | GM-ALS_G102S | 10.2 |
| 3 | GM-ALS_G102S_P178S | 12.0 |
| 4 | GM-ALS_G102S_D357E | 16.9 |
| 5 | GM-ALS_G102S_D357N | 10.7 |
| 6 | GM-ALS_A103T | 83.3 |
| 7 | GM-ALS_A103T_P178S | 75.0 |
| 8 | GM-ALS_A103T_P178S_D357E | 114.0 |
| 9 | GM-ALS_P178A | 119.0 |
| 10 | GM-ALS_P178A_W555L | 2.9 |
| 11 | GM-ALS_P178A_F559D | 100.0 |
| 12 | GM-ALS_P178L | 119.0 |
| 13 | GM-ALS_P178L_W555L | 2.7 |

TABLE 6-continued

Substrate specificity ratios (Rf) of ALS variants

| SEQ ID NO | ALS Variant | Substrate specificity ratio |
|---|---|---|
| 14 | GM-ALS_P178Q | 86.0 |
| 15 | GM-ALS_P178S | 104.0 |
| 16 | GM-ALS_P178S_A186V | 29.0 |
| 17 | GM-ALS_P178S_D357E | 100.0 |
| 18 | GM-ALS_P178S_D357N | 49.0 |
| 19 | GM-ALS_P178S_F559D | 89.0 |
| 20 | GM-ALS_A186D | 21.7 |
| 21 | GM-ALS_A186V | 40.3 |
| 22 | GM-ALS_K237F | 100.0 |
| 23 | GM-ALS_K237Q | 100.0 |
| 24 | GM-ALS_D357E | 67.6 |
| 25 | GM-ALS_D357N | 72.0 |
| 26 | GM-ALS_W555L | 2.6 |
| 27 | GM-ALS_F559D | 96.0 |
| 28 | GM-ALS_F559L | 62.5 |

Example 5

Construction of Plant Transformation Vectors

For plant transformation of the ALS variants, GATEWAY® (Invitrogen) entry vectors were built with different promoters to drive expression of the full-length ALS gene at different levels: the polyubiquitin 10 (AT-UBQ10) promoter (DuPont) from *Arabidopsis* for higher expression and the S-adenosylmethionine synthase (SAMS) promoter (U.S. Pat. No. 7,741,537) from soybean for lower expression. Each vector had the native soybean ALS terminator downstream of the ALS gene. To move the selected ALS variants from the *E. coli* vectors into soybean transformation vectors, the *E. coli* vectors were used as PCR templates to subclone the different variants with ends designed for In-Fusion (Clontech) recombination. Restriction enzymes BamHI and NarI were used to cut out the ALS gene from the AT-UBQ10 entry vector and In-Fusion enzyme was used to join the different variant PCR products into the BamHI/NarI AT-UBQ10 entry vector fragment. After the AT-UBQ10 entry vectors were complete, restriction enzymes SpeI and one of either NarI or BamHI were used to cut out the AT-UBQ10 promoter. In-Fusion enzyme was used to join the SAMS promoter, which was cloned by PCR from a different vector, into the NarI/SpeI (or BamHI/SpeI) ALS variant entry vector fragment. The entry vector was used in conjunction with two entry vectors that did not contain genes and a destination vector with hygromycin selection in a GATEWAY® reaction with LR CLONASE® II (Invitrogen). The final vector had two AscI sites that were used to remove the hygromycin selectable marker and make the soybean bombardment fragment.

Example 6

Transformation of Soybean with Modified ALS Genes as Selectable Markers

Soybean plants expressing ALS variant transgenes were produced using the method of particle gun bombardment (Klein et al. (1987) *Nature* 327:70-73, U.S. Pat. No. 4,945,050) using a DuPont BIOLISTIC® PDS1000/He instrument. The vectors used to test modified ALS genes as selectable markers in soybean transformation were composed of the S-adenosylmethionine synthase (SAMS) promoter (U.S. Pat. No. 7,741,537) from soybean, or the polyubiquitin 10 (AT-UBQ10) promoter (DuPont) from *Arabidopsis*, driving the modified ALS coding sequence followed by the native soybean ALS terminator region. The selection agent used during the transformation process was chlorsulfuron. Bombardments were carried out with linear DNA fragments purified away from any bacterial vector DNA. Bombarded soybean embryogenic suspension tissue was cultured for one week in the absence of chlorsulfuron, and then placed in liquid selection medium for 6 weeks. Selection in liquid cultures was at 50 parts per billion (ppb) chlorsulfuron for three weeks, then elevated to 100 ppb. Putative transgenic suspension tissue was sampled for PCR analysis to confirm the presence of the modified ALS gene. Putative transgenic suspension culture tissue was maintained in selection medium for 3 weeks to obtain enough tissue for plant regeneration. Suspension tissue was matured for 4 weeks using standard procedures; matured somatic embryos were desiccated for 4-7 days and then placed on germination induction medium for 2-4 weeks. Germinated plantlets were transferred to soil in cell pack trays for 3 weeks for acclimatization. Plantlets were potted to 10-inch pots in the greenhouse for evaluation and seed production. Wild type ALS is not able to act as a selection marker in soybean with chlorsulfuron selection. Each of the ALS variants shown in Table 7, with the exception of GM_ALS_F559D, showed good selectable marker activity in the transformation protocol.

TABLE 7

Activity as a chlorsulfuron selectable marker in soy transformation using low and high expression promoters

| SEQ ID NO | ALS Variant | Selectable Marker Activity |
|---|---|---|
| 1 | SAMS: GM-ALS1 | – |
| 1 | UBQ10: GM-ALS1 | – |
| 7 | SAMS: GM-ALS_A103T_P178S | +/– |
| 7 | UBQ10: GM-ALS_A103T_P178S | + |
| 8 | SAMS: GM-ALS_A103T_P178S_D357E | + |
| 8 | UBQ10: GM-ALS_A103T_P178S_D357E | + |
| 9 | SAMS: GM-ALS_P178A | + |
| 9 | UBQ10: GM-ALS_P178A | + |
| 10 | SAMS: GM-ALS_P178A_W555L | + |
| 10 | UBQ10: GM-ALS_P178A_W555L | + |
| 15 | SAMS: GM-ALS_P178S | + |
| 15 | UBQ10: GM-ALS_P178S | + |
| 17 | SAMS: GM-ALS_P178S_D357E | + |
| 17 | UBQ10: GM-ALS_P178S_D357E | + |
| 27 | SAMS: GM-ALS_F559D | – |

Example 7

Accumulation of C17 Fatty Acids in Seeds of Transgenic Soybean

Loss of substrate preference for 2-ketobutyrate in ALS variant enzymes (e.g. GM-ALS_W555L) may lead to an increase in the pool size for this metabolite. This in turn may result in increased biosynthesis of C17 fatty acids (FAs). To look for downstream effects of over-expression of ALS variants, the total C17 fatty acids in homozygous T1 transgenic seeds was measured.

Segregating T1 seeds from transgenic soybean events expressing variant ALS enzymes were analyzed by removing small seed chips (approximately 2 mg) with a razor blade. Fatty acid methyl esters (FAMES) were prepared from single seed chips by transesterification using trimethylsulfonium hydroxide (Butte, *J. Chromat.* 261, 142-145 (1983)). Seed chips were placed in a vial containing 50 µl of trimethylsulfonium hydroxide (TMSH) and 0.5 ml of hexane and were incubated for 30 minutes at room temperature with shaking. Fatty acid methyl esters (5 µl injected from hexane layer) were separated and quantified using a Hewlett-Packard 6890 Gas Chromatograph fitted with an OMEGAWAX® 320 fused silica capillary column (Supelco Inc., Bellfonte, Pa.). The oven temperature was programmed to hold at 170° C. for 1 minute, increase to 240° C. at 10° C./minute and then hold for an additional 0.5 minute. Carrier gas was supplied by a Whatman hydrogen generator. Retention times were compared to those for methyl esters of standards commercially available (Nu-Chek Prep, Inc., Elysian, Minn.).

The remaining seed portion was planted and seedlings were tested for transgene zygosity. Positive transgene expressing seed were compared for total C17 fatty acid content. An event with a strong promoter (e.g. SCP1; WO1999043838 SEQ ID NO 12) driving the GM-ALS_P178A_W555L gene accumulated C17 FAs (see FIG. 1) at more than 10× the level in wild type plants (*G. max* elite or Jack germplasm). With a weaker promoter like SAMS (U.S. Pat. No. 7,741,537), most GM-ALS_P178A_W555L events showed only slightly elevated levels of C17 fatty acids, but at least one event (GM-ALS_P178A_W555L-1) specifically selected for high expression showed approximately 3× the level of fatty acids seen in *G. max* untransformed seeds. The variants chosen for minimal alteration of the native enzyme substrate preference showed little to no increases in C17 fatty acid accumulation, even when driven by the strong *Arabidopsis* polyubiquitin 10 promoter. Expression of the native GM-ALS gene with the strong UBQ10 promoter resulted in very little change in C17 FA levels relative to *G. max* untransformed germplasm.

Example 8

Herbicide Spray Tests of Transgenic T1 ALS Soybean Plants Using Chlorsulfuron

T1 plants, each having an ALS variant transgene, were grown to the V1 to V2 growth stage and then sprayed with commercial chlorsulfuron formulation at a rate of 3 g ai/ha. All chlorsulfuron treatments were applied foliarly with 0.25% nonionic surfactant in a spray volume of 374 L/ha. Individual plants were compared to untreated plants of similar genetic background, evaluated for herbicide response at eight days after treatment and assigned a visual response score from 0 to 100% injury (0=no effect to 100=dead plant at day 8).

Null plants that did not contain the ALS variant transgene and plants with wild type ALS transgene were severely injured by chlorsulfuron (>90% injury). Homozygous T1 plants positive for the transgene showed tolerance (0-40% injury) to the chlorsulfuron herbicide due to expression of the ALS variant gene. Results in Table 8 list the lowest injury among plants of a single event for constructs containing the listed expression cassette. The amino acid substituted ALS variants provided more protection than the overexpression of the native ALS gene. Seed was produced from a number of T1 plants and advanced to more extensive herbicide testing in the T2 generation.

TABLE 8

Chlorosulfuron tolerance shown by homozygous T1 soybean transgenic plants overexpressing ALS variant genes

| SEQ ID NO | ALS Variant | Lowest % injury |
|---|---|---|
|  | No transgene | 85% |
| 1 | UBQ10: GM-ALS1 | 90% |
| 10 | SAMS: GM-ALS_P178A_W555L | 10% |
| 9 | UBQ10: GM-ALS_P178A | 10% |
| 15 | UBQ10: GM-ALS_P178S | 5% |
| 17 | UBQ10: GM-ALS_P178S_D357E | 5% |
| 7 | UBQ10: GM-ALS_A103T_P178S | 40% |
| 8 | UBQ10: GM-ALS_A103T_P178S_D357E | 75% |
| 26 | UBQ10: GM-ALS_W555L | 75% |
| 9 | SAMS: GM-ALS_P178A | 0% |
| 15 | SAMS: GM-ALS_P178S | 25% |
| 17 | SAMS: GM-ALS_P178S_D357E | 45% |
| 7 | SAMS: GM-ALS_A103T_P178S | 80% |
| 8 | SAMS: GM-ALS_A103T_P178S_D357E | 80% |
| 26 | SAMS: GM-ALS W555L | 80% |

Example 9

Herbicide Spray Tests of Homozygous Transgenic ALS Soybean Plants with Five Different ALS-Inhibitor Herbicides T1 or T2 soybean plants were evaluated with qPCR to confirm they were homozygous for the transgene. Plants were sprayed at the V1 to V2 growth stage with the commercial formulations of chlorimuron (32 g ai/ha), tribenuron-methyl (16 g ai/ha), thifensulfuron-methyl (16 g ai/ha), rimsulfuron (8 g ai/ha), and imazapyr (4 g ai/ha). Each herbicide was applied foliarly with nonionic surfactant in a spray volume of 374 L/ha. The herbicide response for individual plants was determined by comparing to untreated plants of similar genetic background. Visual injury was scored on a scale of 0 to 100% injury (0=no effect to 100=dead plant). The lowest response for four treated plants of a single event from each construct with the listed expression cassette is reported.

TABLE 9

Herbicide tolerance shown by homozygous soybean transgenic plants overexpressing ALS variant genes

| SEQ ID NO | ALS Variant | Lowest % injury | | | | |
|---|---|---|---|---|---|---|
| | | Chlorimuron | Tribenuron-methyl | Thifensulfuron-methyl | Rimsulfuron | Imazapyr |
|  | No transgene | 40% | 90% | 50% | 95% | 85% |
| 1 | UBQ10: GM-ALS1 | 85% | 95% | 85% | 95% | 85% |
| 10 | SAMS: GM-ALS_P178A_W555L |  | 75% |  |  |  |
| 9 | UBQ10: GM-ALS_P178A | 10% | 20% | 25% | 80% | 10% |
| 15 | UBQ10: GM-ALS_P178S | 35% | 5% | 15% | 80% | 15% |

TABLE 9-continued

Herbicide tolerance shown by homozygous soybean transgenic plants overexpressing ALS variant genes

| SEQ ID NO | ALS Variant | Lowest % injury | | | | |
|---|---|---|---|---|---|---|
| | | Chlorimuron | Tribenuron-methyl | Thifensulfuron-methyl | Rimsulfuron | Imazapyr |
| 17 | UBQ10: GM-ALS_P178S_D357E | 20% | 20% | 20% | 70% | 40% |
| 7 | UBQ10: GM-ALS_A103T_P178S | 35% | 65% | 35% | 80% | 45% |
| 26 | UBQ10: GM-ALS_W555L | 5% | | 5% | 80% | 10% |
| 8 | UBQ10: GM-ALS_A103T_P178S_D357E | 5% | 55% | 0% | 80% | 50% |
| 9 | SAMS: GM-ALS_P178A | 0% | 80% | 25% | 80% | |

Example 10

Herbicide Spray Field Tests of Transgenic ALS Soybean Plants with ALS-Inhibitor Herbicides Homozygous T3 soybean plants with and without ALS variant transgenes were grown in a field study and sprayed at the V2 to V4 growth stage with a commercial formulation of Affinity Broadspec at 1 oz product per acre (2× typical field rate). Affinity Broadspec contains 25% thifensulfuron and 25% tribenuron by volume. The herbicide was applied foliarly with nonionic surfactant. The herbicide response for individual events was determined by comparing to untreated plants of similar genetic background. Visual injury is on a scale of 0 to 100% injury (0=no effect to 100=dead plant).

The substituted ALS variants gave substantially more protection to ALS-inhibitors than overexpression of the native ALS gene.

TABLE 10

Tribenuron and thifensulfuron tolerance shown by homozygous T3 soybean transgenic plants overexpressing ALS variant genes

| SEQ ID NO | ALS Variant | Lowest % injury |
|---|---|---|
| 1 | UBQ10: GM-ALS1 | 93% |
| 10 | SAMS: GM-ALS_P178A_W555L | 5% |
| 9 | UBQ10: GM-ALS_P178A | 7% |
| 15 | UBQ10: GM-ALS_P178S | 5% |
| 17 | UBQ10: GM-ALS_P178S_D357E | 13% |
| 7 | UBQ10: GM-ALS_A103T_P178S | 57% |

What is claimed is:

1. A method of producing an ALS inhibitor-tolerant soybean plant cell comprising:
    a) transforming a soybean plant cell with a recombinant polynucleotide comprising a nucleotide sequence encoding a soybean acetolactate synthase (ALS) inhibitor-tolerant polypeptide comprising an amino acid sequence that is at least 97.5% identical to SEQ ID NO: 1, wherein the amino acid sequence contains a serine at the amino acid residue corresponding to position 178 of SEQ ID NO: 1, and wherein said polynucleotide is operably linked to an S-adenosylmethionine synthase promoter;
    b) placing said cell in a medium that promotes growth;
    c) regenerating a transgenic plant from said plant cell; and
    d) selecting at least one plant produced from said cell that is tolerant to at least one ALS inhibitor in the imidazolinone class, wherein said plant produces at least one seed with less than 0.5% C17 fatty acids relative to the total amount of fatty acids present in the seed.

2. The method of claim 1, wherein said transforming the plant cell results in the stable integration of the polynucleotide into the genome of the plant cell.

3. The method of claim 1, wherein the ALS inhibitor-tolerant polypeptide comprises the amino acid sequence of SEQ ID NO: 15.

4. The method of claim 1, wherein the at least one ALS inhibitor is an imazapyr.

* * * * *

SEQUENCE LISTING

```
<160> NUMBER OF SEQ ID NOS: 28

<210> SEQ ID NO 1
<211> LENGTH: 651
<212> TYPE: PRT
<213> ORGANISM: GLYCINE MAX

<400> SEQUENCE: 1

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
                20                  25                  30

His Gln Thr Leu Thr Lys Pro Asn His Ala Leu Lys Ile Lys Cys Ser
            35                  40                  45

Ile Ser Lys Pro Pro Thr Ala Ala Pro Phe Thr Lys Glu Ala Pro Thr
        50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
            100                 105                 110

Arg Ser Ala Ala Ile Arg Asn Val Leu Pro Arg His Glu Gln Gly Gly
        115                 120                 125

Val Phe Ala Ala Glu Gly Tyr Ala Arg Ser Ser Gly Leu Pro Gly Val
    130                 135                 140

Cys Ile Ala Thr Ser Gly Pro Gly Ala Thr Asn Leu Val Ser Gly Leu
145                 150                 155                 160
```

```
Ala Asp Ala Leu Met Asp Ser Val Pro Val Ala Ile Thr Gly Gln
            165                 170                 175

Val Pro Arg Arg Met Ile Gly Thr Asp Ala Phe Gln Glu Thr Pro Ile
            180                 185                 190

Val Glu Val Ser Arg Ser Ile Thr Lys His Asn Tyr Leu Ile Leu Asp
            195                 200                 205

Val Asp Asp Ile Pro Arg Val Ala Glu Ala Phe Phe Val Ala Thr
    210                 215                 220

Ser Gly Arg Pro Gly Pro Val Leu Ile Asp Pro Lys Asp Val Gln
225                 230                 235                 240

Gln Gln Leu Ala Val Pro Asn Trp Asp Glu Pro Val Asn Leu Pro Gly
            245                 250                 255

Tyr Leu Ala Arg Leu Pro Arg Pro Ala Glu Ala Gln Leu Glu His
            260                 265                 270

Ile Val Arg Leu Ile Met Glu Ala Gln Lys Pro Val Leu Tyr Val Gly
            275                 280                 285

Gly Gly Ser Leu Asn Ser Ser Ala Glu Leu Arg Arg Phe Val Glu Leu
            290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
            325                 330                 335

Tyr Ala Asn Tyr Ala Val Asp Asn Ser Asp Leu Leu Leu Ala Phe Gly
            340                 345                 350

Val Arg Phe Asp Asp Arg Val Thr Gly Lys Leu Glu Ala Phe Ala Ser
            355                 360                 365

Arg Ala Lys Ile Val His Ile Asp Ile Asp Ser Ala Glu Ile Gly Lys
            370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
            405                 410                 415

Asp Leu Gly Gly Trp Arg Glu Glu Ile Asn Val Gln Lys His Lys Phe
            420                 425                 430

Pro Leu Gly Tyr Lys Thr Phe Gln Asp Ala Ile Ser Pro Gln His Ala
            435                 440                 445

Ile Glu Val Leu Asp Glu Leu Thr Asn Gly Asp Ala Ile Val Ser Thr
            450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
            485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
            515                 520                 525

Leu Ala Thr Ile Arg Val Glu Asn Leu Pro Val Lys Ile Leu Leu Leu
            530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
            565                 570                 575

Glu Ile Phe Pro Asn Met Leu Lys Phe Ala Asp Ala Cys Gly Ile Pro
```

```
                    580              585              590
Ala Ala Arg Val Thr Lys Lys Glu Glu Leu Arg Ala Ala Ile Gln Arg
                595              600              605

Met Leu Asp Thr Pro Gly Pro Tyr Leu Leu Asp Val Ile Val Pro His
    610              615              620

Gln Glu His Val Leu Pro Met Ile Pro Ser Asn Gly Ser Phe Lys Asp
625              630              635              640

Val Ile Thr Glu Gly Asp Gly Arg Thr Arg Tyr
                645              650

<210> SEQ ID NO 2
<211> LENGTH: 651
<212> TYPE: PRT
<213> ORGANISM: ARTIFICIAL
<220> FEATURE:
<223> OTHER INFORMATION: ALS1 variant G102S

<400> SEQUENCE: 2

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
                20                  25                  30

His Gln Thr Leu Thr Lys Pro Asn His Ala Leu Lys Ile Lys Cys Ser
            35                  40                  45

Ile Ser Lys Pro Pro Thr Ala Ala Pro Phe Thr Lys Glu Ala Pro Thr
        50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Ser Ala Ser Met Glu Ile His Gln Ala Leu Thr
                100                 105                 110

Arg Ser Ala Ala Ile Arg Asn Val Leu Pro Arg His Glu Gln Gly Gly
            115                 120                 125

Val Phe Ala Ala Glu Gly Tyr Ala Arg Ser Ser Gly Leu Pro Gly Val
        130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Pro Arg Arg Met Ile Gly Thr Asp Ala Phe Gln Glu Thr Pro Ile
            180                 185                 190

Val Glu Val Ser Arg Ser Ile Thr Lys His Asn Tyr Leu Ile Leu Asp
        195                 200                 205

Val Asp Asp Ile Pro Arg Val Val Ala Glu Ala Phe Phe Val Ala Thr
    210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Ala Glu Ala Gln Leu Glu His
            260                 265                 270

Ile Val Arg Leu Ile Met Glu Ala Gln Lys Pro Val Leu Tyr Val Gly
        275                 280                 285

Gly Gly Ser Leu Asn Ser Ser Ala Glu Leu Arg Arg Phe Val Glu Leu
```

```
            290                 295                 300
Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
            340                 345                 350

Val Arg Phe Asp Asp Arg Val Thr Gly Lys Leu Glu Ala Phe Ala Ser
        355                 360                 365

Arg Ala Lys Ile Val His Ile Asp Ile Asp Ser Ala Glu Ile Gly Lys
    370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
            420                 425                 430

Pro Leu Gly Tyr Lys Thr Phe Gln Asp Ala Ile Ser Pro Gln His Ala
        435                 440                 445

Ile Glu Val Leu Asp Glu Leu Thr Asn Gly Asp Ala Ile Val Ser Thr
    450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
        515                 520                 525

Leu Ala Thr Ile Arg Val Glu Asn Leu Pro Val Lys Ile Leu Leu Leu
    530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
            580                 585                 590

Ala Ala Arg Val Thr Lys Lys Glu Glu Leu Arg Ala Ala Ile Gln Arg
        595                 600                 605

Met Leu Asp Thr Pro Gly Pro Tyr Leu Leu Asp Val Ile Val Pro His
    610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 3
<211> LENGTH: 651
<212> TYPE: PRT
<213> ORGANISM: ARTIFICIAL
<220> FEATURE:
<223> OTHER INFORMATION: ALS1 variant G102S P178S

<400> SEQUENCE: 3

Met Ala Ala Thr Ala Ser Arg Thr Thr Arg Phe Ser Ser Ser Ser Ser
```

```
                -continued 1               5               10              15
His Pro Thr Phe Pro Lys Arg Ile Thr Arg Ser Thr Leu Pro Leu Ser
                20              25              30
His Gln Thr Leu Thr Lys Pro Asn His Ala Leu Lys Ile Lys Cys Ser
                35              40              45
Ile Ser Lys Pro Pro Thr Ala Ala Pro Phe Thr Lys Glu Ala Pro Thr
            50              55              60
Thr Glu Pro Phe Val Ser Arg Phe Ala Ser Gly Glu Pro Arg Lys Gly
65              70              75              80
Ala Asp Ile Leu Val Glu Ala Leu Glu Arg Gln Gly Val Thr Thr Val
                85              90              95
Phe Ala Tyr Pro Gly Ser Ala Ser Met Glu Ile His Gln Ala Leu Thr
                100             105             110
Arg Ser Ala Ala Ile Arg Asn Val Leu Pro Arg His Glu Gln Gly Gly
                115             120             125
Val Phe Ala Ala Glu Gly Tyr Ala Arg Ser Ser Gly Leu Pro Gly Val
                130             135             140
Cys Ile Ala Thr Ser Gly Pro Gly Ala Thr Asn Leu Val Ser Gly Leu
145             150             155             160
Ala Asp Ala Leu Met Asp Ser Val Pro Val Val Ala Ile Thr Gly Gln
                165             170             175
Val Ser Arg Arg Met Ile Gly Thr Asp Ala Phe Gln Glu Thr Pro Ile
                180             185             190
Val Glu Val Ser Arg Ser Ile Thr Lys His Asn Tyr Leu Ile Leu Asp
                195             200             205
Val Asp Asp Ile Pro Arg Val Val Ala Glu Ala Phe Phe Val Ala Thr
                210             215             220
Ser Gly Arg Pro Gly Pro Val Leu Ile Asp Ile Pro Lys Asp Val Gln
225             230             235             240
Gln Gln Leu Ala Val Pro Asn Trp Asp Glu Pro Val Asn Leu Pro Gly
                245             250             255
Tyr Leu Ala Arg Leu Pro Arg Pro Ala Glu Ala Gln Leu Glu His
                260             265             270
Ile Val Arg Leu Ile Met Glu Ala Gln Lys Pro Val Leu Tyr Val Gly
                275             280             285
Gly Gly Ser Leu Asn Ser Ser Ala Glu Leu Arg Arg Phe Val Glu Leu
                290             295             300
Thr Gly Ile Pro Val Ala Ser Thr Leu Met Gly Leu Gly Thr Phe Pro
305             310             315             320
Ile Gly Asp Glu Tyr Ser Leu Gln Met Leu Gly Met His Gly Thr Val
                325             330             335
Tyr Ala Asn Tyr Ala Val Asp Asn Ser Asp Leu Leu Leu Ala Phe Gly
                340             345             350
Val Arg Phe Asp Asp Arg Val Thr Gly Lys Leu Glu Ala Phe Ala Ser
                355             360             365
Arg Ala Lys Ile Val His Ile Asp Ile Asp Ser Ala Glu Ile Gly Lys
                370             375             380
Asn Lys Gln Ala His Val Ser Val Cys Ala Asp Leu Lys Leu Ala Leu
385             390             395             400
Lys Gly Ile Asn Met Ile Leu Glu Glu Lys Gly Val Glu Gly Lys Phe
                405             410             415
Asp Leu Gly Gly Trp Arg Glu Glu Ile Asn Val Gln Lys His Lys Phe
                420             425             430
```

```
              Pro Leu Gly Tyr Lys Thr Phe Gln Asp Ala Ile Ser Pro Gln His Ala
                      435                 440                 445

Ile Glu Val Leu Asp Glu Leu Thr Asn Gly Asp Ala Ile Val Ser Thr
                  450                 455                 460

Gly Val Gly Gln His Gln Met Trp Ala Ala Gln Phe Tyr Lys Tyr Lys
              465                 470                 475                 480

Arg Pro Arg Gln Trp Leu Thr Ser Gly Leu Gly Ala Met Gly Phe
                              485                 490                 495

Gly Leu Pro Ala Ala Ile Gly Ala Ala Val Ala Asn Pro Gly Ala Val
                              500                 505                 510

Val Val Asp Ile Asp Gly Asp Gly Ser Phe Ile Met Asn Val Gln Glu
                              515                 520                 525

Leu Ala Thr Ile Arg Val Glu Asn Leu Pro Val Lys Ile Leu Leu Leu
                      530                 535                 540

Asn Asn Gln His Leu Gly Met Val Val Gln Trp Glu Asp Arg Phe Tyr
              545                 550                 555                 560

Lys Ser Asn Arg Ala His Thr Tyr Leu Gly Asp Pro Ser Ser Glu Ser
                              565                 570                 575

Glu Ile Phe Pro Asn Met Leu Lys Phe Ala Asp Ala Cys Gly Ile Pro
                              580                 585                 590

Ala Ala Arg Val Thr Lys Lys Glu Glu Leu Arg Ala Ala Ile Gln Arg
                      595                 600                 605

Met Leu Asp Thr Pro Gly Pro Tyr Leu Leu Asp Val Ile Val Pro His
                      610                 615                 620

Gln Glu His Val Leu Pro Met Ile Pro Ser Asn Gly Ser Phe Lys Asp
              625                 630                 635                 640

Val Ile Thr Glu Gly Asp Gly Arg Thr Arg Tyr
                              645                 650

<210> SEQ ID NO 4
<211> LENGTH: 651
<212> TYPE: PRT
<213> ORGANISM: ARTIFICIAL
<220> FEATURE:
<223> OTHER INFORMATION: ALS1 variant G102S D357E

<400> SEQUENCE: 4

Met Ala Ala Thr Ala Ser Arg Thr Thr Arg Phe Ser Ser Ser Ser Ser
              1               5                   10                  15

His Pro Thr Phe Pro Lys Arg Ile Thr Arg Ser Thr Leu Pro Leu Ser
                              20                  25                  30

His Gln Thr Leu Thr Lys Pro Asn His Ala Leu Lys Ile Lys Cys Ser
                      35                  40                  45

Ile Ser Lys Pro Pro Thr Ala Ala Pro Phe Thr Lys Glu Ala Pro Thr
                  50                  55                  60

Thr Glu Pro Phe Val Ser Arg Phe Ala Ser Gly Glu Pro Arg Lys Gly
              65                  70                  75                  80

Ala Asp Ile Leu Val Glu Ala Leu Glu Arg Gln Gly Val Thr Thr Val
                              85                  90                  95

Phe Ala Tyr Pro Gly Ser Ala Ser Met Glu Ile His Gln Ala Leu Thr
                              100                 105                 110

Arg Ser Ala Ala Ile Arg Asn Val Leu Pro Arg His Glu Gln Gly Gly
                      115                 120                 125

Val Phe Ala Ala Glu Gly Tyr Ala Arg Ser Ser Gly Leu Pro Gly Val
                      130                 135                 140
```

-continued

```
Cys Ile Ala Thr Ser Gly Pro Gly Ala Thr Asn Leu Val Ser Gly Leu
145                 150                 155                 160

Ala Asp Ala Leu Met Asp Ser Val Pro Val Ala Ile Thr Gly Gln
            165                 170                 175

Val Pro Arg Arg Met Ile Gly Thr Asp Ala Phe Gln Glu Thr Pro Ile
            180                 185                 190

Val Glu Val Ser Arg Ser Ile Thr Lys His Asn Tyr Leu Ile Leu Asp
            195                 200                 205

Val Asp Asp Ile Pro Arg Val Val Ala Glu Ala Phe Phe Val Ala Thr
210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
            245                 250                 255

Tyr Leu Ala Arg Leu Pro Arg Pro Ala Glu Ala Gln Leu Glu His
            260                 265                 270

Ile Val Arg Leu Ile Met Glu Ala Gln Lys Pro Val Leu Tyr Val Gly
            275                 280                 285

Gly Gly Ser Leu Asn Ser Ser Ala Glu Leu Arg Arg Phe Val Glu Leu
290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
            325                 330                 335

Tyr Ala Asn Tyr Ala Val Asp Asn Ser Asp Leu Leu Leu Ala Phe Gly
            340                 345                 350

Val Arg Phe Asp Glu Arg Val Thr Gly Lys Leu Glu Ala Phe Ala Ser
            355                 360                 365

Arg Ala Lys Ile Val His Ile Asp Ile Asp Ser Ala Glu Ile Gly Lys
370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
            405                 410                 415

Asp Leu Gly Gly Trp Arg Glu Glu Ile Asn Val Gln Lys His Lys Phe
            420                 425                 430

Pro Leu Gly Tyr Lys Thr Phe Gln Asp Ala Ile Ser Pro Gln His Ala
            435                 440                 445

Ile Glu Val Leu Asp Glu Leu Thr Asn Gly Asp Ala Ile Val Ser Thr
450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
            485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
            515                 520                 525

Leu Ala Thr Ile Arg Val Glu Asn Leu Pro Val Lys Ile Leu Leu Leu
530                 535                 540

Asn Asn Gln His Leu Gly Met Val Val Gln Trp Glu Asp Arg Phe Tyr
545                 550                 555                 560
```

```
Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
                580                 585                 590

Ala Ala Arg Val Thr Lys Lys Glu Glu Leu Arg Ala Ala Ile Gln Arg
                595                 600                 605

Met Leu Asp Thr Pro Gly Pro Tyr Leu Leu Asp Val Ile Val Pro His
                610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 5
<211> LENGTH: 651
<212> TYPE: PRT
<213> ORGANISM: ARTIFICIAL
<220> FEATURE:
<223> OTHER INFORMATION: ALS1 variant G102S D357N

<400> SEQUENCE: 5

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
                20                  25                  30

His Gln Thr Leu Thr Lys Pro Asn His Ala Leu Lys Ile Lys Cys Ser
                35                  40                  45

Ile Ser Lys Pro Pro Thr Ala Ala Pro Phe Thr Lys Glu Ala Pro Thr
50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Ser Ala Ser Met Glu Ile His Gln Ala Leu Thr
                100                 105                 110

Arg Ser Ala Ala Ile Arg Asn Val Leu Pro Arg His Glu Gln Gly Gly
                115                 120                 125

Val Phe Ala Ala Glu Gly Tyr Ala Arg Ser Ser Gly Leu Pro Gly Val
                130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Pro Arg Arg Met Ile Gly Thr Asp Ala Phe Gln Glu Thr Pro Ile
                180                 185                 190

Val Glu Val Ser Arg Ser Ile Thr Lys His Asn Tyr Leu Ile Leu Asp
                195                 200                 205

Val Asp Asp Ile Pro Arg Val Val Ala Glu Ala Phe Phe Val Ala Thr
                210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Pro Ala Glu Ala Gln Leu Glu His
                260                 265                 270
```

```
Ile Val Arg Leu Ile Met Glu Ala Gln Lys Pro Val Leu Tyr Val Gly
            275                 280                 285

Gly Gly Ser Leu Asn Ser Ser Ala Glu Leu Arg Arg Phe Val Glu Leu
        290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
            340                 345                 350

Val Arg Phe Asp Asn Arg Val Thr Gly Lys Leu Glu Ala Phe Ala Ser
        355                 360                 365

Arg Ala Lys Ile Val His Ile Asp Ile Asp Ser Ala Glu Ile Gly Lys
370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
            420                 425                 430

Pro Leu Gly Tyr Lys Thr Phe Gln Asp Ala Ile Ser Pro Gln His Ala
        435                 440                 445

Ile Glu Val Leu Asp Glu Leu Thr Asn Gly Asp Ala Ile Val Ser Thr
450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
        515                 520                 525

Leu Ala Thr Ile Arg Val Glu Asn Leu Pro Val Lys Ile Leu Leu Leu
530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
            580                 585                 590

Ala Ala Arg Val Thr Lys Lys Glu Glu Leu Arg Ala Ala Ile Gln Arg
        595                 600                 605

Met Leu Asp Thr Pro Gly Pro Tyr Leu Leu Asp Val Ile Val Pro His
610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 6
<211> LENGTH: 651
<212> TYPE: PRT
<213> ORGANISM: ARTIFICIAL
<220> FEATURE:
<223> OTHER INFORMATION: ALS1 variant A103T
```

<400> SEQUENCE: 6

```
Met Ala Ala Thr Ala Ser Arg Thr Thr Arg Phe Ser Ser Ser Ser
1               5                   10                  15

His Pro Thr Phe Pro Lys Arg Ile Thr Arg Ser Thr Leu Pro Leu Ser
            20                  25                  30

His Gln Thr Leu Thr Lys Pro Asn His Ala Leu Lys Ile Lys Cys Ser
        35                  40                  45

Ile Ser Lys Pro Pro Thr Ala Ala Pro Phe Thr Lys Glu Ala Pro Thr
    50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Thr Ser Met Glu Ile His Gln Ala Leu Thr
            100                 105                 110

Arg Ser Ala Ala Ile Arg Asn Val Leu Pro Arg His Glu Gln Gly Gly
        115                 120                 125

Val Phe Ala Ala Glu Gly Tyr Ala Arg Ser Ser Gly Leu Pro Gly Val
    130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Pro Arg Arg Met Ile Gly Thr Asp Ala Phe Gln Glu Thr Pro Ile
            180                 185                 190

Val Glu Val Ser Arg Ser Ile Thr Lys His Asn Tyr Leu Ile Leu Asp
    195                 200                 205

Val Asp Asp Ile Pro Arg Val Val Ala Glu Ala Phe Phe Val Ala Thr
210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Ala Glu Ala Gln Leu Glu His
            260                 265                 270

Ile Val Arg Leu Ile Met Glu Ala Gln Lys Pro Val Leu Tyr Val Gly
        275                 280                 285

Gly Gly Ser Leu Asn Ser Ser Ala Glu Leu Arg Arg Phe Val Glu Leu
    290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
            340                 345                 350

Val Arg Phe Asp Asp Arg Val Thr Gly Lys Leu Glu Ala Phe Ala Ser
        355                 360                 365

Arg Ala Lys Ile Val His Ile Asp Ile Asp Ser Ala Glu Ile Gly Lys
    370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
```

```
                    405                 410                 415
Asp Leu Gly Gly Trp Arg Glu Glu Ile Asn Val Gln Lys His Lys Phe
            420                 425                 430

Pro Leu Gly Tyr Lys Thr Phe Gln Asp Ala Ile Ser Pro Gln His Ala
            435                 440                 445

Ile Glu Val Leu Asp Glu Leu Thr Asn Gly Asp Ala Ile Val Ser Thr
            450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
            515                 520                 525

Leu Ala Thr Ile Arg Val Glu Asn Leu Pro Val Lys Ile Leu Leu Leu
            530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
            580                 585                 590

Ala Ala Arg Val Thr Lys Lys Glu Glu Leu Arg Ala Ala Ile Gln Arg
            595                 600                 605

Met Leu Asp Thr Pro Gly Pro Tyr Leu Leu Asp Val Ile Val Pro His
610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 7
<211> LENGTH: 651
<212> TYPE: PRT
<213> ORGANISM: ARTIFICIAL
<220> FEATURE:
<223> OTHER INFORMATION: ALS1 variant A103T P178S

<400> SEQUENCE: 7

Met Ala Ala Thr Ala Ser Arg Thr Arg Phe Ser Ser Ser Ser Ser
1               5                   10                  15

His Pro Thr Phe Pro Lys Arg Ile Thr Arg Ser Thr Leu Pro Leu Ser
            20                  25                  30

His Gln Thr Leu Thr Lys Pro Asn His Ala Leu Lys Ile Lys Cys Ser
        35                  40                  45

Ile Ser Lys Pro Pro Thr Ala Pro Phe Thr Lys Glu Ala Pro Thr
    50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
            85                  90                  95

Phe Ala Tyr Pro Gly Gly Thr Ser Met Glu Ile His Gln Ala Leu Thr
            100                 105                 110

Arg Ser Ala Ala Ile Arg Asn Val Leu Pro Arg His Glu Gln Gly Gly
```

```
            115                 120                 125
Val Phe Ala Ala Glu Gly Tyr Ala Arg Ser Ser Gly Leu Pro Gly Val
            130                 135                 140
Cys Ile Ala Thr Ser Gly Pro Gly Ala Thr Asn Leu Val Ser Gly Leu
145                 150                 155                 160
Ala Asp Ala Leu Met Asp Ser Val Pro Val Ala Ile Thr Gly Gln
                165                 170                 175
Val Ser Arg Arg Met Ile Gly Thr Asp Ala Phe Gln Glu Thr Pro Ile
                180                 185                 190
Val Glu Val Ser Arg Ser Ile Thr Lys His Asn Tyr Leu Ile Leu Asp
                195                 200                 205
Val Asp Asp Ile Pro Arg Val Val Ala Glu Ala Phe Phe Val Ala Thr
            210                 215                 220
Ser Gly Arg Pro Gly Pro Val Leu Ile Asp Ile Pro Lys Asp Val Gln
225                 230                 235                 240
Gln Gln Leu Ala Val Pro Asn Trp Asp Glu Pro Val Asn Leu Pro Gly
                245                 250                 255
Tyr Leu Ala Arg Leu Pro Arg Pro Ala Glu Ala Gln Leu Glu His
            260                 265                 270
Ile Val Arg Leu Ile Met Glu Ala Gln Lys Pro Val Leu Tyr Val Gly
            275                 280                 285
Gly Gly Ser Leu Asn Ser Ser Ala Glu Leu Arg Arg Phe Val Glu Leu
            290                 295                 300
Thr Gly Ile Pro Val Ala Ser Thr Leu Met Gly Leu Gly Thr Phe Pro
305                 310                 315                 320
Ile Gly Asp Glu Tyr Ser Leu Gln Met Leu Gly Met His Gly Thr Val
                325                 330                 335
Tyr Ala Asn Tyr Ala Val Asp Asn Ser Asp Leu Leu Leu Ala Phe Gly
                340                 345                 350
Val Arg Phe Asp Asp Arg Val Thr Gly Lys Leu Glu Ala Phe Ala Ser
                355                 360                 365
Arg Ala Lys Ile Val His Ile Asp Ile Asp Ser Ala Glu Ile Gly Lys
            370                 375                 380
Asn Lys Gln Ala His Val Ser Val Cys Ala Asp Leu Lys Leu Ala Leu
385                 390                 395                 400
Lys Gly Ile Asn Met Ile Leu Glu Glu Lys Gly Val Glu Gly Lys Phe
                405                 410                 415
Asp Leu Gly Gly Trp Arg Glu Glu Ile Asn Val Gln Lys His Lys Phe
                420                 425                 430
Pro Leu Gly Tyr Lys Thr Phe Gln Asp Ala Ile Ser Pro Gln His Ala
            435                 440                 445
Ile Glu Val Leu Asp Glu Leu Thr Asn Gly Asp Ala Ile Val Ser Thr
            450                 455                 460
Gly Val Gly Gln His Gln Met Trp Ala Ala Gln Phe Tyr Lys Tyr Lys
465                 470                 475                 480
Arg Pro Arg Gln Trp Leu Thr Ser Gly Gly Leu Gly Ala Met Gly Phe
                485                 490                 495
Gly Leu Pro Ala Ala Ile Gly Ala Ala Val Ala Asn Pro Gly Ala Val
            500                 505                 510
Val Val Asp Ile Asp Gly Asp Gly Ser Phe Ile Met Asn Val Gln Glu
            515                 520                 525
Leu Ala Thr Ile Arg Val Glu Asn Leu Pro Val Lys Ile Leu Leu Leu
            530                 535                 540
```

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
            565                 570                 575

Glu Ile Phe Pro Asn Met Leu Lys Phe Ala Asp Ala Cys Gly Ile Pro
        580                 585                 590

Ala Ala Arg Val Thr Lys Lys Glu Glu Leu Arg Ala Ala Ile Gln Arg
    595                 600                 605

Met Leu Asp Thr Pro Gly Pro Tyr Leu Leu Asp Val Ile Val Pro His
610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 8
<211> LENGTH: 651
<212> TYPE: PRT
<213> ORGANISM: ARTIFICIAL
<220> FEATURE:
<223> OTHER INFORMATION: ALS1 variant A103T P178S D357E

<400> SEQUENCE: 8

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
            20                  25                  30

His Gln Thr Leu Thr Lys Pro Asn His Ala Leu Lys Ile Lys Cys Ser
        35                  40                  45

Ile Ser Lys Pro Pro Thr Ala Ala Pro Phe Thr Lys Glu Ala Pro Thr
    50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Thr Ser Met Glu Ile His Gln Ala Leu Thr
            100                 105                 110

Arg Ser Ala Ala Ile Arg Asn Val Leu Pro Arg His Glu Gln Gly Gly
        115                 120                 125

Val Phe Ala Ala Glu Gly Tyr Ala Arg Ser Ser Gly Leu Pro Gly Val
    130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Ser Arg Arg Met Ile Gly Thr Asp Ala Phe Gln Glu Thr Pro Ile
            180                 185                 190

Val Glu Val Ser Arg Ser Ile Thr Lys His Asn Tyr Leu Ile Leu Asp
        195                 200                 205

Val Asp Asp Ile Pro Arg Val Val Ala Glu Ala Phe Phe Val Ala Thr
    210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

-continued

```
Tyr Leu Ala Arg Leu Pro Arg Pro Ala Glu Ala Gln Leu Glu His
            260                 265                 270

Ile Val Arg Leu Ile Met Glu Ala Gln Lys Pro Val Leu Tyr Val Gly
        275                 280                 285

Gly Gly Ser Leu Asn Ser Ala Glu Leu Arg Arg Phe Val Glu Leu
    290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Ala Phe Gly
            340                 345                 350

Val Arg Phe Asp Glu Arg Val Thr Gly Lys Leu Glu Ala Phe Ala Ser
        355                 360                 365

Arg Ala Lys Ile Val His Ile Asp Ile Asp Ser Ala Glu Ile Gly Lys
    370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
            420                 425                 430

Pro Leu Gly Tyr Lys Thr Phe Gln Asp Ala Ile Ser Pro Gln His Ala
        435                 440                 445

Ile Glu Val Leu Asp Glu Leu Thr Asn Gly Asp Ala Ile Val Ser Thr
    450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
        515                 520                 525

Leu Ala Thr Ile Arg Val Glu Asn Leu Pro Val Lys Ile Leu Leu Leu
    530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
            580                 585                 590

Ala Ala Arg Val Thr Lys Lys Glu Glu Leu Arg Ala Ala Ile Gln Arg
        595                 600                 605

Met Leu Asp Thr Pro Gly Pro Tyr Leu Leu Asp Val Ile Val Pro His
    610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 9
<211> LENGTH: 651
```

<212> TYPE: PRT
<213> ORGANISM: ARTIFICIAL
<220> FEATURE:
<223> OTHER INFORMATION: ALS1 variant P178A

<400> SEQUENCE: 9

```
Met Ala Ala Thr Ala Ser Arg Thr Thr Arg Phe Ser Ser Ser Ser
 1               5                  10                  15

His Pro Thr Phe Pro Lys Arg Ile Thr Arg Ser Thr Leu Pro Leu Ser
            20                  25                  30

His Gln Thr Leu Thr Lys Pro Asn His Ala Leu Lys Ile Lys Cys Ser
        35                  40                  45

Ile Ser Lys Pro Pro Thr Ala Ala Pro Phe Thr Lys Glu Ala Pro Thr
    50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
            100                 105                 110

Arg Ser Ala Ala Ile Arg Asn Val Leu Pro Arg His Glu Gln Gly Gly
        115                 120                 125

Val Phe Ala Ala Glu Gly Tyr Ala Arg Ser Ser Gly Leu Pro Gly Val
    130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Ala Ile Thr Gly Gln
                165                 170                 175

Val Ala Arg Arg Met Ile Gly Thr Asp Ala Phe Gln Glu Thr Pro Ile
            180                 185                 190

Val Glu Val Ser Arg Ser Ile Thr Lys His Asn Tyr Leu Ile Leu Asp
        195                 200                 205

Val Asp Asp Ile Pro Arg Val Val Ala Glu Ala Phe Phe Val Ala Thr
    210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Ala Glu Ala Gln Leu Glu His
            260                 265                 270

Ile Val Arg Leu Ile Met Glu Ala Gln Lys Pro Val Leu Tyr Val Gly
        275                 280                 285

Gly Gly Ser Leu Asn Ser Ser Ala Glu Leu Arg Arg Phe Val Glu Leu
    290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
            340                 345                 350

Val Arg Phe Asp Asp Arg Val Thr Gly Lys Leu Glu Ala Phe Ala Ser
        355                 360                 365

Arg Ala Lys Ile Val His Ile Asp Ile Asp Ser Ala Glu Ile Gly Lys
    370                 375                 380
```

```
Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
            405                 410                 415

Asp Leu Gly Gly Trp Arg Glu Glu Ile Asn Val Gln Lys His Lys Phe
        420                 425                 430

Pro Leu Gly Tyr Lys Thr Phe Gln Asp Ala Ile Ser Pro Gln His Ala
            435                 440                 445

Ile Glu Val Leu Asp Glu Leu Thr Asn Gly Asp Ala Ile Val Ser Thr
    450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
            515                 520                 525

Leu Ala Thr Ile Arg Val Glu Asn Leu Pro Val Lys Ile Leu Leu Leu
530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
            580                 585                 590

Ala Ala Arg Val Thr Lys Lys Glu Glu Leu Arg Ala Ala Ile Gln Arg
            595                 600                 605

Met Leu Asp Thr Pro Gly Pro Tyr Leu Leu Asp Val Ile Val Pro His
    610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650
```

<210> SEQ ID NO 10
<211> LENGTH: 651
<212> TYPE: PRT
<213> ORGANISM: ARTIFICIAL
<220> FEATURE:
<223> OTHER INFORMATION: ALS1 variant P178A W555L

<400> SEQUENCE: 10

```
Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
            20                  25                  30

His Gln Thr Leu Thr Lys Pro Asn His Ala Leu Lys Ile Lys Cys Ser
        35                  40                  45

Ile Ser Lys Pro Pro Thr Ala Ala Pro Phe Thr Lys Glu Ala Pro Thr
    50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95
```

-continued

Phe Ala Tyr Pro Gly Gly Ala Ser Met Glu Ile His Gln Ala Leu Thr
                100                 105                 110
Arg Ser Ala Ala Ile Arg Asn Val Leu Pro Arg His Glu Gln Gly Gly
            115                 120                 125
Val Phe Ala Ala Glu Gly Tyr Ala Arg Ser Ser Gly Leu Pro Gly Val
        130                 135                 140
Cys Ile Ala Thr Ser Gly Pro Gly Ala Thr Asn Leu Val Ser Gly Leu
145                 150                 155                 160
Ala Asp Ala Leu Met Asp Ser Val Pro Val Val Ala Ile Thr Gly Gln
                165                 170                 175
Val Ala Arg Arg Met Ile Gly Thr Asp Ala Phe Gln Glu Thr Pro Ile
            180                 185                 190
Val Glu Val Ser Arg Ser Ile Thr Lys His Asn Tyr Leu Ile Leu Asp
        195                 200                 205
Val Asp Asp Ile Pro Arg Val Val Ala Glu Ala Phe Phe Val Ala Thr
    210                 215                 220
Ser Gly Arg Pro Gly Pro Val Leu Ile Asp Ile Pro Lys Asp Val Gln
225                 230                 235                 240
Gln Gln Leu Ala Val Pro Asn Trp Asp Glu Pro Val Asn Leu Pro Gly
                245                 250                 255
Tyr Leu Ala Arg Leu Pro Arg Pro Ala Glu Ala Gln Leu Glu His
            260                 265                 270
Ile Val Arg Leu Ile Met Glu Ala Gln Lys Pro Val Leu Tyr Val Gly
        275                 280                 285
Gly Gly Ser Leu Asn Ser Ser Ala Glu Leu Arg Arg Phe Val Glu Leu
    290                 295                 300
Thr Gly Ile Pro Val Ala Ser Thr Leu Met Gly Leu Gly Thr Phe Pro
305                 310                 315                 320
Ile Gly Asp Glu Tyr Ser Leu Gln Met Leu Gly Met His Gly Thr Val
                325                 330                 335
Tyr Ala Asn Tyr Ala Val Asp Asn Ser Asp Leu Leu Leu Ala Phe Gly
            340                 345                 350
Val Arg Phe Asp Asp Arg Val Thr Gly Lys Leu Glu Ala Phe Ala Ser
        355                 360                 365
Arg Ala Lys Ile Val His Ile Asp Ile Asp Ser Ala Glu Ile Gly Lys
    370                 375                 380
Asn Lys Gln Ala His Val Ser Val Cys Ala Asp Leu Lys Leu Ala Leu
385                 390                 395                 400
Lys Gly Ile Asn Met Ile Leu Glu Glu Lys Gly Val Glu Gly Lys Phe
                405                 410                 415
Asp Leu Gly Gly Trp Arg Glu Glu Ile Asn Val Gln Lys His Lys Phe
            420                 425                 430
Pro Leu Gly Tyr Lys Thr Phe Gln Asp Ala Ile Ser Pro Gln His Ala
        435                 440                 445
Ile Glu Val Leu Asp Glu Leu Thr Asn Gly Asp Ala Ile Val Ser Thr
    450                 455                 460
Gly Val Gly Gln His Gln Met Trp Ala Ala Gln Phe Tyr Lys Tyr Lys
465                 470                 475                 480
Arg Pro Arg Gln Trp Leu Thr Ser Gly Gly Leu Gly Ala Met Gly Phe
                485                 490                 495
Gly Leu Pro Ala Ala Ile Gly Ala Ala Val Ala Asn Pro Gly Ala Val
            500                 505                 510
Val Val Asp Ile Asp Gly Asp Gly Ser Phe Ile Met Asn Val Gln Glu

```
              515                 520                 525
Leu Ala Thr Ile Arg Val Glu Asn Leu Pro Val Lys Ile Leu Leu Leu
530                 535                 540

Asn Asn Gln His Leu Gly Met Val Val Gln Leu Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
                580                 585                 590

Ala Ala Arg Val Thr Lys Lys Glu Glu Leu Arg Ala Ile Gln Arg
                595                 600                 605

Met Leu Asp Thr Pro Gly Pro Tyr Leu Leu Asp Val Ile Val Pro His
610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650
```

<210> SEQ ID NO 11
<211> LENGTH: 651
<212> TYPE: PRT
<213> ORGANISM: ARTIFICIAL
<220> FEATURE:
<223> OTHER INFORMATION: ALS1 variant P178A F559D

<400> SEQUENCE: 11

```
Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
                20                  25                  30

His Gln Thr Leu Thr Lys Pro Asn His Ala Leu Lys Ile Lys Cys Ser
            35                  40                  45

Ile Ser Lys Pro Pro Thr Ala Ala Pro Phe Thr Lys Glu Ala Pro Thr
        50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
                100                 105                 110

Arg Ser Ala Ala Ile Arg Asn Val Leu Pro Arg His Glu Gln Gly Gly
            115                 120                 125

Val Phe Ala Ala Glu Gly Tyr Ala Arg Ser Ser Gly Leu Pro Gly Val
        130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Ala Arg Arg Met Ile Gly Thr Asp Ala Phe Gln Glu Thr Pro Ile
                180                 185                 190

Val Glu Val Ser Arg Ser Ile Thr Lys His Asn Tyr Leu Ile Leu Asp
            195                 200                 205

Val Asp Asp Ile Pro Arg Val Val Ala Glu Ala Phe Phe Val Ala Thr
        210                 215                 220

Ser Gly Arg Pro Gly Pro Val Leu Ile Asp Ile Pro Lys Asp Val Gln
```

```
            225                 230                 235                 240
    Gln Gln Leu Ala Val Pro Asn Trp Asp Glu Pro Val Asn Leu Pro Gly
                    245                 250                 255
    Tyr Leu Ala Arg Leu Pro Arg Pro Pro Ala Glu Ala Gln Leu Glu His
                    260                 265                 270
    Ile Val Arg Leu Ile Met Glu Ala Gln Lys Pro Val Leu Tyr Val Gly
                    275                 280                 285
    Gly Gly Ser Leu Asn Ser Ser Ala Glu Leu Arg Arg Phe Val Glu Leu
                    290                 295                 300
    Thr Gly Ile Pro Val Ala Ser Thr Leu Met Gly Leu Gly Thr Phe Pro
    305                 310                 315                 320
    Ile Gly Asp Glu Tyr Ser Leu Gln Met Leu Gly Met His Gly Thr Val
                    325                 330                 335
    Tyr Ala Asn Tyr Ala Val Asp Asn Ser Asp Leu Leu Leu Ala Phe Gly
                    340                 345                 350
    Val Arg Phe Asp Asp Arg Val Thr Gly Lys Leu Glu Ala Phe Ala Ser
                    355                 360                 365
    Arg Ala Lys Ile Val His Ile Asp Ile Asp Ser Ala Glu Ile Gly Lys
                    370                 375                 380
    Asn Lys Gln Ala His Val Ser Val Cys Ala Asp Leu Lys Leu Ala Leu
    385                 390                 395                 400
    Lys Gly Ile Asn Met Ile Leu Glu Glu Lys Gly Val Glu Gly Lys Phe
                    405                 410                 415
    Asp Leu Gly Gly Trp Arg Glu Glu Ile Asn Val Gln Lys His Lys Phe
                    420                 425                 430
    Pro Leu Gly Tyr Lys Thr Phe Gln Asp Ala Ile Ser Pro Gln His Ala
                    435                 440                 445
    Ile Glu Val Leu Asp Glu Leu Thr Asn Gly Asp Ala Ile Val Ser Thr
                    450                 455                 460
    Gly Val Gly Gln His Gln Met Trp Ala Ala Gln Phe Tyr Lys Tyr Lys
    465                 470                 475                 480
    Arg Pro Arg Gln Trp Leu Thr Ser Gly Gly Leu Gly Ala Met Gly Phe
                    485                 490                 495
    Gly Leu Pro Ala Ala Ile Gly Ala Ala Val Ala Asn Pro Gly Ala Val
                    500                 505                 510
    Val Val Asp Ile Asp Gly Asp Gly Ser Phe Ile Met Asn Val Gln Glu
                    515                 520                 525
    Leu Ala Thr Ile Arg Val Glu Asn Leu Pro Val Lys Ile Leu Leu Leu
                    530                 535                 540
    Asn Asn Gln His Leu Gly Met Val Val Gln Trp Glu Asp Arg Asp Tyr
    545                 550                 555                 560
    Lys Ser Asn Arg Ala His Thr Tyr Leu Gly Asp Pro Ser Ser Glu Ser
                    565                 570                 575
    Glu Ile Phe Pro Asn Met Leu Lys Phe Ala Asp Ala Cys Gly Ile Pro
                    580                 585                 590
    Ala Ala Arg Val Thr Lys Lys Glu Glu Leu Arg Ala Ala Ile Gln Arg
                    595                 600                 605
    Met Leu Asp Thr Pro Gly Pro Tyr Leu Leu Asp Val Ile Val Pro His
                    610                 615                 620
    Gln Glu His Val Leu Pro Met Ile Pro Ser Asn Gly Ser Phe Lys Asp
    625                 630                 635                 640
    Val Ile Thr Glu Gly Asp Gly Arg Thr Arg Tyr
                    645                 650
```

<210> SEQ ID NO 12
<211> LENGTH: 651
<212> TYPE: PRT
<213> ORGANISM: ARTIFICIAL
<220> FEATURE:
<223> OTHER INFORMATION: ALS1 variant P178L

<400> SEQUENCE: 12

```
Met Ala Ala Thr Ala Ser Arg Thr Thr Arg Phe Ser Ser Ser Ser
1               5                   10                  15

His Pro Thr Phe Pro Lys Arg Ile Thr Arg Ser Thr Leu Pro Leu Ser
            20                  25                  30

His Gln Thr Leu Thr Lys Pro Asn His Ala Leu Lys Ile Lys Cys Ser
            35                  40                  45

Ile Ser Lys Pro Pro Thr Ala Ala Pro Phe Thr Lys Glu Ala Pro Thr
50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
            100                 105                 110

Arg Ser Ala Ala Ile Arg Asn Val Leu Pro Arg His Glu Gln Gly Gly
            115                 120                 125

Val Phe Ala Ala Glu Gly Tyr Ala Arg Ser Ser Gly Leu Pro Gly Val
            130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Leu Arg Arg Met Ile Gly Thr Asp Ala Phe Gln Glu Thr Pro Ile
            180                 185                 190

Val Glu Val Ser Arg Ser Ile Thr Lys His Asn Tyr Leu Ile Leu Asp
            195                 200                 205

Val Asp Asp Ile Pro Arg Val Val Ala Glu Ala Phe Phe Val Ala Thr
210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Pro Ala Glu Ala Gln Leu Glu His
            260                 265                 270

Ile Val Arg Leu Ile Met Glu Ala Gln Lys Pro Val Leu Tyr Val Gly
            275                 280                 285

Gly Gly Ser Leu Asn Ser Ser Ala Glu Leu Arg Arg Phe Val Glu Leu
            290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
            340                 345                 350

Val Arg Phe Asp Asp Arg Val Thr Gly Lys Leu Glu Ala Phe Ala Ser
            355                 360                 365
```

```
Arg Ala Lys Ile Val His Ile Asp Ile Asp Ser Ala Glu Ile Gly Lys
        370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
                420                 425                 430

Pro Leu Gly Tyr Lys Thr Phe Gln Asp Ala Ile Ser Pro Gln His Ala
                435                 440                 445

Ile Glu Val Leu Asp Glu Leu Thr Asn Gly Asp Ala Ile Val Ser Thr
        450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
                500                 505                 510

Val Val Asp Ile Asp Gly Asp Gly Ser Phe Ile Met Asn Val Gln Glu
                515                 520                 525

Leu Ala Thr Ile Arg Val Glu Asn Leu Pro Val Lys Ile Leu Leu Leu
        530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
                580                 585                 590

Ala Ala Arg Val Thr Lys Lys Glu Glu Leu Arg Ala Ala Ile Gln Arg
                595                 600                 605

Met Leu Asp Thr Pro Gly Pro Tyr Leu Leu Asp Val Ile Val Pro His
        610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650
```

<210> SEQ ID NO 13
<211> LENGTH: 651
<212> TYPE: PRT
<213> ORGANISM: ARTIFICIAL
<220> FEATURE:
<223> OTHER INFORMATION: ALS1 variant P178L W555L

<400> SEQUENCE: 13

```
Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
                20                  25                  30

His Gln Thr Leu Thr Lys Pro Asn His Ala Leu Lys Ile Lys Cys Ser
            35                  40                  45

Ile Ser Lys Pro Pro Thr Ala Ala Pro Phe Lys Glu Ala Pro Thr
        50                  55                  60

Thr Glu Pro Phe Val Ser Arg Phe Ala Ser Gly Glu Pro Arg Lys Gly
65                  70                  75                  80
```

```
Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
                100                 105                 110

Arg Ser Ala Ala Ile Arg Asn Val Leu Pro Arg His Glu Gln Gly Gly
                115                 120                 125

Val Phe Ala Ala Glu Gly Tyr Ala Arg Ser Ser Gly Leu Pro Gly Val
                130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Leu Arg Arg Met Ile Gly Thr Asp Ala Phe Gln Glu Thr Pro Ile
                180                 185                 190

Val Glu Val Ser Arg Ser Ile Thr Lys His Asn Tyr Leu Ile Leu Asp
                195                 200                 205

Val Asp Asp Ile Pro Arg Val Val Ala Glu Ala Phe Phe Val Ala Thr
                210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Ala Glu Ala Gln Leu Glu His
                260                 265                 270

Ile Val Arg Leu Ile Met Glu Ala Gln Lys Pro Val Leu Tyr Val Gly
                275                 280                 285

Gly Gly Ser Leu Asn Ser Ser Ala Glu Leu Arg Arg Phe Val Glu Leu
                290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
                340                 345                 350

Val Arg Phe Asp Asp Arg Val Thr Gly Lys Leu Glu Ala Phe Ala Ser
                355                 360                 365

Arg Ala Lys Ile Val His Ile Asp Ile Asp Ser Ala Glu Ile Gly Lys
                370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
                420                 425                 430

Pro Leu Gly Tyr Lys Thr Phe Gln Asp Ala Ile Ser Pro Gln His Ala
                435                 440                 445

Ile Glu Val Leu Asp Glu Leu Thr Asn Gly Asp Ala Ile Val Ser Thr
                450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495
```

```
Gly Leu Pro Ala Ala Ile Gly Ala Val Ala Asn Pro Gly Ala Val
            500                 505                 510

Val Val Asp Ile Asp Gly Asp Gly Ser Phe Ile Met Asn Val Gln Glu
515                 520                 525

Leu Ala Thr Ile Arg Val Glu Asn Leu Pro Val Lys Ile Leu Leu Leu
        530                 535                 540

Asn Asn Gln His Leu Gly Met Val Val Gln Leu Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
            580                 585                 590

Ala Ala Arg Val Thr Lys Lys Glu Glu Leu Arg Ala Ala Ile Gln Arg
        595                 600                 605

Met Leu Asp Thr Pro Gly Pro Tyr Leu Leu Asp Val Ile Val Pro His
    610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 14
<211> LENGTH: 651
<212> TYPE: PRT
<213> ORGANISM: ARTIFICIAL
<220> FEATURE:
<223> OTHER INFORMATION: ALS1 variant P178Q

<400> SEQUENCE: 14

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
            20                  25                  30

His Gln Thr Leu Thr Lys Pro Asn His Ala Leu Lys Ile Lys Cys Ser
        35                  40                  45

Ile Ser Lys Pro Pro Thr Ala Ala Pro Phe Thr Lys Glu Ala Pro Thr
    50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
            100                 105                 110

Arg Ser Ala Ala Ile Arg Asn Val Leu Pro Arg His Glu Gln Gly Gly
        115                 120                 125

Val Phe Ala Ala Glu Gly Tyr Ala Arg Ser Ser Gly Leu Pro Gly Val
    130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Gln Arg Arg Met Ile Gly Thr Asp Ala Phe Gln Glu Thr Pro Ile
            180                 185                 190

Val Glu Val Ser Arg Ser Ile Thr Lys His Asn Tyr Leu Ile Leu Asp
        195                 200                 205
```

```
Val Asp Asp Ile Pro Arg Val Val Ala Glu Ala Phe Phe Val Ala Thr
210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Ala Glu Ala Gln Leu Glu His
                260                 265                 270

Ile Val Arg Leu Ile Met Glu Ala Gln Lys Pro Val Leu Tyr Val Gly
                275                 280                 285

Gly Gly Ser Leu Asn Ser Ser Ala Glu Leu Arg Arg Phe Val Glu Leu
290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
                340                 345                 350

Val Arg Phe Asp Asp Arg Val Thr Gly Lys Leu Glu Ala Phe Ala Ser
                355                 360                 365

Arg Ala Lys Ile Val His Ile Asp Ile Asp Ser Ala Glu Ile Gly Lys
                370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
                420                 425                 430

Pro Leu Gly Tyr Lys Thr Phe Gln Asp Ala Ile Ser Pro Gln His Ala
                435                 440                 445

Ile Glu Val Leu Asp Glu Leu Thr Asn Gly Asp Ala Ile Val Ser Thr
                450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
                500                 505                 510

Val Val Asp Ile Asp Gly Asp Gly Ser Phe Ile Met Asn Val Gln Glu
                515                 520                 525

Leu Ala Thr Ile Arg Val Glu Asn Leu Pro Val Lys Ile Leu Leu Leu
530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
                580                 585                 590

Ala Ala Arg Val Thr Lys Lys Glu Glu Leu Arg Ala Ala Ile Gln Arg
                595                 600                 605

Met Leu Asp Thr Pro Gly Pro Tyr Leu Leu Asp Val Ile Val Pro His
610                 615                 620

Gln Glu His Val Leu Pro Met Ile Pro Ser Asn Gly Ser Phe Lys Asp
```

```
                625                 630                 635                 640
Val Ile Thr Glu Gly Asp Gly Arg Thr Arg Tyr
                    645                 650

<210> SEQ ID NO 15
<211> LENGTH: 651
<212> TYPE: PRT
<213> ORGANISM: ARTIFICIAL
<220> FEATURE:
<223> OTHER INFORMATION: ALS1 variant P178S

<400> SEQUENCE: 15

Met Ala Ala Thr Ala Ser Arg Thr Thr Arg Phe Ser Ser Ser Ser
1               5                   10                  15

His Pro Thr Phe Pro Lys Arg Ile Thr Arg Ser Thr Leu Pro Leu Ser
            20                  25                  30

His Gln Thr Leu Thr Lys Pro Asn His Ala Leu Lys Ile Lys Cys Ser
        35                  40                  45

Ile Ser Lys Pro Pro Thr Ala Ala Pro Phe Thr Lys Glu Ala Pro Thr
    50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
            100                 105                 110

Arg Ser Ala Ala Ile Arg Asn Val Leu Pro Arg His Glu Gln Gly Gly
        115                 120                 125

Val Phe Ala Ala Glu Gly Tyr Ala Arg Ser Ser Gly Leu Pro Gly Val
    130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Ser Arg Arg Met Ile Gly Thr Asp Ala Phe Gln Glu Thr Pro Ile
            180                 185                 190

Val Glu Val Ser Arg Ser Ile Thr Lys His Asn Tyr Leu Ile Leu Asp
        195                 200                 205

Val Asp Asp Ile Pro Arg Val Val Ala Glu Ala Phe Phe Val Ala Thr
    210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Pro Ala Glu Ala Gln Leu Glu His
            260                 265                 270

Ile Val Arg Leu Ile Met Glu Ala Gln Lys Pro Val Leu Tyr Val Gly
        275                 280                 285

Gly Gly Ser Leu Asn Ser Ser Ala Glu Leu Arg Arg Phe Val Glu Leu
    290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
```

-continued

```
                340                 345                 350
Val Arg Phe Asp Asp Arg Val Thr Gly Lys Leu Glu Ala Phe Ala Ser
            355                 360                 365
Arg Ala Lys Ile Val His Ile Asp Ile Asp Ser Ala Glu Ile Gly Lys
        370                 375                 380
Asn Lys Gln Ala His Val Ser Val Cys Ala Asp Leu Lys Leu Ala Leu
385                 390                 395                 400
Lys Gly Ile Asn Met Ile Leu Glu Glu Lys Gly Val Glu Gly Lys Phe
                405                 410                 415
Asp Leu Gly Gly Trp Arg Glu Glu Ile Asn Val Gln Lys His Lys Phe
            420                 425                 430
Pro Leu Gly Tyr Lys Thr Phe Gln Asp Ala Ile Ser Pro Gln His Ala
        435                 440                 445
Ile Glu Val Leu Asp Glu Leu Thr Asn Gly Asp Ala Ile Val Ser Thr
    450                 455                 460
Gly Val Gly Gln His Gln Met Trp Ala Ala Gln Phe Tyr Lys Tyr Lys
465                 470                 475                 480
Arg Pro Arg Gln Trp Leu Thr Ser Gly Gly Leu Gly Ala Met Gly Phe
                485                 490                 495
Gly Leu Pro Ala Ala Ile Gly Ala Ala Val Ala Asn Pro Gly Ala Val
            500                 505                 510
Val Val Asp Ile Asp Gly Asp Gly Ser Phe Ile Met Asn Val Gln Glu
        515                 520                 525
Leu Ala Thr Ile Arg Val Glu Asn Leu Pro Val Lys Ile Leu Leu Leu
    530                 535                 540
Asn Asn Gln His Leu Gly Met Val Val Gln Trp Glu Asp Arg Phe Tyr
545                 550                 555                 560
Lys Ser Asn Arg Ala His Thr Tyr Leu Gly Asp Pro Ser Ser Glu Ser
                565                 570                 575
Glu Ile Phe Pro Asn Met Leu Lys Phe Ala Asp Ala Cys Gly Ile Pro
            580                 585                 590
Ala Ala Arg Val Thr Lys Lys Glu Glu Leu Arg Ala Ala Ile Gln Arg
        595                 600                 605
Met Leu Asp Thr Pro Gly Pro Tyr Leu Leu Asp Val Ile Val Pro His
    610                 615                 620
Gln Glu His Val Leu Pro Met Ile Pro Ser Asn Gly Ser Phe Lys Asp
625                 630                 635                 640
Val Ile Thr Glu Gly Asp Gly Arg Thr Arg Tyr
                645                 650
```

<210> SEQ ID NO 16
<211> LENGTH: 651
<212> TYPE: PRT
<213> ORGANISM: ARTIFICIAL
<220> FEATURE:
<223> OTHER INFORMATION: ALS1 variant P178S A186V

<400> SEQUENCE: 16

```
Met Ala Ala Thr Ala Ser Arg Thr Thr Arg Phe Ser Ser Ser Ser Ser
1               5                   10                  15
His Pro Thr Phe Pro Lys Arg Ile Thr Arg Ser Thr Leu Pro Leu Ser
            20                  25                  30
His Gln Thr Leu Thr Lys Pro Asn His Ala Leu Lys Ile Lys Cys Ser
        35                  40                  45
Ile Ser Lys Pro Pro Thr Ala Ala Pro Phe Thr Lys Glu Ala Pro Thr
```

```
                50                  55                  60
Thr Glu Pro Phe Val Ser Arg Phe Ala Ser Gly Glu Pro Arg Lys Gly
 65                  70                  75                  80

Ala Asp Ile Leu Val Glu Ala Leu Glu Arg Gln Gly Val Thr Thr Val
                 85                  90                  95

Phe Ala Tyr Pro Gly Gly Ala Ser Met Glu Ile His Gln Ala Leu Thr
                100                 105                 110

Arg Ser Ala Ala Ile Arg Asn Val Leu Pro Arg His Glu Gln Gly Gly
                115                 120                 125

Val Phe Ala Ala Glu Gly Tyr Ala Arg Ser Ser Gly Leu Pro Gly Val
                130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Ala Ile Thr Gly Gln
                165                 170                 175

Val Ser Arg Arg Met Ile Gly Thr Asp Val Phe Gln Glu Thr Pro Ile
                180                 185                 190

Val Glu Val Ser Arg Ser Ile Thr Lys His Asn Tyr Leu Ile Leu Asp
                195                 200                 205

Val Asp Asp Ile Pro Arg Val Val Ala Glu Ala Phe Phe Val Ala Thr
                210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Ala Glu Ala Gln Leu Glu His
                260                 265                 270

Ile Val Arg Leu Ile Met Glu Ala Gln Lys Pro Val Leu Tyr Val Gly
                275                 280                 285

Gly Gly Ser Leu Asn Ser Ser Ala Glu Leu Arg Arg Phe Val Glu Leu
                290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
                340                 345                 350

Val Arg Phe Asp Asp Arg Val Thr Gly Lys Leu Glu Ala Phe Ala Ser
                355                 360                 365

Arg Ala Lys Ile Val His Ile Asp Ile Asp Ser Ala Glu Ile Gly Lys
                370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
                420                 425                 430

Pro Leu Gly Tyr Lys Thr Phe Gln Asp Ala Ile Ser Pro Gln His Ala
                435                 440                 445

Ile Glu Val Leu Asp Glu Leu Thr Asn Gly Asp Ala Ile Val Ser Thr
                450                 455                 460

Gly Val Gly Gln His Gln Met Trp Ala Ala Gln Phe Tyr Lys Tyr Lys
465                 470                 475                 480
```

```
Arg Pro Arg Gln Trp Leu Thr Ser Gly Gly Leu Gly Ala Met Gly Phe
            485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
            515                 520                 525

Leu Ala Thr Ile Arg Val Glu Asn Leu Pro Val Lys Ile Leu Leu Leu
            530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
                580                 585                 590

Ala Ala Arg Val Thr Lys Lys Glu Glu Leu Arg Ala Ala Ile Gln Arg
                595                 600                 605

Met Leu Asp Thr Pro Gly Pro Tyr Leu Leu Asp Val Ile Val Pro His
            610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 17
<211> LENGTH: 651
<212> TYPE: PRT
<213> ORGANISM: ARTIFICIAL
<220> FEATURE:
<223> OTHER INFORMATION: ALS1 variant P178S D357E

<400> SEQUENCE: 17

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
            20                  25                  30

His Gln Thr Leu Thr Lys Pro Asn His Ala Leu Lys Ile Lys Cys Ser
        35                  40                  45

Ile Ser Lys Pro Pro Thr Ala Ala Pro Phe Thr Lys Glu Ala Pro Thr
    50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
            100                 105                 110

Arg Ser Ala Ala Ile Arg Asn Val Leu Pro Arg His Glu Gln Gly Gly
        115                 120                 125

Val Phe Ala Ala Glu Gly Tyr Ala Arg Ser Ser Gly Leu Pro Gly Val
    130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Ser Arg Arg Met Ile Gly Thr Asp Ala Phe Gln Glu Thr Pro Ile
            180                 185                 190
```

```
Val Glu Val Ser Arg Ser Ile Thr Lys His Asn Tyr Leu Ile Leu Asp
            195                 200                 205

Val Asp Asp Ile Pro Arg Val Val Ala Glu Ala Phe Phe Val Ala Thr
    210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Ala Glu Ala Gln Leu Glu His
                260                 265                 270

Ile Val Arg Leu Ile Met Glu Ala Gln Lys Pro Val Leu Tyr Val Gly
            275                 280                 285

Gly Gly Ser Leu Asn Ser Ser Ala Glu Leu Arg Arg Phe Val Glu Leu
        290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
            340                 345                 350

Val Arg Phe Asp Glu Arg Val Thr Gly Lys Leu Glu Ala Phe Ala Ser
            355                 360                 365

Arg Ala Lys Ile Val His Ile Asp Ile Asp Ser Ala Glu Ile Gly Lys
        370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
            420                 425                 430

Pro Leu Gly Tyr Lys Thr Phe Gln Asp Ala Ile Ser Pro Gln His Ala
        435                 440                 445

Ile Glu Val Leu Asp Glu Leu Thr Asn Gly Asp Ala Ile Val Ser Thr
    450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
        515                 520                 525

Leu Ala Thr Ile Arg Val Glu Asn Leu Pro Val Lys Ile Leu Leu Leu
530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
            580                 585                 590

Ala Ala Arg Val Thr Lys Lys Glu Glu Leu Arg Ala Ala Ile Gln Arg
        595                 600                 605
```

-continued

```
Met Leu Asp Thr Pro Gly Pro Tyr Leu Leu Asp Val Ile Val Pro His
610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 18
<211> LENGTH: 651
<212> TYPE: PRT
<213> ORGANISM: ARTIFICIAL
<220> FEATURE:
<223> OTHER INFORMATION: ALS1 variant P178S D357N

<400> SEQUENCE: 18

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
                20                  25                  30

His Gln Thr Leu Thr Lys Pro Asn His Ala Leu Lys Ile Lys Cys Ser
            35                  40                  45

Ile Ser Lys Pro Pro Thr Ala Ala Pro Phe Thr Lys Glu Ala Pro Thr
50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
            100                 105                 110

Arg Ser Ala Ala Ile Arg Asn Val Leu Pro Arg His Glu Gln Gly Gly
        115                 120                 125

Val Phe Ala Ala Glu Gly Tyr Ala Arg Ser Ser Gly Leu Pro Gly Val
    130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Ser Arg Arg Met Ile Gly Thr Asp Ala Phe Gln Glu Thr Pro Ile
            180                 185                 190

Val Glu Val Ser Arg Ser Ile Thr Lys His Asn Tyr Leu Ile Leu Asp
        195                 200                 205

Val Asp Asp Ile Pro Arg Val Val Ala Glu Ala Phe Phe Val Ala Thr
    210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Ala Glu Ala Gln Leu Glu His
            260                 265                 270

Ile Val Arg Leu Ile Met Glu Ala Gln Lys Pro Val Leu Tyr Val Gly
        275                 280                 285

Gly Gly Ser Leu Asn Ser Ser Ala Glu Leu Arg Arg Phe Val Glu Leu
    290                 295                 300

Thr Gly Ile Pro Val Ala Ser Thr Leu Met Gly Leu Gly Thr Phe Pro
305                 310                 315                 320
```

```
Ile Gly Asp Glu Tyr Ser Leu Gln Met Leu Gly Met His Gly Thr Val
            325                 330                 335

Tyr Ala Asn Tyr Ala Val Asp Asn Ser Asp Leu Leu Leu Ala Phe Gly
            340                 345                 350

Val Arg Phe Asp Asn Arg Val Thr Gly Lys Leu Glu Ala Phe Ala Ser
            355                 360                 365

Arg Ala Lys Ile Val His Ile Asp Ile Asp Ser Ala Glu Ile Gly Lys
            370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
            405                 410                 415

Asp Leu Gly Gly Trp Arg Glu Glu Ile Asn Val Gln Lys His Lys Phe
            420                 425                 430

Pro Leu Gly Tyr Lys Thr Phe Gln Asp Ala Ile Ser Pro Gln His Ala
            435                 440                 445

Ile Glu Val Leu Asp Glu Leu Thr Asn Gly Asp Ala Ile Val Ser Thr
            450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
            485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
            515                 520                 525

Leu Ala Thr Ile Arg Val Glu Asn Leu Pro Val Lys Ile Leu Leu Leu
530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
            565                 570                 575

Glu Ile Phe Pro Asn Met Leu Lys Phe Ala Asp Ala Cys Gly Ile Pro
            580                 585                 590

Ala Ala Arg Val Thr Lys Lys Glu Glu Leu Arg Ala Ala Ile Gln Arg
            595                 600                 605

Met Leu Asp Thr Pro Gly Pro Tyr Leu Leu Asp Val Ile Val Pro His
            610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
            645                 650

<210> SEQ ID NO 19
<211> LENGTH: 651
<212> TYPE: PRT
<213> ORGANISM: ARTIFICIAL
<220> FEATURE:
<223> OTHER INFORMATION: ALS1 variant P178S F559D

<400> SEQUENCE: 19

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
            20                  25                  30
```

```
His Gln Thr Leu Thr Lys Pro Asn His Ala Leu Lys Ile Lys Cys Ser
         35                  40                  45

Ile Ser Lys Pro Pro Thr Ala Ala Pro Phe Thr Lys Glu Ala Pro Thr
     50                  55                  60

Thr Glu Pro Phe Val Ser Arg Phe Ala Ser Gly Glu Pro Arg Lys Gly
 65                  70                  75                  80

Ala Asp Ile Leu Val Glu Ala Leu Glu Arg Gln Gly Val Thr Thr Val
                 85                  90                  95

Phe Ala Tyr Pro Gly Gly Ala Ser Met Glu Ile His Gln Ala Leu Thr
            100                 105                 110

Arg Ser Ala Ala Ile Arg Asn Val Leu Pro Arg His Glu Gln Gly Gly
        115                 120                 125

Val Phe Ala Ala Glu Gly Tyr Ala Arg Ser Ser Gly Leu Pro Gly Val
    130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Ser Arg Arg Met Ile Gly Thr Asp Ala Phe Gln Glu Thr Pro Ile
                180                 185                 190

Val Glu Val Ser Arg Ser Ile Thr Lys His Asn Tyr Leu Ile Leu Asp
            195                 200                 205

Val Asp Asp Ile Pro Arg Val Val Ala Glu Ala Phe Phe Val Ala Thr
    210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Pro Ala Glu Ala Gln Leu Glu His
            260                 265                 270

Ile Val Arg Leu Ile Met Glu Ala Gln Lys Pro Val Leu Tyr Val Gly
    275                 280                 285

Gly Gly Ser Leu Asn Ser Ser Ala Glu Leu Arg Arg Phe Val Glu Leu
290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
            325                 330                 335

Tyr Ala Asn Tyr Ala Val Asp Asn Ser Asp Leu Leu Leu Ala Phe Gly
        340                 345                 350

Val Arg Phe Asp Asp Arg Val Thr Gly Lys Leu Glu Ala Phe Ala Ser
    355                 360                 365

Arg Ala Lys Ile Val His Ile Asp Ile Asp Ser Ala Glu Ile Gly Lys
370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
            405                 410                 415

Asp Leu Gly Gly Trp Arg Glu Ile Asn Val Gln Lys His Lys Phe
        420                 425                 430

Pro Leu Gly Tyr Lys Thr Phe Gln Asp Ala Ile Ser Pro Gln His Ala
    435                 440                 445

Ile Glu Val Leu Asp Glu Leu Thr Asn Gly Asp Ala Ile Val Ser Thr
```

```
                450                 455                 460
Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
                500                 505                 510

Val Val Asp Ile Asp Gly Asp Gly Ser Phe Ile Met Asn Val Gln Glu
                515                 520                 525

Leu Ala Thr Ile Arg Val Glu Asn Leu Pro Val Lys Ile Leu Leu Leu
                530                 535                 540

Asn Asn Gln His Leu Gly Met Val Val Gln Trp Glu Asp Arg Asp Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
                580                 585                 590

Ala Ala Arg Val Thr Lys Lys Glu Glu Leu Arg Ala Ala Ile Gln Arg
                595                 600                 605

Met Leu Asp Thr Pro Gly Pro Tyr Leu Leu Asp Val Ile Val Pro His
                610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 20
<211> LENGTH: 651
<212> TYPE: PRT
<213> ORGANISM: ARTIFICIAL
<220> FEATURE:
<223> OTHER INFORMATION: ALS1 variant A186D

<400> SEQUENCE: 20

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
                20                  25                  30

His Gln Thr Leu Thr Lys Pro Asn His Ala Leu Lys Ile Lys Cys Ser
                35                  40                  45

Ile Ser Lys Pro Pro Thr Ala Ala Pro Phe Thr Lys Glu Ala Pro Thr
50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
                100                 105                 110

Arg Ser Ala Ala Ile Arg Asn Val Leu Pro Arg His Glu Gln Gly Gly
                115                 120                 125

Val Phe Ala Ala Glu Gly Tyr Ala Arg Ser Ser Gly Leu Pro Gly Val
                130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
```

-continued

```
                165                 170                 175
Val Pro Arg Arg Met Ile Gly Thr Asp Asp Phe Gln Glu Thr Pro Ile
                180                 185                 190

Val Glu Val Ser Arg Ser Ile Thr Lys His Asn Tyr Leu Ile Leu Asp
                195                 200                 205

Val Asp Asp Ile Pro Arg Val Ala Glu Ala Phe Phe Val Ala Thr
        210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Pro Ala Glu Ala Gln Leu Glu His
                260                 265                 270

Ile Val Arg Leu Ile Met Glu Ala Gln Lys Pro Val Leu Tyr Val Gly
                275                 280                 285

Gly Gly Ser Leu Asn Ser Ser Ala Glu Leu Arg Arg Phe Val Glu Leu
            290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
                340                 345                 350

Val Arg Phe Asp Asp Arg Val Thr Gly Lys Leu Glu Ala Phe Ala Ser
                355                 360                 365

Arg Ala Lys Ile Val His Ile Asp Ile Asp Ser Ala Glu Ile Gly Lys
            370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
                420                 425                 430

Pro Leu Gly Tyr Lys Thr Phe Gln Asp Ala Ile Ser Pro Gln His Ala
            435                 440                 445

Ile Glu Val Leu Asp Glu Leu Thr Asn Gly Asp Ala Ile Val Ser Thr
450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
            515                 520                 525

Leu Ala Thr Ile Arg Val Glu Asn Leu Pro Val Lys Ile Leu Leu Leu
            530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
            580                 585                 590
```

```
Ala Ala Arg Val Thr Lys Lys Glu Glu Leu Arg Ala Ala Ile Gln Arg
            595                 600                 605

Met Leu Asp Thr Pro Gly Pro Tyr Leu Leu Asp Val Ile Val Pro His
    610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650
```

<210> SEQ ID NO 21
<211> LENGTH: 651
<212> TYPE: PRT
<213> ORGANISM: ARTIFICIAL
<220> FEATURE:
<223> OTHER INFORMATION: ALS1 variant A186V

<400> SEQUENCE: 21

```
Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
                20                  25                  30

His Gln Thr Leu Thr Lys Pro Asn His Ala Leu Lys Ile Lys Cys Ser
            35                  40                  45

Ile Ser Lys Pro Pro Thr Ala Ala Pro Phe Thr Lys Glu Ala Pro Thr
    50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
                100                 105                 110

Arg Ser Ala Ala Ile Arg Asn Val Leu Pro Arg His Glu Gln Gly Gly
            115                 120                 125

Val Phe Ala Ala Glu Gly Tyr Ala Arg Ser Ser Gly Leu Pro Gly Val
    130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Pro Arg Arg Met Ile Gly Thr Asp Val Phe Gln Glu Thr Pro Ile
            180                 185                 190

Val Glu Val Ser Arg Ser Ile Thr Lys His Asn Tyr Leu Ile Leu Asp
    195                 200                 205

Val Asp Asp Ile Pro Arg Val Val Ala Glu Ala Phe Phe Val Ala Thr
210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Ala Glu Ala Gln Leu Glu His
            260                 265                 270

Ile Val Arg Leu Ile Met Glu Ala Gln Lys Pro Val Leu Tyr Val Gly
        275                 280                 285

Gly Gly Ser Leu Asn Ser Ser Ala Glu Leu Arg Arg Phe Val Glu Leu
    290                 295                 300
```

```
Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
            325                 330                 335

Tyr Ala Asn Tyr Ala Val Asp Asn Ser Asp Leu Leu Leu Ala Phe Gly
        340                 345                 350

Val Arg Phe Asp Asp Arg Val Thr Gly Lys Leu Glu Ala Phe Ala Ser
            355                 360                 365

Arg Ala Lys Ile Val His Ile Asp Ile Asp Ser Ala Glu Ile Gly Lys
        370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
            420                 425                 430

Pro Leu Gly Tyr Lys Thr Phe Gln Asp Ala Ile Ser Pro Gln His Ala
        435                 440                 445

Ile Glu Val Leu Asp Glu Leu Thr Asn Gly Asp Ala Ile Val Ser Thr
    450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
        515                 520                 525

Leu Ala Thr Ile Arg Val Glu Asn Leu Pro Val Lys Ile Leu Leu Leu
    530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
            580                 585                 590

Ala Ala Arg Val Thr Lys Lys Glu Glu Leu Arg Ala Ala Ile Gln Arg
        595                 600                 605

Met Leu Asp Thr Pro Gly Pro Tyr Leu Leu Asp Val Ile Val Pro His
    610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 22
<211> LENGTH: 651
<212> TYPE: PRT
<213> ORGANISM: ARTIFICIAL
<220> FEATURE:
<223> OTHER INFORMATION: ALS1 variant K237F

<400> SEQUENCE: 22

Met Ala Ala Thr Ala Ser Arg Thr Thr Arg Phe Ser Ser Ser Ser Ser
1               5                   10                  15
```

```
His Pro Thr Phe Pro Lys Arg Ile Thr Arg Ser Thr Leu Pro Leu Ser
             20                  25                  30

His Gln Thr Leu Thr Lys Pro Asn His Ala Leu Lys Ile Lys Cys Ser
         35                  40                  45

Ile Ser Lys Pro Pro Thr Ala Ala Pro Phe Thr Lys Glu Ala Pro Thr
     50                  55                  60

Thr Glu Pro Phe Val Ser Arg Phe Ala Ser Gly Glu Pro Arg Lys Gly
 65                  70                  75                  80

Ala Asp Ile Leu Val Glu Ala Leu Glu Arg Gln Gly Val Thr Thr Val
                 85                  90                  95

Phe Ala Tyr Pro Gly Gly Ala Ser Met Glu Ile His Gln Ala Leu Thr
             100                 105                 110

Arg Ser Ala Ala Ile Arg Asn Val Leu Pro Arg His Glu Gln Gly Gly
         115                 120                 125

Val Phe Ala Ala Glu Gly Tyr Ala Arg Ser Ser Gly Leu Pro Gly Val
     130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                 165                 170                 175

Val Pro Arg Arg Met Ile Gly Thr Asp Ala Phe Gln Glu Thr Pro Ile
             180                 185                 190

Val Glu Val Ser Arg Ser Ile Thr Lys His Asn Tyr Leu Ile Leu Asp
         195                 200                 205

Val Asp Asp Ile Pro Arg Val Val Ala Glu Ala Phe Phe Val Ala Thr
     210                 215                 220

Ser Gly Arg Pro Gly Pro Val Leu Ile Asp Ile Pro Phe Asp Val Gln
225                 230                 235                 240

Gln Gln Leu Ala Val Pro Asn Trp Asp Glu Pro Val Asn Leu Pro Gly
                 245                 250                 255

Tyr Leu Ala Arg Leu Pro Arg Pro Pro Ala Glu Ala Gln Leu Glu His
             260                 265                 270

Ile Val Arg Leu Ile Met Glu Ala Gln Lys Pro Val Leu Tyr Val Gly
         275                 280                 285

Gly Gly Ser Leu Asn Ser Ser Ala Glu Leu Arg Arg Phe Val Glu Leu
     290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                 325                 330                 335

Tyr Ala Asn Tyr Ala Val Asp Asn Ser Asp Leu Leu Leu Ala Phe Gly
             340                 345                 350

Val Arg Phe Asp Asp Arg Val Thr Gly Lys Leu Glu Ala Phe Ala Ser
         355                 360                 365

Arg Ala Lys Ile Val His Ile Asp Ile Asp Ser Ala Glu Ile Gly Lys
     370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                 405                 410                 415

Asp Leu Gly Gly Trp Arg Glu Glu Ile Asn Val Gln Lys His Lys Phe
             420                 425                 430
```

```
Pro Leu Gly Tyr Lys Thr Phe Gln Asp Ala Ile Ser Pro Gln His Ala
            435                 440                 445

Ile Glu Val Leu Asp Glu Leu Thr Asn Gly Asp Ala Ile Val Ser Thr
450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Leu Gly Ala Met Gly Phe
                485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
            515                 520                 525

Leu Ala Thr Ile Arg Val Glu Asn Leu Pro Val Lys Ile Leu Leu Leu
            530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
                580                 585                 590

Ala Ala Arg Val Thr Lys Lys Glu Glu Leu Arg Ala Ala Ile Gln Arg
            595                 600                 605

Met Leu Asp Thr Pro Gly Pro Tyr Leu Leu Asp Val Ile Val Pro His
            610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 23
<211> LENGTH: 651
<212> TYPE: PRT
<213> ORGANISM: ARTIFICIAL
<220> FEATURE:
<223> OTHER INFORMATION: ALS1 variant K237Q

<400> SEQUENCE: 23

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
                20                  25                  30

His Gln Thr Leu Thr Lys Pro Asn His Ala Leu Lys Ile Lys Cys Ser
            35                  40                  45

Ile Ser Lys Pro Pro Thr Ala Ala Pro Phe Thr Lys Glu Ala Pro Thr
50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
            100                 105                 110

Arg Ser Ala Ala Ile Arg Asn Val Leu Pro Arg His Glu Gln Gly Gly
            115                 120                 125

Val Phe Ala Ala Glu Gly Tyr Ala Arg Ser Ser Gly Leu Pro Gly Val
            130                 135                 140
```

```
Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
            165                 170                 175

Val Pro Arg Arg Met Ile Gly Thr Asp Ala Phe Gln Glu Thr Pro Ile
            180                 185                 190

Val Glu Val Ser Arg Ser Ile Thr Lys His Asn Tyr Leu Ile Leu Asp
            195                 200                 205

Val Asp Asp Ile Pro Arg Val Ala Glu Ala Phe Phe Val Ala Thr
210                 215                 220

Ser Gly Arg Pro Gly Pro Val Leu Ile Asp Ile Pro Gln Asp Val Gln
225                 230                 235                 240

Gln Gln Leu Ala Val Pro Asn Trp Asp Glu Pro Val Asn Leu Pro Gly
            245                 250                 255

Tyr Leu Ala Arg Leu Pro Arg Pro Ala Glu Ala Gln Leu Glu His
            260                 265                 270

Ile Val Arg Leu Ile Met Glu Ala Gln Lys Pro Val Leu Tyr Val Gly
            275                 280                 285

Gly Gly Ser Leu Asn Ser Ser Ala Glu Leu Arg Arg Phe Val Glu Leu
290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
            325                 330                 335

Tyr Ala Asn Tyr Ala Val Asp Asn Ser Asp Leu Leu Leu Ala Phe Gly
            340                 345                 350

Val Arg Phe Asp Asp Arg Val Thr Gly Lys Leu Glu Ala Phe Ala Ser
            355                 360                 365

Arg Ala Lys Ile Val His Ile Asp Ile Asp Ser Ala Glu Ile Gly Lys
            370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
            405                 410                 415

Asp Leu Gly Gly Trp Arg Glu Glu Ile Asn Val Gln Lys His Lys Phe
            420                 425                 430

Pro Leu Gly Tyr Lys Thr Phe Gln Asp Ala Ile Ser Pro Gln His Ala
            435                 440                 445

Ile Glu Val Leu Asp Glu Leu Thr Asn Gly Asp Ala Ile Val Ser Thr
450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
            485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
            515                 520                 525

Leu Ala Thr Ile Arg Val Glu Asn Leu Pro Val Lys Ile Leu Leu Leu
            530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
```

```
                   565                 570                 575
Glu Ile Phe Pro Asn Met Leu Lys Phe Ala Asp Ala Cys Gly Ile Pro
                580                 585                 590

Ala Ala Arg Val Thr Lys Lys Glu Glu Leu Arg Ala Ile Gln Arg
            595                 600                 605

Met Leu Asp Thr Pro Gly Pro Tyr Leu Leu Asp Val Ile Val Pro His
        610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 24
<211> LENGTH: 651
<212> TYPE: PRT
<213> ORGANISM: ARTIFICIAL
<220> FEATURE:
<223> OTHER INFORMATION: ALS1 variant D357E

<400> SEQUENCE: 24

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
            20                  25                  30

His Gln Thr Leu Thr Lys Pro Asn His Ala Leu Lys Ile Lys Cys Ser
        35                  40                  45

Ile Ser Lys Pro Pro Thr Ala Ala Pro Phe Thr Lys Glu Ala Pro Thr
50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
            100                 105                 110

Arg Ser Ala Ala Ile Arg Asn Val Leu Pro Arg His Glu Gln Gly Gly
        115                 120                 125

Val Phe Ala Ala Glu Gly Tyr Ala Arg Ser Ser Gly Leu Pro Gly Val
    130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Pro Arg Arg Met Ile Gly Thr Asp Ala Phe Gln Glu Thr Pro Ile
            180                 185                 190

Val Glu Val Ser Arg Ser Ile Thr Lys His Asn Tyr Leu Ile Leu Asp
        195                 200                 205

Val Asp Asp Ile Pro Arg Val Val Ala Glu Ala Phe Phe Val Ala Thr
    210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Pro Ala Glu Ala Gln Leu Glu His
            260                 265                 270

Ile Val Arg Leu Ile Met Glu Ala Gln Lys Pro Val Leu Tyr Val Gly
```

```
                275                 280                 285
Gly Gly Ser Leu Asn Ser Ser Ala Glu Leu Arg Arg Phe Val Glu Leu
        290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
                340                 345                 350

Val Arg Phe Asp Glu Arg Val Thr Gly Lys Leu Glu Ala Phe Ala Ser
                355                 360                 365

Arg Ala Lys Ile Val His Ile Asp Ile Asp Ser Ala Glu Ile Gly Lys
        370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
                420                 425                 430

Pro Leu Gly Tyr Lys Thr Phe Gln Asp Ala Ile Ser Pro Gln His Ala
        435                 440                 445

Ile Glu Val Leu Asp Glu Leu Thr Asn Gly Asp Ala Ile Val Ser Thr
450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
                500                 505                 510

Val Val Asp Ile Asp Gly Asp Gly Ser Phe Ile Met Asn Val Gln Glu
                515                 520                 525

Leu Ala Thr Ile Arg Val Glu Asn Leu Pro Val Lys Ile Leu Leu Leu
        530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
                580                 585                 590

Ala Ala Arg Val Thr Lys Lys Glu Glu Leu Arg Ala Ala Ile Gln Arg
        595                 600                 605

Met Leu Asp Thr Pro Gly Pro Tyr Leu Leu Asp Val Ile Val Pro His
610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 25
<211> LENGTH: 651
<212> TYPE: PRT
<213> ORGANISM: ARTIFICIAL
<220> FEATURE:
<223> OTHER INFORMATION: ALS1 variant D357N
```

```
<400> SEQUENCE: 25

Met Ala Ala Thr Ala Ser Arg Thr Thr Arg Phe Ser Ser Ser Ser
1               5                   10                  15

His Pro Thr Phe Pro Lys Arg Ile Thr Arg Ser Thr Leu Pro Leu Ser
                20                  25                  30

His Gln Thr Leu Thr Lys Pro Asn His Ala Leu Lys Ile Lys Cys Ser
            35                  40                  45

Ile Ser Lys Pro Pro Thr Ala Ala Pro Phe Thr Lys Glu Ala Pro Thr
    50                  55                  60

Thr Glu Pro Phe Val Ser Arg Phe Ala Ser Gly Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
                100                 105                 110

Arg Ser Ala Ala Ile Arg Asn Val Leu Pro Arg His Glu Gln Gly Gly
            115                 120                 125

Val Phe Ala Ala Glu Gly Tyr Ala Arg Ser Ser Gly Leu Pro Gly Val
        130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Pro Arg Arg Met Ile Gly Thr Asp Ala Phe Gln Glu Thr Pro Ile
                180                 185                 190

Val Glu Val Ser Arg Ser Ile Thr Lys His Asn Tyr Leu Ile Leu Asp
            195                 200                 205

Val Asp Asp Ile Pro Arg Val Val Ala Glu Ala Phe Phe Val Ala Thr
    210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Pro Ala Glu Ala Gln Leu Glu His
                260                 265                 270

Ile Val Arg Leu Ile Met Glu Ala Gln Lys Pro Val Leu Tyr Val Gly
            275                 280                 285

Gly Gly Ser Leu Asn Ser Ser Ala Glu Leu Arg Arg Phe Val Glu Leu
        290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
                340                 345                 350

Val Arg Phe Asp Asn Arg Val Thr Gly Lys Leu Glu Ala Phe Ala Ser
            355                 360                 365

Arg Ala Lys Ile Val His Ile Asp Ile Asp Ser Ala Glu Ile Gly Lys
    370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415
```

```
Asp Leu Gly Gly Trp Arg Glu Ile Asn Val Gln Lys His Lys Phe
            420                 425                 430

Pro Leu Gly Tyr Lys Thr Phe Gln Asp Ala Ile Ser Pro Gln His Ala
            435                 440                 445

Ile Glu Val Leu Asp Glu Leu Thr Asn Gly Asp Ala Ile Val Ser Thr
450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
                500                 505                 510

Val Val Asp Ile Asp Gly Asp Gly Ser Phe Ile Met Asn Val Gln Glu
            515                 520                 525

Leu Ala Thr Ile Arg Val Glu Asn Leu Pro Val Lys Ile Leu Leu Leu
            530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
                580                 585                 590

Ala Ala Arg Val Thr Lys Lys Glu Glu Leu Arg Ala Ala Ile Gln Arg
            595                 600                 605

Met Leu Asp Thr Pro Gly Pro Tyr Leu Leu Asp Val Ile Val Pro His
            610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 26
<211> LENGTH: 651
<212> TYPE: PRT
<213> ORGANISM: ARTIFICIAL
<220> FEATURE:
<223> OTHER INFORMATION: ALS1 variant W555L

<400> SEQUENCE: 26

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
            20                  25                  30

His Gln Thr Leu Thr Lys Pro Asn His Ala Leu Lys Ile Lys Cys Ser
        35                  40                  45

Ile Ser Lys Pro Pro Thr Ala Ala Pro Phe Thr Lys Glu Ala Pro Thr
    50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
            100                 105                 110

Arg Ser Ala Ala Ile Arg Asn Val Leu Pro Arg His Glu Gln Gly Gly
        115                 120                 125
```

-continued

```
Val Phe Ala Ala Glu Gly Tyr Ala Arg Ser Ser Gly Leu Pro Gly Val
    130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Ala Ile Thr Gly Gln
                165                 170                 175

Val Pro Arg Arg Met Ile Gly Thr Asp Ala Phe Gln Glu Thr Pro Ile
                180                 185                 190

Val Glu Val Ser Arg Ser Ile Thr Lys His Asn Tyr Leu Ile Leu Asp
            195                 200                 205

Val Asp Asp Ile Pro Arg Val Val Ala Glu Ala Phe Phe Val Ala Thr
    210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Ala Glu Ala Gln Leu Glu His
                260                 265                 270

Ile Val Arg Leu Ile Met Glu Ala Gln Lys Pro Val Leu Tyr Val Gly
            275                 280                 285

Gly Gly Ser Leu Asn Ser Ser Ala Glu Leu Arg Arg Phe Val Glu Leu
    290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
                340                 345                 350

Val Arg Phe Asp Asp Arg Val Thr Gly Lys Leu Glu Ala Phe Ala Ser
            355                 360                 365

Arg Ala Lys Ile Val His Ile Asp Ile Asp Ser Ala Glu Ile Gly Lys
    370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
            420                 425                 430

Pro Leu Gly Tyr Lys Thr Phe Gln Asp Ala Ile Ser Pro Gln His Ala
    435                 440                 445

Ile Glu Val Leu Asp Glu Leu Thr Asn Gly Asp Ala Ile Val Ser Thr
450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
    515                 520                 525

Leu Ala Thr Ile Arg Val Glu Asn Leu Pro Val Lys Ile Leu Leu Leu
530                 535                 540
```

```
Asn Asn Gln His Leu Gly Met Val Val Gln Leu Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
                580                 585                 590

Ala Ala Arg Val Thr Lys Lys Glu Glu Leu Arg Ala Ile Gln Arg
                595                 600                 605

Met Leu Asp Thr Pro Gly Pro Tyr Leu Leu Asp Val Ile Val Pro His
                610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 27
<211> LENGTH: 651
<212> TYPE: PRT
<213> ORGANISM: ARTIFICIAL
<220> FEATURE:
<223> OTHER INFORMATION: ALS1 variant F559D

<400> SEQUENCE: 27

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
                20                  25                  30

His Gln Thr Leu Thr Lys Pro Asn His Ala Leu Lys Ile Lys Cys Ser
                35                  40                  45

Ile Ser Lys Pro Pro Thr Ala Ala Pro Phe Thr Lys Glu Ala Pro Thr
50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
                100                 105                 110

Arg Ser Ala Ala Ile Arg Asn Val Leu Pro Arg His Glu Gln Gly Gly
                115                 120                 125

Val Phe Ala Ala Glu Gly Tyr Ala Arg Ser Ser Gly Leu Pro Gly Val
                130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Pro Arg Arg Met Ile Gly Thr Asp Ala Phe Gln Glu Thr Pro Ile
                180                 185                 190

Val Glu Val Ser Arg Ser Ile Thr Lys His Asn Tyr Leu Ile Leu Asp
                195                 200                 205

Val Asp Asp Ile Pro Arg Val Val Ala Glu Ala Phe Phe Val Ala Thr
                210                 215                 220

Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255
```

```
Tyr Leu Ala Arg Leu Pro Arg Pro Ala Glu Ala Gln Leu Glu His
            260                 265                 270

Ile Val Arg Leu Ile Met Glu Ala Gln Lys Pro Val Leu Tyr Val Gly
            275                 280                 285

Gly Gly Ser Leu Asn Ser Ser Ala Glu Leu Arg Arg Phe Val Glu Leu
290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Ala Phe Gly
            340                 345                 350

Val Arg Phe Asp Asp Arg Val Thr Gly Lys Leu Glu Ala Phe Ala Ser
            355                 360                 365

Arg Ala Lys Ile Val His Ile Asp Ile Asp Ser Ala Glu Ile Gly Lys
            370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
            420                 425                 430

Pro Leu Gly Tyr Lys Thr Phe Gln Asp Ala Ile Ser Pro Gln His Ala
            435                 440                 445

Ile Glu Val Leu Asp Glu Leu Thr Asn Gly Asp Ala Ile Val Ser Thr
450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
            500                 505                 510

Val Val Asp Ile Asp Gly Asp Gly Ser Phe Ile Met Asn Val Gln Glu
            515                 520                 525

Leu Ala Thr Ile Arg Val Glu Asn Leu Pro Val Lys Ile Leu Leu Leu
530                 535                 540

Asn Asn Gln His Leu Gly Met Val Val Gln Trp Glu Asp Arg Asp Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
            580                 585                 590

Ala Ala Arg Val Thr Lys Lys Glu Glu Leu Arg Ala Ala Ile Gln Arg
            595                 600                 605

Met Leu Asp Thr Pro Gly Pro Tyr Leu Leu Asp Val Ile Val Pro His
610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650

<210> SEQ ID NO 28
<211> LENGTH: 651
<212> TYPE: PRT
```

```
<213> ORGANISM: ARTIFICIAL
<220> FEATURE:
<223> OTHER INFORMATION: F559L

<400> SEQUENCE: 28
```

| | | | | | | | | | | | | | | | |
|---|---|---|---|---|---|---|---|---|---|---|---|---|---|---|---|
| Met | Ala | Ala | Thr | Ala | Ser | Arg | Thr | Thr | Arg | Phe | Ser | Ser | Ser | Ser | Ser |
| 1 | | | | 5 | | | | | 10 | | | | | 15 | |
| His | Pro | Thr | Phe | Pro | Lys | Arg | Ile | Thr | Arg | Ser | Thr | Leu | Pro | Leu | Ser |
| | | | 20 | | | | | 25 | | | | | 30 | | |
| His | Gln | Thr | Leu | Thr | Lys | Pro | Asn | His | Ala | Leu | Lys | Ile | Lys | Cys | Ser |
| | | 35 | | | | | 40 | | | | | 45 | | | |
| Ile | Ser | Lys | Pro | Pro | Thr | Ala | Ala | Pro | Phe | Thr | Lys | Glu | Ala | Pro | Thr |
| 50 | | | | | 55 | | | | | 60 | | | | | |
| Thr | Glu | Pro | Phe | Val | Ser | Arg | Phe | Ala | Ser | Gly | Glu | Pro | Arg | Lys | Gly |
| 65 | | | | | 70 | | | | | 75 | | | | | 80 |
| Ala | Asp | Ile | Leu | Val | Glu | Ala | Leu | Glu | Arg | Gln | Gly | Val | Thr | Thr | Val |
| | | | | 85 | | | | | 90 | | | | | 95 | |
| Phe | Ala | Tyr | Pro | Gly | Gly | Ala | Ser | Met | Glu | Ile | His | Gln | Ala | Leu | Thr |
| | | | 100 | | | | | 105 | | | | | 110 | | |
| Arg | Ser | Ala | Ala | Ile | Arg | Asn | Val | Leu | Pro | Arg | His | Glu | Gln | Gly | Gly |
| | | 115 | | | | | 120 | | | | | 125 | | | |
| Val | Phe | Ala | Ala | Glu | Gly | Tyr | Ala | Arg | Ser | Ser | Gly | Leu | Pro | Gly | Val |
| 130 | | | | | 135 | | | | | 140 | | | | | |
| Cys | Ile | Ala | Thr | Ser | Gly | Pro | Gly | Ala | Thr | Asn | Leu | Val | Ser | Gly | Leu |
| 145 | | | | | 150 | | | | | 155 | | | | | 160 |
| Ala | Asp | Ala | Leu | Met | Asp | Ser | Val | Pro | Val | Val | Ala | Ile | Thr | Gly | Gln |
| | | | | 165 | | | | | 170 | | | | | 175 | |
| Val | Pro | Arg | Arg | Met | Ile | Gly | Thr | Asp | Ala | Phe | Gln | Glu | Thr | Pro | Ile |
| | | | 180 | | | | | 185 | | | | | 190 | | |
| Val | Glu | Val | Ser | Arg | Ser | Ile | Thr | Lys | His | Asn | Tyr | Leu | Ile | Leu | Asp |
| | | 195 | | | | | 200 | | | | | 205 | | | |
| Val | Asp | Asp | Ile | Pro | Arg | Val | Val | Ala | Glu | Ala | Phe | Phe | Val | Ala | Thr |
| 210 | | | | | 215 | | | | | 220 | | | | | |
| Ser | Gly | Arg | Pro | Gly | Pro | Val | Leu | Ile | Asp | Ile | Pro | Lys | Asp | Val | Gln |
| 225 | | | | | 230 | | | | | 235 | | | | | 240 |
| Gln | Gln | Leu | Ala | Val | Pro | Asn | Trp | Asp | Glu | Pro | Val | Asn | Leu | Pro | Gly |
| | | | | 245 | | | | | 250 | | | | | 255 | |
| Tyr | Leu | Ala | Arg | Leu | Pro | Arg | Pro | Ala | Glu | Ala | Gln | Leu | Glu | His | |
| | | | 260 | | | | | 265 | | | | | 270 | | |
| Ile | Val | Arg | Leu | Ile | Met | Glu | Ala | Gln | Lys | Pro | Val | Leu | Tyr | Val | Gly |
| | | 275 | | | | | 280 | | | | | 285 | | | |
| Gly | Gly | Ser | Leu | Asn | Ser | Ser | Ala | Glu | Leu | Arg | Arg | Phe | Val | Glu | Leu |
| 290 | | | | | 295 | | | | | 300 | | | | | |
| Thr | Gly | Ile | Pro | Val | Ala | Ser | Thr | Leu | Met | Gly | Leu | Gly | Thr | Phe | Pro |
| 305 | | | | | 310 | | | | | 315 | | | | | 320 |
| Ile | Gly | Asp | Glu | Tyr | Ser | Leu | Gln | Met | Leu | Gly | Met | His | Gly | Thr | Val |
| | | | | 325 | | | | | 330 | | | | | 335 | |
| Tyr | Ala | Asn | Tyr | Ala | Val | Asp | Asn | Ser | Asp | Leu | Leu | Leu | Ala | Phe | Gly |
| | | | 340 | | | | | 345 | | | | | 350 | | |
| Val | Arg | Phe | Asp | Asp | Arg | Val | Thr | Gly | Lys | Leu | Glu | Ala | Phe | Ala | Ser |
| | | 355 | | | | | 360 | | | | | 365 | | | |
| Arg | Ala | Lys | Ile | Val | His | Ile | Asp | Ile | Asp | Ser | Ala | Glu | Ile | Gly | Lys |
| 370 | | | | | 375 | | | | | 380 | | | | | |
| Asn | Lys | Gln | Ala | His | Val | Ser | Val | Cys | Ala | Asp | Leu | Lys | Leu | Ala | Leu |

-continued

```
385                 390                 395                 400
Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
                420                 425                 430

Pro Leu Gly Tyr Lys Thr Phe Gln Asp Ala Ile Ser Pro Gln His Ala
                435                 440                 445

Ile Glu Val Leu Asp Glu Leu Thr Asn Gly Asp Ala Ile Val Ser Thr
            450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
                500                 505                 510

Val Val Asp Ile Asp Gly Asp Gly Ser Phe Ile Met Asn Val Gln Glu
                515                 520                 525

Leu Ala Thr Ile Arg Val Glu Asn Leu Pro Val Lys Ile Leu Leu Leu
            530                 535                 540

Asn Asn Gln His Leu Gly Met Val Val Gln Trp Glu Asp Arg Leu Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
                580                 585                 590

Ala Ala Arg Val Thr Lys Lys Glu Glu Leu Arg Ala Ala Ile Gln Arg
            595                 600                 605

Met Leu Asp Thr Pro Gly Pro Tyr Leu Leu Asp Val Ile Val Pro His
            610                 615                 620

Gln Glu His Val Leu Pro Met Ile Pro Ser Asn Gly Ser Phe Lys Asp
625                 630                 635                 640

Val Ile Thr Glu Gly Asp Gly Arg Thr Arg Tyr
                645                 650
```